US012766273B2

(12) United States Patent
Shahaf et al.

(10) Patent No.: US 12,766,273 B2
(45) Date of Patent: Oct. 20, 2026

(54) DEVICES AND METHODS FOR DELIVERING A SUBSTANCE TO A BODY CAVITY

(71) Applicant: SipNose Ltd., Yokneam (IL)

(72) Inventors: Daniel Shahaf, M.P. Emek Ha-Yarden (IL); Iris Shichor, Zichron Ya'akov (IL); Liron Shavit Hadar, Haifa (IL); Lia Kaufman, Zichron Ya'akov (IL)

(73) Assignee: AptarGroup, Inc., Crystal Lake, IL (US)

( * ) Notice: Subject to any disclaimer, the term of this patent is extended or adjusted under 35 U.S.C. 154(b) by 1384 days.

(21) Appl. No.: 17/358,707

(22) Filed: Jun. 25, 2021

(65) Prior Publication Data

US 2022/0032021 A1 Feb. 3, 2022

Related U.S. Application Data

(63) Continuation-in-part of application No. PCT/IB2021/051834, filed on Mar. 4, 2021, and a
(Continued)

(30) Foreign Application Priority Data

Dec. 16, 2013 (DE) .......................... 2020131057150

(51) Int. Cl.
*A61M 11/02* (2006.01)
*A61M 13/00* (2006.01)
(Continued)

(52) U.S. Cl.
CPC ............ *A61M 11/02* (2013.01); *A61M 13/00* (2013.01); *A61M 15/0036* (2014.02);
(Continued)

(58) Field of Classification Search
CPC .. A61M 11/00; A61M 11/006; A61M 11/007; A61M 11/008; A61M 11/001;
(Continued)

(56) References Cited

U.S. PATENT DOCUMENTS

| | | | |
|---|---|---|---|
| 462,990 | A | 11/1891 | Oppenheimer |
| 3,921,637 | A | 11/1975 | Bennie et al. |

(Continued)

FOREIGN PATENT DOCUMENTS

| | | |
|---|---|---|
| CN | 1981886 | 6/2007 |
| CN | 104520198 | 4/2015 |

(Continued)

OTHER PUBLICATIONS

Affidavit of Ms. Lia Kaufman dtd Aug. 3, 2020, pp. 1-9, with Facts and Arguments brief, published Aug. 7, 2020 in the Register of the Opposition proceedings in EP 3400047 B1, available at https://register.epo.org/application?number=EP17711702&lng=en&tab=doclist (last accessed Nov. 9, 2023).

(Continued)

*Primary Examiner* — Colin W Stuart
(74) *Attorney, Agent, or Firm* — Foley & Lardner LLP

(57) ABSTRACT

Methods and devices are provided for delivering one or more substances within at least one body cavity. Such devices include at least one nosepiece having at least one capsule including a volume $V_{sub}$ of the substances; at least one base in communication with the nosepiece, the base having at least one chamber configured to confine pressurized fluid at volume $V_{PF}$ and pressure $P_{PF}$, and at least one hollow puncturing member having at least one sharp end and a second end in fluid communication with the base. The first and second ends are fluidly interconnected by at least one hollow tube. A fluid inlet port of the capsule is configured in
(Continued)

terms of size and shape to interface in a sealable manner with at least one end of the at least one puncturing member.

72 Claims, 44 Drawing Sheets

Related U.S. Application Data continuation-in-part of application No. 16/809,994, filed on Mar. 5, 2020, now Pat. No. 11,992,604, which is a continuation-in-part of application No. 16/810,096, filed on Mar. 5, 2020, now abandoned, and a continuation-in-part of application No. 15/982,996, filed on May 17, 2018, now Pat. No. 11,471,618, said application No. 16/810,096 is a continuation-in-part of application No. 15/982,630, filed on May 17, 2018, now Pat. No. 11,278,682, said application No. 15/982,996 is a continuation-in-part of application No. 14/733,143, filed on Jun. 8, 2015, now Pat. No. 11,116,914, said application No. 15/982,630 is a continuation-in-part of application No. 14/733,143, filed on Jun. 8, 2015, now Pat. No. 11,116,914, said application No. 16/809,994 is a continuation-in-part of application No. 14/433,048, filed as application No. PCT/IL2014/050752 on Aug. 21, 2014, now Pat. No. 11,383,048.

(60) Provisional application No. 63/113,834, filed on Nov. 14, 2020, provisional application No. 62/526,386, filed on Jun. 29, 2017, provisional application No. 62/507,816, filed on May 18, 2017, provisional application No. 62/117,986, filed on Feb. 19, 2015, provisional application No. 62/077,246, filed on Nov. 9, 2014, provisional application No. 61/868,627, filed on Aug. 22, 2013, provisional application No. 61/868,614, filed on Aug. 22, 2013.

(51) Int. Cl.

*A61M 15/00* (2006.01)
*A61M 15/08* (2006.01)
*A61M 31/00* (2006.01)

(52) U.S. Cl.

CPC ............ *A61M 15/08* (2013.01); *A61M 31/00* (2013.01); *A61M 15/0028* (2013.01); *A61M 2202/064* (2013.01); *A61M 2205/276* (2013.01)

(58) Field of Classification Search

CPC ...... A61M 11/02; A61M 11/08; A61M 15/00; A61M 15/0001; A61M 15/009; A61M 15/0036; A61M 2202/04; A61M 2202/064; A61M 2210/0618; A61M 31/00

See application file for complete search history.

(56) References Cited

U.S. PATENT DOCUMENTS 3,998,226 A 12/1976 Harris
4,017,007 A 4/1977 Riccio
4,114,615 A 9/1978 Wetterlin
4,620,670 A 11/1986 Hughes
5,048,729 A 9/1991 Pritchard
5,307,953 A 5/1994 Regan
5,740,794 A 4/1998 Smith et al.
6,123,228 A 9/2000 Hippensteel
6,135,979 A * 10/2000 Weston .............. A61M 5/2033 604/134
6,186,141 B1 2/2001 Pike et al.
6,398,074 B1 6/2002 Bruna et al.
6,708,846 B1 3/2004 Fuchs et al.
6,971,385 B1 12/2005 Flora
7,497,390 B2 3/2009 Beller
7,726,308 B1 6/2010 Flora
7,802,569 B2 9/2010 Yeates et al.
7,900,659 B2 3/2011 Whitley et al.
8,360,056 B2 1/2013 Ishizeki et al.
2001/0008637 A1 7/2001 Hochrainer et al.
2002/0023641 A1 2/2002 Stadelhofer
2002/0092520 A1 7/2002 Casper et al.
2002/0092521 A1 7/2002 Sullivan et al.
2002/0092524 A1 7/2002 Lockhart et al.
2002/0174865 A1 11/2002 Gatton et al.
2003/0015191 A1 * 1/2003 Armstrong ........ A61M 15/0028 222/402.1
2003/0079743 A1 5/2003 Genova et al.
2003/0127533 A1 7/2003 Stihl
2003/0181917 A1 9/2003 Gertner
2003/0187404 A1 10/2003 Waldenburg
2003/0209455 A1 11/2003 Pynson et al.
2004/0050885 A1 3/2004 Stradella
2004/0153033 A1 8/2004 Mazzoni
2005/0028812 A1 2/2005 Djupesland
2005/0131357 A1 6/2005 Denton et al.
2005/0188985 A1 9/2005 Sullivan et al.
2006/0067911 A1 3/2006 Nilsson et al.
2006/0107957 A1 5/2006 Djupesland
2006/0151629 A1 7/2006 Vedrine et al.
2006/0213514 A1 9/2006 Price et al.
2006/0254583 A1 11/2006 Deboeck et al.
2006/0254585 A1 11/2006 Ishizeki et al.
2007/0051362 A1 3/2007 Sullivan et al.
2007/0060868 A1 3/2007 Tsutsui
2007/0125371 A1 6/2007 Djupesland
2007/0151562 A1 7/2007 Jones et al.
2007/0154407 A1 7/2007 Peters et al.
2007/0256688 A1 11/2007 Schuster et al.
2008/0029084 A1 2/2008 Costantino et al.
2008/0092887 A1 4/2008 Hodson et al.
2008/0177246 A1 7/2008 Sullivan et al.
2008/0210229 A1 9/2008 Corbacho
2009/0166379 A1 7/2009 Wright et al.
2009/0275668 A1 11/2009 Kamishita
2009/0285849 A1 11/2009 Barsanti et al.
2009/0308388 A1 12/2009 Chawla
2009/0314293 A1 12/2009 Djupesland
2010/0083963 A1 4/2010 Wharton et al.
2010/0258115 A1 10/2010 Kawamura et al.
2010/0282246 A1 11/2010 Djupesland et al.
2010/0331765 A1 12/2010 Sullivan et al.
2011/0011398 A1 1/2011 Yeates
2011/0048414 A1 3/2011 Hoekman et al.
2011/0088690 A1 4/2011 Djupesland et al.
2011/0168172 A1 7/2011 Patton et al.
2011/0283996 A1 11/2011 Abrams
2012/0291779 A1 11/2012 Haartsen et al.
2013/0096495 A1 4/2013 Holmqvist et al.
2013/0180524 A1 7/2013 Shahaf et al.
2013/0239964 A1 * 9/2013 Young .............. A61M 15/0003 128/203.12
2013/0267864 A1 10/2013 Addington et al.
2013/0299607 A1 11/2013 Wilkerson et al.
2013/0345673 A1 12/2013 Ferreri et al.
2014/0060532 A1 3/2014 Hodges et al.
2015/0122257 A1 5/2015 Winkler et al.
2015/0144129 A1 5/2015 Djupesland et al.
2015/0165136 A1 6/2015 Galgon et al.
2015/0174343 A1 6/2015 Muellinger et al.
2015/0209325 A1 7/2015 Najarian et al.
2015/0258287 A1 9/2015 Shahaf et al.
2015/0297845 A1 10/2015 Shahaf et al.
2016/0101245 A1 * 4/2016 Hoekman ......... A61M 15/0035 264/537
2016/0101246 A1 * 4/2016 Dennis .................... A61P 21/02 128/200.14
2016/0129205 A1 5/2016 Shahaf et al.
2018/0072480 A1 3/2018 Genosar
2018/0110922 A1 4/2018 Dunki-Jacobs et al.

(56) References Cited

U.S. PATENT DOCUMENTS

| | | | |
|---|---|---|---|
| 2018/0344950 A1 | 12/2018 | Goumeniouk et al. | |
| 2019/0015613 A1 | 1/2019 | Shahaf et al. | |
| 2019/0060168 A1 | 2/2019 | Koska | |
| 2020/0197631 A1 | 6/2020 | Stedman et al. | |
| 2020/0197633 A1 | 6/2020 | Shahaf et al. | |
| 2020/0289768 A1 | 9/2020 | Shahaf et al. | |
| 2020/0289769 A1 | 9/2020 | Poullain | |
| 2020/0306463 A1 | 10/2020 | Shahaf et al. | |
| 2020/0398006 A1 | 12/2020 | Clark et al. | |

FOREIGN PATENT DOCUMENTS

| | | |
|---|---|---|
| CN | 107580513 | 1/2018 |
| DE | 19502725 | 8/1996 |
| DE | 19708406 | 9/1998 |
| DE | 20-2013-105715 U1 | 3/2014 |
| EP | 1 023 098 B1 | 9/2004 |
| EP | 1 752 176 A1 | 2/2007 |
| EP | 2 002 856 A1 | 12/2008 |
| EP | 2 030 645 A1 | 3/2009 |
| EP | 2 922 770 | 9/2015 |
| GB | 0 724 974 A | 2/1955 |
| GB | 2 415 376 A | 12/2005 |
| JP | 2002-505981 A | 2/2002 |
| WO | WO-90/12567 A1 | 11/1990 |
| WO | WO-99/46055 | 9/1999 |
| WO | WO-99/58180 | 11/1999 |
| WO | WO-02/055133 A2 | 7/2002 |
| WO | WO-02/060517 A2 | 8/2002 |
| WO | WO-2009/002267 | 12/2008 |
| WO | WO-2012/029064 A1 | 3/2012 |
| WO | WO-2012/105236 A1 | 8/2012 |
| WO | WO-2013/128447 A1 | 9/2013 |
| WO | WO-2015/025324 A1 | 2/2015 |
| WO | WO-2016/054742 | 4/2016 |
| WO | WO-2016/071914 A1 | 5/2016 |
| WO | WO-2016/199135 A1 | 12/2016 |
| WO | WO-2018/051371 | 3/2018 |
| WO | WO-2019/003216 A1 | 1/2019 |
| WO | WO-2019/073165 | 4/2019 |
| WO | WO-2019/079335 A1 | 4/2019 |
| WO | WO-2019/220443 A1 | 11/2019 |
| WO | WO-2020/154182 | 7/2020 |

OTHER PUBLICATIONS

Pharmaseed Ltd., Author: N/A, Title: Brain and Blood PK Profile Following Intranasal Topirmate Administration—Comparison Between SipNose and Other Nasal Devices ("Pharmaseed"), pp. 1-43, with Petition in response to Patentee's observations (62 pages total), published Mar. 4, 2021 in the Register of the Opposition proceedings in EP 3400047 B1, available at https://register.epo.org/application?number=EP17711702&Ing=en&tab=doclistÐdocument E16) (last accessed Nov. 9, 2023).

Sipnose, Author: N/A, Title: Preclinical Device S1A2NP8 Batch Release Form ("SipNose"), pp. 1-2, with Petition (21 pages total), published Mar. 4, 2021 in the Register of the Opposition proceedings in EP 3400047 B1, available at https://register.epo.org/application?number=EP17711702&Ing=en&tab=doclist (last accessed Nov. 9, 2023).

Supplemental European Search Report in EP 21764082 Dtd Feb. 2, 2024.

Damm et al., "Intranasal Volume and Olfactory Function", Chemical Senses, 2002, pp. 831-839, vol. 27, Oxford University Press.

Derendorf et al., "Molecular and clinical pharmacology of intranasal corticosteroids: clinical and therapeutic implications", Allergy, 2008, pp. 1292-1300, vol. 63, 2008 Blackwell Munksgaard.

Doose et al., "Single-dose pharmacokinetics and effect of food on the bioavailability of topiramate, A novel antiepileptic drug", Journal of Clinical Pharmacology, 1996, pp. 884-891, vol. 36.

Ganger et al., "Tailoring Formulations for Intranasal Nose-to-Brain Delivery: A Review on Architecture, Physico-Chemical Characteristics and Mucociliary Clearance of the Nasal Olfactory Mucosa", Pharmaceutics, 2018, pp. 1-28, vol. 10, No. 116.

International Preliminary Report on Patentability for International Application No. PCT/IL2014/050752, dated Feb. 23, 2016.

International Search Report & International Written Opinion of the International Searching Authority issued in International Application No. PCT/IL2014/050752, dated Dec. 18, 2014.

Khan et al., "Progress in brain targeting drug delivery system by nasal route", Journal of Controlled Release, 2017, pp. 364-389, vol. 268, Elsevier B.V.

Lammi et al., "Treatment with intranasal iloprost reduces disease manifestations in a murine model of previously established COPD", The American Journal of Physiology-Lung Cellular and Molecular Physiology, 2016, pp. L630-L638, vol. 310, 2016 American Physiological Society.

Leombruni et al., "Treatment of obese patients with binge eating disorder using topiramate: a review", Neuropsychiatric Disease and Treatment, 2009, pp. 385-392, vol. 5, Dove Medical Press Ltd.

Massolt et al., "Appetite suppression through smelling of dark chocolate correlates with changes in ghrelin in young women", Regulatory Peptides, 2010, pp. 81-86, vol. 161, 2010 Elsevier B.V.

Puhakka et al., "The common cold: Effects of intranasal fluticasone propionate treatment", The Journal of Allergy and Clinical Immunology, 1998, pp. 726-731, vol. 101, No. 6, Part 1, Mosby, Inc.

Ramaekers et al., "Odors: appetizing or satiating? Development of appetite during odor exposure over time", International Journal of Obesity, 2014, pp. 650-656, vol. 38, 2014 Macmillan Publishers Limited.

Scheibe et al., "Intranasal Administration of Drugs", Archives of Otolaryngology—Head & Neck Surgery, Jun. 2008, pp. 643-646, vol. 134, No. 6, 2008 American Medical Association.

Schiffman et al., "Taste and smell perception affect appetite and immunity in the elderly", European Journal of Clinical Nutrition, 2000, pp. S54-S63, Suppl 3, 2000 Macmillan Publishers Ltd.

Schriever et al., "Size of nostril opening as a measure of intranasal volume", Physiology & Behavior, 2013, pp. 3-5, vol. 110-111, 2012 Elsevier Inc.

Yeomans, "Olfactory influences on appetite and satiety in humans", Physiology and Behavior, 2006, pp. 1-14, vol. 89, No. 1.

* cited by examiner

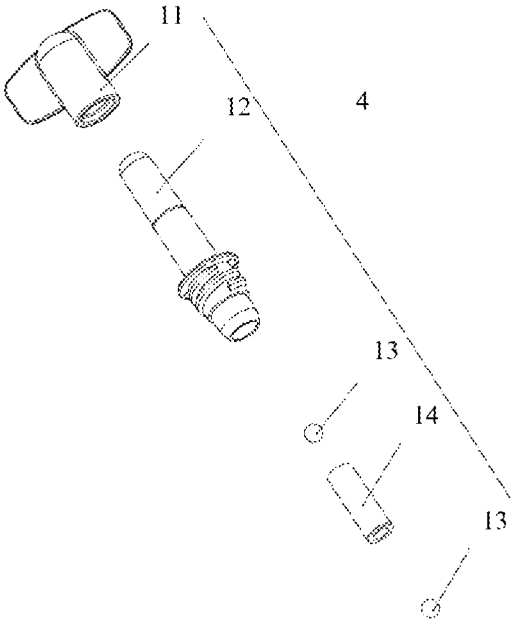
Fig. 12
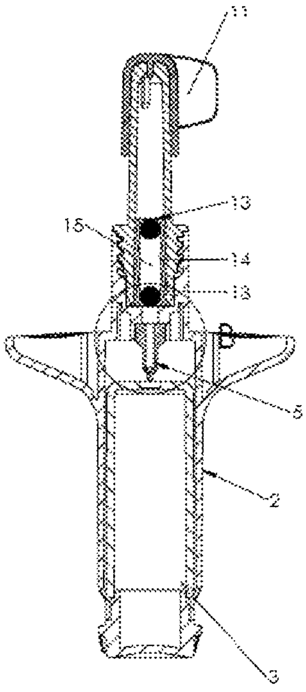
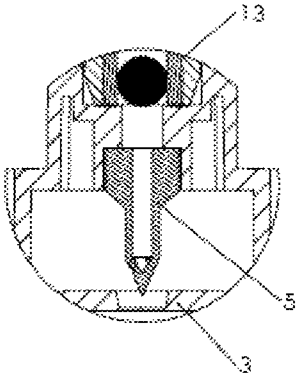
Fig. 13a Fig. 13b

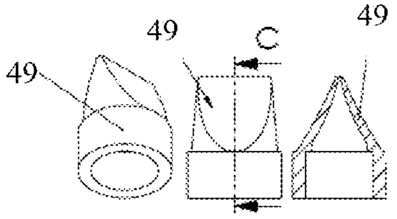
Fig. 29
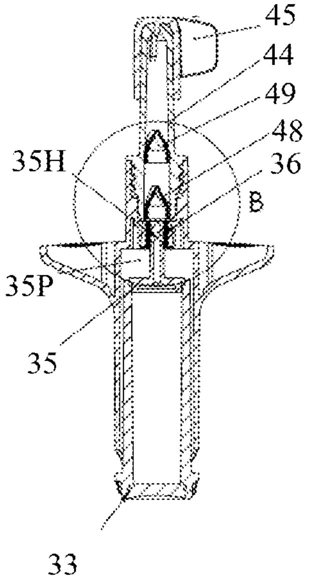
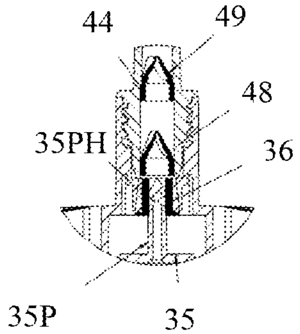
Fig. 30a Fig. 30b
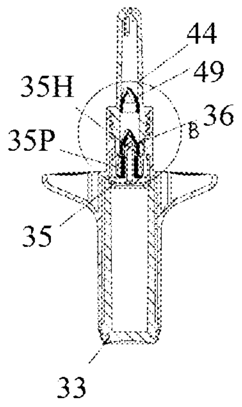
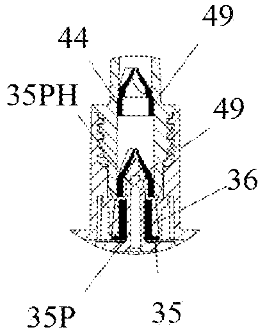
Fig. 30c Fig. 30d

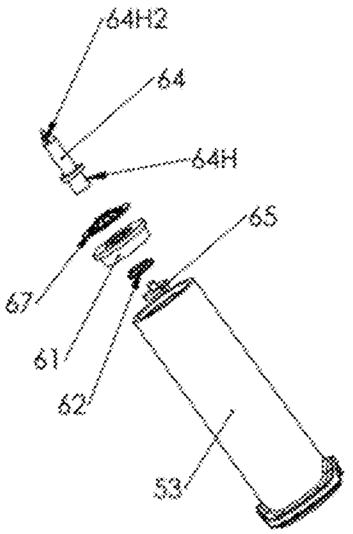
Fig. 33
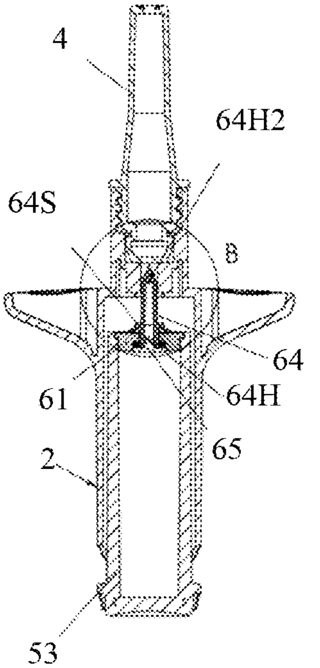
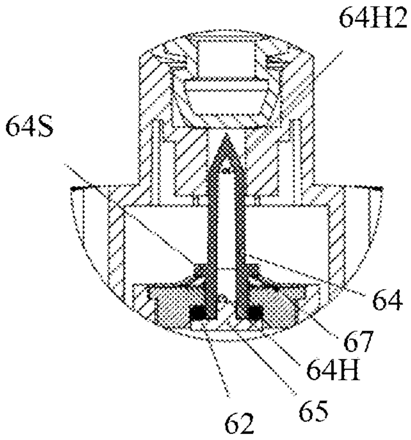
Fig. 34a Fig. 34b

DEVICES AND METHODS FOR DELIVERING A SUBSTANCE TO A BODY CAVITY

CROSS REFERENCE TO RELATED APPLICATIONS

This application is a Continuation-in-Part of U.S. application Ser. No. 16/809,994, filed on Mar. 5, 2020, which is a Continuation-in-Part of U.S. application Ser. No. 15/982,996 filed on May 17, 2018, which is a Continuation-in-Part of U.S. application Ser. No. 14/733,143 filed on Jun. 8, 2015, which claims the benefit of and priority to U.S. Provisional Application No. 62/117,986 filed on Feb. 19, 2015, and U.S. Provisional Application No. 62/077,246 filed on Nov. 9, 2014. U.S. application Ser. No. 15/982,996 claims further priority to U.S. Provisional Application No. 62/526,386 filed on Jun. 29, 2017.

U.S. application Ser. No. 16/809,994 is also a Continuation-in-Part of U.S. application Ser. No. 16/810,096 filed Mar. 5, 2020, which is a Continuation-in-Part of U.S. application Ser. No. 15/982,630 filed on May 17, 2018, which is a Continuation-in-Part of U.S. application Ser. No. 14/733,143 filed on Jun. 8, 2015, which claims the benefit of and priority to U.S. Provisional Application No. 62/117,986 filed on Feb. 19, 2015, and U.S. Provisional Application No. 62/077,246 filed on Nov. 9, 2014. U.S. application Ser. No. 15/982,630 further claims priority to U.S. Provisional Application No. 62/507,816 filed on May 18, 2017.

Further, U.S. application Ser. No. 16/809,994 is a Continuation-in-Part of U.S. application Ser. No. 14/433,048 filed on Apr. 2, 2015, which is a National Phase Entry of PCT/IL2014/050752 filed on Aug. 21, 2014, which claims the benefit of and priority to U.S. Provisional Application No. 61/868,614 filed on Aug. 22, 2013, and U.S. Provisional Application No. 61/868,627 filed on Aug. 22, 2013, and further priority to German Application No. 2020131057150 filed on Dec. 16, 2013.

Additionally, this application claims priority to and the benefit of U.S. Provisional Application No. 63/113,834 filed on Nov. 14, 2020.

This application is a Continuation-in-Part of International Application No. PCT/IB2021/051834 filed on Mar. 4, 2021.

The contents of the above applications are all incorporated by reference as if fully set forth herein in their entirety.

FIELD OF THE INVENTION

The present invention generally pertains to a system and methods for delivering aerosolized substance to a natural orifice of the body.

BACKGROUND OF THE INVENTION

Blow-Fill-Seal (BFS) technology is a manufacturing technique used to produce small (0.1 ml) and large (and up to 500 ml) liquid-filled containers. The basic concept of blow-fill-seal and form-fill-seal (referred to interchangeably hereinafter as BFS) is that a container is formed, filled and sealed in a continuous process without human intervention in a sterile or aseptic enclosed area. Thus, this technology can be used to sterile or aseptically packaging and manufacturing of pharmaceutical liquid dosage forms. Furthermore, this can be applied to any drug container (produced by any production methods) with a laminate at the bottom thereof, which can be pierced (or break) so as to deliver the medicament.

There are several ways of manufacturing. According to one method, the processes begun as pharmaceutical grade plastic resin is vertically heat-extruded through a circular throat to form a hanging tube (parison). This extruded tube is then enclosed within a two-part mold and the tube is cut above the mold. The mold is zone, or a sterile filling space, where filling needles (mandrels) are lowered and used to inflate the plastic to form a container within the mold. Following formation of the container, the mandrel is used to fill the container with the liquid. Following filling, the mandrels are retracted and a secondary top mold seals the container. All actions take place within the sterile enclosed area, a sterile shrouded chamber within the machine. The product can then be discharged to a non-sterile area for labeling, packaging and distribution.

BFS technology reduces personnel intervention, making it a more robust method for aseptic preparation of sterile pharmaceuticals. BFS is used for the filling of vials for parenteral preparations and infusion, eye drops, and inhalation products. Generally, the containers are made of polyethylene and polypropylene or any plastic resin.

It is therefore a long felt need to provide a system which provides an efficient delivery of a substance to a target site from such BFS containers, provides sufficient material to the target site, and ensures reproducibility.

SUMMARY OF THE INVENTION

It is one object of the present invention to provide a device for delivering either one or more substances within at least one body cavity, comprising:

(i) at least one nosepiece comprising at least one capsule comprising $V_{sub}$ [ml or mg] of said substances; said capsule having at least one fluid inlet port of diameter an [mm] and at least one fluid discharging outlet of diameter $D_{out}$ [mm], configured for placement in proximity to said body cavity;

(ii) at least one base in communication with said at least one nosepiece, said at least one base comprises at least one chamber configured to confine compressed and pressurized fluid at volume $V_{PF}$ [ml] and pressure $P_{PF}$ [barg];

(iii) at least one hollow puncturing member; said at least one hollow puncturing member is characterized by at least one sharp end and a second end in fluid communication with said at least one base; said first and second ends are fluidly interconnected by at least one hollow tube; said fluid inlet port of said capsule is configured by means of size and shape to interface in a sealable manner with said one sharp end of said at least one puncturing member;

wherein actuation of said base configured to enable piercing of said capsule to provide said fluid inlet port, by means of said sharp end of said puncturing member to enables the pressurized fluid to exit said chamber and entrain through said hollow tube of said hollow puncturing member to said capsule, entrain said substance and deliver the same to said body cavity.

It is another object of the present invention to provide the device as defined above, wherein said chamber is made of material being a high barrier film.

It is another object of the present invention to provide the device as defined above, wherein said a high barrier film is a high barrier Aluminum film.

It is another object of the present invention to provide the device as defined above, wherein actuation of said base is pressing on the same.

It is another object of the present invention to provide the device as defined above, wherein said second end of said at least one hollow puncturing member and said chamber are formed as a single unit, such that the upper surface of said chamber is integrated with said second end of said at least one hollow puncturing member.

It is another object of the present invention to provide the device as defined above, wherein said sharp end of said at least one hollow puncturing member comprises at least one orifice throughout which said pressurized fluid enters said capsule.

It is another object of the present invention to provide the device as defined above, additionally comprising at least one sealing septum, adapted to, prior to actuation of said base, circumference and seal said at least one orifice in said sharp end of said at least one hollow puncturing member.

It is another object of the present invention to provide the device as defined above, wherein upon actuation of said device, said at least one sealing septum is removed to enable exit of said pressurized fluid throughout said at least one orifice in said at least one hollow puncturing member.

It is another object of the present invention to provide the device as defined above, wherein upon actuation of said device, said based is pressed and said hollow puncturing member is pushed towards said nosepiece such that the bottom most part of said nosepiece removes said sealing septum from circumferencing said at least one orifice in said sharp end of said at least one hollow puncturing member.

It is another object of the present invention to provide the device as defined above, wherein said sharp end of said hollow puncturing member comprises at least one orifice, such that, once said device is actuated, said pressurized fluid enters said capsule through said at least one orifice said hollow puncturing member.

It is another object of the present invention to provide the device as defined above, wherein said chamber comprising at least one orifice throughout which said pressurized fluid exits said chamber.

It is another object of the present invention to provide the device as defined above, wherein said second end of said hollow puncturing member seals said at least one orifice of said chamber, prior to actuation of said device.

It is another object of the present invention to provide the device as defined above, wherein upon actuation of said device said sealing of said at least one orifice of said chamber is removed, such that said pressurized fluid exits through said at least one orifice of said chamber into said hollow tube of said hollow puncturing member.

It is another object of the present invention to provide the device as defined above, wherein said sharp end of said hollow puncturing member comprises at least one orifice, such that, once said device is actuated, said pressurized fluid enters said capsule through said at least one orifice said hollow puncturing member.

It is another object of the present invention to provide the device as defined above, wherein said nosepiece comprising at least one nosepiece cover configured by means of size and shape to cover, in a sealable manner, at least partially said nosepiece It is another object of the present invention to provide the device as defined above, wherein said nosepiece cover and said nosepiece are coupled to each other.

It is another object of the present invention to provide the device as defined above, wherein said coupling between nosepiece cover and said nosepiece said is reversible.

It is another object of the present invention to provide the device as defined above, wherein said nosepiece comprises at least one port throughout which said at least one substance exits said device, such that said nosepiece cover seals said at least one port and removal thereof removes said seal.

It is another object of the present invention to provide the device as defined above, wherein said capsule is selected from a group consisting of pierceable container, a blow-fill-seal and a form-fill-seal and any combination thereof.

It is another object of the present invention to provide the device as defined above, wherein said at least one chamber is a container adapted to hold said pressured fluid at said $P_{PF}$ for prolong periods of time.

It is another object of the present invention to provide the device as defined above, wherein capsule is made of at least one material selected from a group consisting of high- or low-density polyethylene, high- or low-density polypropylene, any plastic resin, glass and any combination thereof.

It is another object of the present invention to provide the device as defined above, wherein said volume $V_{PF}$ [ml] of said pressurized fluid at pressure $P_{PF}$ [barg] is released from said chamber within a short period of time, <500 milliseconds (dT), via said fluid inlet port, entrains said substances, erupts via said fluid discharging outlet port into said body cavity, such that the release time of said $V_{sub}$ [ml or mg] of said substances and said $V_{PF}$ [ml] of said pressurized fluid, $dT_{release}$ is less than 500 milliseconds.

It is another object of the present invention to provide the device as defined above, wherein said device is configured to deliver said $V_{sub}$ substance and $V_{PF}$ pressurized fluid through said fluid discharging outlet of diameter D [mm] wherein at least one of the following is held true:

a. $V_{PF}$ is in a range of 1 to 50 ml;
b. $V_{sub}$ is in a range of about 0.01 to about 7 ml;
c. $D_{in}$ and/or $D_{out}$ is in a range of 0.2 to 6 mm;
d. $P_{PF}$ is in a range of about 0 to about 10 barg;
e. said pressure velocity is greater than 0.001 barg/ms;
f. said pressure velocity is greater than 0.01 barg/ms;
g. said volume rate $dV_{sub}/dT$ or $dV_{sub}/dT_{release}$ is greater than 0.0001 ml/ms;
h. said volume rate $dV_{sub}/dT$ or $dV_{sub}/dT_{release}$ is greater than 0.001 ml/ms;
i. said volume rate $dV_{PF}/dT$ or $dV_{PF}/dT_{release}$ is greater than 0.001 ml/ms;
j. said volume rate $dV_{PF}/dT$ or $dV_{PF}/dT_{release}$ is greater than 0.01 ml/ms;
k. any combination thereof.

It is another object of the present invention to provide the device as defined above, wherein at least one of the following is true:

a. said body cavity is selected from a group consisting of nasal cavity, the mouth, the throat, an ear, the eye, the vagina, the rectum, the urethra, and any combination thereof.
b. said pressurized gas is selected from a group consisting of air, nitrogen, oxygen, carbon dioxide, helium, neon, xenon, nitric oxide and any combination thereof;
c. during dispensing of said at least one substance, a mixture of said predetermined volume $V_{gas}$ [ml] of said pressurized gas with said predetermined volume $V_{sub}$ [ml or mg] of said substance entrained within it forms a plume of aerosol; said aerosol having a predetermined distribution, said distribution being either homogeneous or heterogeneous, said heterogeneous distribution is selected from a group consisting of: an arbitrary distribution, a distribution in which the density of said at least one substance within said mixture follows a predetermined pattern, and any combination thereof; characteristics of said aerosol selected from a group consisting of: particle size, particle shape, particle distribution, and any combination thereof, are determinable from characteristics of said device selected from a group consisting of: said predetermined volume of said pressurized gas, said predetermined volume of said substance, said predetermined pressure of said pressurized gas, said predetermined orifice size, and any combination thereof;

d. at least one of said substance is selected from a group consisting of a gas, a liquid, a powder, an aerosol, a slurry, a gel, a suspension and any combination thereof;

e. at least one said substance is stored under either an inert atmosphere or under vacuum to prevent reactions during storage;

f. a dose-response curve is substantially linear for brain concentration of said substance when administered nasally via said device; and g. a dose-response curve for brain concentration having a fit selected from a group consisting of logarithmic, parabolic, exponential, sigmoid, power-low, and any combination thereof; of said substance when administered nasally via said device.

It is another object of the present invention to provide the device as defined above, wherein said nosepiece cover configured to provide an air-tight closure for said port, said port cover slidable along said device, rotatable around said device, rotatable around a hinge on the exterior of said device and any combination thereof.

It is another object of the present invention to provide the device as defined above, wherein said pressurized fluid entrains said substance in a pulsed manner, such that a plurality of potions $V_{PF}$ erupts via said fluid discharging outlet to within said body cavity It is another object of the present invention to provide the device as defined above, further comprising a safety latch, adapted to prevent accidental operation of said device.

It is another object of the present invention to provide the device as defined above, wherein said substance is selected from a group consisting of proteins; stem-cells; cells, organs, portions, extracts, and isolations thereof; macromolecules; RNA or other genes and proteins-encoding materials; neurotransmitters; receptor antagonists; hormones; Ketamine; Baqsimi product commercially available by Lilly (US); Glucagon; substrates to treat one of eth followings: anaphylaxis, Parkinson, seizures and opioid overdose; epinephrine; atropine; metoclopramide; commercially available Naloxone or Narcan products; Esketamine (Spravato); Radicava [edaravone]; Ingrezza [valbenazine]; Austedo [deutetrabenazine]; Ocrevus [ocrelizumab]; Xadago [safinamide]; Spinraza [nusinersen]; Zinbryta [daclizumab]; Nuplazid [pimavanserin]; Aristada [aripiprazole lauroxil]; Vraylar [cariprazine]; Rexulti [brexpiprazole]; Aptiom [eslicarbazepine acetate]; Vizamyl [flutemetamol F18 injection]; Brintellix [vortioxetine]; Tecfidera [dimethyl fumarate]; Dotarem [gadoterate meglumine]; Antibody mediated brain targeting drug delivery including aducanumab, gantenerumab, bapineuzumab, solanezumab, ofatumumab CD20, BIIB033, LCN2, HMGB1; insulin; oxytocin; orexin-A; leptin; benzodiazepine, midazolam; naloxone; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter, midazolam; naloxone; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, at a therapeutically effective concentration.

It is another object of the present invention to provide the device as defined above, wherein said capsule is a hollow tube characterized by at least two ends interconnect to each other, at least one of which is positioned proximal to said chamber.

It is another object of the present invention to provide the device as defined above, wherein said capsule comprises at least one spherical element positioned at least one of said ends, adapted to seal said capsule and prevent leakage of said at least one substrate therefrom.

It is another object of the present invention to provide the device as defined above, wherein said capsule comprises two spherical elements, each of which is disposed at each of said ends, such that said at least one substrate is position therebetween.

It is another object of the present invention to provide the device as defined above, wherein said two spherical elements, once said pressurized fluid exits said chamber, are adapted to mix said at least one substrate and said at least one substrate.

It is another object of the present invention to provide the device as defined above, wherein said capsule comprises at least one membrane positioned by at least one of said ends, adapted to seal said capsule and prevent leakage of said at least one substrate therefrom.

It is another object of the present invention to provide the device as defined above, wherein said capsule comprises two membranes, each of which is disposed at each of said ends, such that said at least one substrate is position therebetween.

It is another object of the present invention to provide the device as defined above, wherein said capsule comprises at least one duckbill valve positioned by at least one of said ends, adapted to seal said capsule and prevent leakage of said at least one substrate therefrom.

It is another object of the present invention to provide the device as defined above, wherein said capsule comprises two duckbill valves, each of which is disposed at each of said ends, such that said at least one substrate is position therebetween.

It is another object of the present invention to provide the device as defined above, wherein said capsule comprises at least one spherical element, membrane, uni-directional valve, duckbill valve and any combination thereof.

It is another object of the present invention to provide a method for delivering either one or more substances within at least one body cavity, characterized by steps of a. providing:

i. at least one nosepiece comprising at least one capsule comprising $V_{sub}$ [ml or mg] of said substances; said capsule having at least one fluid inlet port of diameter $D_{in}$ [mm] and at least one fluid discharging outlet of diameter $D_{out}$ [mm], configured for placement in proximity to said body cavity;

ii. at least one base in communication with said at least one nosepiece, said at least one base comprises at least one chamber configured to confine compressed and pressurized fluid at volume $V_{PF}$ [ml] and pressure $P_{PF}$ [barg];

iii. at least one hollow puncturing member; said at least one hollow puncturing member is characterized by at least one sharp end and a second end in fluid communication with said at least one base; said first and second ends are fluidly interconnected by at least one hollow tube; said fluid inlet port of said capsule is configured by means of size and shape to interface in a sealable manner with said one end of said at least one puncturing member;

b. actuating said base thereby piercing of said capsule in said nosepiece, by means of said at least one puncturing member.

It is another object of the present invention to provide the method as defined above, wherein said chamber is made of material being a high barrier film.

It is another object of the present invention to provide the method as defined above, wherein said high barrier film is a high barrier Aluminum film.

It is another object of the present invention to provide the method as defined above, wherein step (b) of actuating said base additionally comprising pressing said base.

It is another object of the present invention to provide the method as defined above, wherein step (b) of actuating said base enables the pressurized fluid to exit said chamber and entrain through said hollow tube of said hollow puncturing member to said capsule, entrain said substance and deliver the same to said body cavity.

It is another object of the present invention to provide the method as defined above, wherein step (b) of actuating said base results in releasing said volume $V_{PF}$ [ml] of said pressurized fluid at pressure $P_{PF}$ [barg] within a short period of time, <500 milliseconds (dT); out of said chamber, via said fluid inlet thereby entraining said substances and erupting via said fluid discharging outlet into said body cavity, such that the release time of said $V_{sub}$ [ml or mg] of said substances and said $V_{PF}$ [ml] of said pressurized fluid, $dT_{release}$ is less than 500 milliseconds.

It is another object of the present invention to provide the method as defined above, wherein said second end of said at least one hollow puncturing member and said chamber are formed as a single unit, such that the upper surface of said chamber is integrated with said second end of said at least one hollow puncturing member.

It is another object of the present invention to provide the method as defined above, wherein said sharp end of said at least one hollow puncturing member comprises at least one orifice throughout which said pressurized fluid enters said capsule.

It is another object of the present invention to provide the method as defined above, wherein said device additionally comprising at least one sealing septum, adapted to, prior to actuation of said base, circumference and seal said at least one orifice in said sharp end of said at least one hollow puncturing member.

It is another object of the present invention to provide the method as defined above, wherein upon actuation of said device, said at least one sealing septum is removed to enable exit of said pressurized fluid throughout said at least one orifice in said at least one hollow puncturing member.

It is another object of the present invention to provide the method as defined above, wherein upon actuation of said device, said based is pressed and said hollow puncturing member is pushed towards said nosepiece such that the bottom most part of said nosepiece removes said sealing septum from circumferencing said at least one orifice in said sharp end of said at least one hollow puncturing member.

It is another object of the present invention to provide the method as defined above, wherein said sharp end of said hollow puncturing member comprises at least one orifice, such that, once said device is actuated, said pressurized fluid enters said capsule through said at least one orifice said hollow puncturing member It is another object of the present invention to provide the method as defined above, wherein said chamber comprising at least one orifice throughout which said pressurized fluid exits said chamber.

It is another object of the present invention to provide the method as defined above, wherein said second end of said hollow puncturing member seals said at least one orifice of said chamber, prior to actuation of said device.

It is another object of the present invention to provide the method as defined above, wherein upon actuation of said device said sealing of said at least one orifice of said chamber is removed, such that said pressurized fluid exits through said at least one orifice of said chamber into said hollow tube of said hollow puncturing member.

It is another object of the present invention to provide the method as defined above, wherein said sharp end of said hollow puncturing member comprises at least one orifice, such that, once said device is actuated, said pressurized fluid enters said capsule through said at least one orifice said hollow puncturing member.

It is another object of the present invention to provide the method as defined above, wherein said nosepiece comprising at least one nosepiece cover configured by means of size and shape to cover, in a sealable manner, at least partially said nosepiece It is another object of the present invention to provide the method as defined above, wherein said nosepiece comprising at least one nosepiece cover and said nosepiece are coupled to each other.

It is another object of the present invention to provide the method as defined above, wherein said coupling between nosepiece cover and said nosepiece said is reversible.

It is another object of the present invention to provide the method as defined above, wherein removal of said nosepiece cover results in piercing said capsule to provide said fluid discharging outlet.

It is another object of the present invention to provide the method as defined above, wherein removal of said nosepiece cover is obtained by at least one action selected from a group consisting of sliding said nosepiece cover along said device, rotating said nosepiece cover around said device, rotating said nosepiece cover around a hinge on the exterior of said device and any combination thereof.

It is another object of the present invention to provide the method as defined above, wherein said nosepiece cover comprises at least one nosepiece puncturing member adapted to pierce said capsule to enable said fluid discharging outlet.

It is another object of the present invention to provide the method as defined above, wherein said nosepiece comprises at least one port throughout which said at least one substance exits said device, such that said nosepiece cover seals said at least one port and removal thereof removes said seal.

It is another object of the present invention to provide the method as defined above, wherein said capsule is selected from a group consisting of pierceable container, a blow-fill-seal and a form-fill-seal and any combination thereof.

It is another object of the present invention to provide the method as defined above, wherein said at least one chamber is a container adapted to hold said pressured fluid at said $P_{PF}$ for prolong periods of time.

It is another object of the present invention to provide the method as defined above, wherein capsule is made of at least one material selected from a group consisting of high- or low-density polyethylene, high- or low-density polypropylene, any plastic resin, glass and any combination thereof.

It is another object of the present invention to provide the method as defined above, wherein said device is configured to deliver said $V_{sub}$ substance and $V_{PF}$ pressurized fluid through said fluid discharging outlet of diameter D [mm] wherein at least one of the following is held true:

a. $V_{PF}$ is in a range of 1 to 50 ml;
b. $V_{sub}$ is in a range of about 0.01 to about 7 ml;
c. $D_{in}$ and/or $D_{out}$ is in a range of 0.2 to 6 mm;
d. $P_{PF}$ is in a range of about 0 to about 10 barg;
e. said pressure velocity is greater than 0.001 barg/ms;
f. said pressure velocity is greater than 0.01 barg/ms;
g. said volume rate $dV_{sub}/dT$ or $dV_{sub}/dT_{release}$ is greater than 0.0001 ml/ms;
h. said volume rate $dV_{sub}/dT$ or $dV_{sub}/dT_{release}$ is greater than 0.001 ml/ms;
i. said volume rate $dV_{PF}/dT$ or $dV_{PF}/dT_{release}$ is greater than 0.001 ml/ms;
j. said volume rate $dV_{PF}/dT$ or $dV_{PF}/dT_{release}$ is greater than 0.01 ml/ms; and
k. any combination thereof.

It is another object of the present invention to provide the method as defined above, additionally comprising at least one of the following steps:

a. selecting said body cavity from a group consisting of a nasal cavity, the mouth, the throat, an ear, the eye, the vagina, the rectum, the urethra, and any combination thereof;
b. selecting said gas from a group consisting of: air, nitrogen, oxygen, carbon dioxide, helium, neon, xenon, nitric oxide and any combination thereof;
c. dispensing said at least one substance, and during said step of dispensing, forming a plume of aerosol with predetermined distribution from a mixture of said predetermined volume $V_{gas}$ [ml] of said pressurized gas and said predetermined volume $V_{sub}$ [ml or mg] entrained within it; selecting said predetermined distribution from a group consisting of: a homogeneous distribution, a heterogeneous distribution; selecting said heterogeneous distribution from a group consisting of: an arbitrary distribution, a distribution in which the density of said at least one substance within said mixture follows a predetermined pattern, and any combination thereof; selecting characteristics of said aerosol from a group consisting of: particle size, particle shape, particle distribution, and any combination thereof, are determinable from characteristics of said device selected from a group consisting of: said predetermined volume of said pressurized gas, said predetermined volume of said substance, said predetermined pressure of said pressurized gas, said predetermined orifice size, and any combination thereof;
d. selecting said substance from a group consisting of: a gas, a liquid, a powder, a slurry, a gel, a suspension, and any combination thereof
e. storing at least one said substance under either an inert atmosphere or under vacuum, thereby preventing reactions during storage; and f. characterizing a dose-response curve for brain concentration of said substance to be of substantially linear form; and
g. a dose-response curve for brain concentration having a fit selected from a group consisting of logarithmic, parabolic, exponential, sigmoid, power-low, and any combination thereof; of said substance when administered nasally via said device.

It is another object of the present invention to provide the method as defined above, wherein said substance is selected from a group consisting of proteins; stem-cells; cells, organs, portions, extracts, and isolations thereof; macromolecules; RNA or other genes and proteins-encoding materials; neurotransmitters; receptor antagonists; hormones; Ketamine; Baqsimi product commercially available by Lilly (US); Glucagon; substrates to treat one of eth followings: anaphylaxis, Parkinson, seizures and opioid overdose; epinephrine; atropine; metoclopramide; commercially available Naloxone or Narcan products; Esketamine (Spravato); Radicava [edaravone]; Ingrezza [valbenazine]; Austedo [deutetrabenazine]; Ocrevus [ocrelizumab]; Xadago [safinamide]; Spinraza [nusinersen]; Zinbryta [daclizumab]; Nuplazid [pimavanserin]; Aristada [aripiprazole lauroxil]; Vraylar [cariprazine]; Rexulti [brexpiprazole]; Aptiom [eslicarbazepine acetate]; Vizamyl [flutemetamol F18 injection]; Brintellix [vortioxetine]; Tecfidera [dimethyl fumarate]; Dotarem [gadoterate meglumine]; Antibody mediated brain targeting drug delivery including aducanumab, gantenerumab, bapineuzumab, solanezumab, ofatumumab CD20, BIIB033, LCN2, HMGB1; insulin; oxytocin; orexin-A; leptin; benzodiazepine i.e. midazolam; naloxone; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, at a therapeutically effective concentration.

It is another object of the present invention to provide the method as defined above, wherein said puncturing member comprising a plurality of holes throughout which said pressurized fluid exits said chamber and entrains said substance, after activation of said activation mechanism.

It is another object of the present invention to provide the method as defined above, wherein said capsule is a hollow tube characterized by at least two ends interconnect to each other, at least one of which is positioned proximal to said chamber.

It is another object of the present invention to provide the method as defined above, wherein said capsule comprises at least one spherical element positioned by at least one of said ends, adapted to seal said capsule and prevent leakage of said at least one substrate therefrom.

It is another object of the present invention to provide the method as defined above, wherein said capsule comprises two spherical elements, each of which is disposed at each of said ends, such that said at least one substrate is position therebetween.

It is another object of the present invention to provide the method as defined above, wherein said two spherical elements, once said pressurized fluid exits said chamber, are adapted to mix said at least one substrate and said at least one substrate.

It is another object of the present invention to provide the method as defined above, wherein said capsule comprises at least one membrane positioned at at least one of said ends, adapted to seal said capsule and prevent leakage of said at least one substrate therefrom.

It is another object of the present invention to provide the method as defined above, wherein said capsule comprises two membranes, each of which is disposed at each of said ends, such that said at least one substrate is position therebetween.

It is another object of the present invention to provide the method as defined above, wherein said capsule comprises at least one duckbill valve positioned at at least one of said ends, adapted to seal said capsule and prevent leakage of said at least one substrate therefrom.

It is another object of the present invention to provide the method as defined above, wherein said capsule comprises two duckbill valves, each of which is disposed at each of said ends, such that said at least one substrate is position therebetween.

It is another object of the present invention to provide the method as defined above, wherein said capsule comprises at least one spherical element, membrane, uni-directional valve, duckbill valve and any combination thereof.

It is another object of the present invention to provide the method as defined above, wherein said at least one hollow puncturing member comprises at least one orifice throughout which said pressurized fluid enters said hollow puncturing member.

It is another object of the present invention to provide the method as defined above, wherein, once said device is actuated, said pressurized fluid exit said chamber and enters said hollow puncturing member through said at least one orifice.

It is another object of the present invention to provide the method as defined above, wherein said at least one hollow puncturing member comprises at least one orifice throughout which said pressurized fluid enters said hollow puncturing member.

It is another object of the present invention to provide the method as defined above, wherein, once said device is actuated, said pressurized fluid exit said chamber and enters said hollow puncturing member through said at least one orifice.

It is another object of the present invention to provide the method as defined above, wherein said chamber is comprised of at least one material selected from a group consisting of high- or low-density polyethylene, high- or low-density polypropylene, any plastic resin, glass, plastics, Aluminum and any combination thereof.

It is another object of the present invention to provide the method as defined above, wherein said chamber is comprised of at least one material selected from a group consisting of high- or low-density polyethylene, high- or low-density polypropylene, any plastic resin, glass, plastics, Aluminum and any combination thereof.

It is an object of the present invention to disclose a device for delivering either one or more substances within at least one body cavity. The device is characterized by at least one pierceable vial comprising $V_{sub}$ [ml or mg] of the substances; the vial having at least one fluid inlet port of diameter $D_{in}$ [mm] and at least one fluid discharging outlet port of diameter $D_{out}$ [mm], configured for placement in proximity to the body cavity; the fluid inlet port configured by means of size and shape to interface with at least one puncturing member, configured to, upon coupling to the fluid inlet port, piercing the same, thereby providing the substances in a fluid communication, with at least one chamber configured to accept pressurized fluid at volume $V_{PF}$ [ml] and pressure $P_{PF}$ [barg]; the pressurized fluid flows from the chamber, via the fluid inlet port, entrains the substances, erupts via the fluid discharging outlet port to within the body cavity in the form of aerosol, such that the release time of the $V_{sub}$ [ml or mg] of the substances and the $V_{PF}$ [ml] of the pressurized fluid, $dT_{release}$ is less than 500 milliseconds; In this device, the following held: $V_{PF}$ is in a range of 1 to 50 ml; $V_{sub}$ is in a range of about 0.01 to about 7 ml or 0.1 mg to 7 g; $P_{PF}$ is in a range of about 0 to about 10 barg; further wherein at least one of the following is being held true: $D_{in}$ or $D_{out}$ are in a range of 0.2 to 6 mm; the pressure velocity is greater than 0.001 barg/ms; the pressure velocity is greater than 0.01 barg/ms; the volume rate $dV_{sub}/dT_{release}$ is greater than 0.0001 ml/ms; the volume rate $dV_{sub}/dT_{release}$ is greater than 0.001 ml/ms; the volume rate $dV_{PF}/dT_{release}$ is greater than 0.001 ml/ms; the volume rate $dV_{PF}/dT_{release}$ is greater than 0.01 ml/ms; any combination thereof. The vial is further selected from a group consisting of a pierceable container, a blow-fill-seal and a form-fill-seal and any combination thereof.

It is another of the present invention to disclose the device as disclosed above, wherein the vial comprises a cap adapted to seal the vial, such that removal thereof provides fluid communication between the vial and the body cavity through the fluid discharging outlet port.

It is another of the present invention to disclose the device as disclosed in any of the above, wherein the at least one puncturing member is adapted to pierce the vial be means of a screw mechanism, such that rotation of the nosepiece cover along the screw mechanism in the base enables the pierce of the fluid inlet port in the vial by means of the puncturing member.

It is another of the present invention to disclose the device as defined in any of the above, wherein at least one of the following is true: (a) The body cavity is selected from a group consisting of nasal cavity, the mouth, the throat, an ear, the eye, the vagina, the rectum, the urethra, and any combination thereof. (b) The pressurized gas is selected from a group consisting of air, nitrogen, oxygen, carbon dioxide, helium, neon, xenon, nitric oxide and any combination thereof. (c) During dispensing of the at least one substance, a mixture of the predetermined volume $V_{gas}$ [ml] of the pressurized gas with the predetermined volume $V_{sub}$ [ml or mg] of the substance entrained within it forms a plume of aerosol; the aerosol having a predetermined distribution, the distribution being either homogeneous or heterogeneous, the heterogeneous distribution is selected from a group consisting of: an arbitrary distribution, a distribution in which the density of the at least one substance within the mixture follows a predetermined pattern, and any combination thereof; characteristics of the aerosol selected from a group consisting of: particle size, particle shape, particle distribution, and any combination thereof, are determinable from characteristics of the device selected from a group consisting of: the predetermined volume of the pressurized gas, the predetermined volume of the substance, the predetermined pressure of the pressurized gas, the predetermined orifice size, and any combination thereof (d) At least one the substance is selected from a group consisting of a gas, a liquid, a powder, an aerosol, a slurry, a gel, a suspension and any combination thereof. (e) The least one the substance is stored under either an inert atmosphere or under vacuum to prevent reactions during storage. (f) A dose-response curve is substantially linear for brain concentration of the substance when administered nasally via the device; and (g) A dose-response curve for brain concentration having a fit selected from a group consisting of logarithmic, parabolic, exponential, sigmoid, power-low, and any combination thereof; of the substance when administered nasally via the device.

It is another of the present invention to disclose the device as disclosed in any of the above, wherein the vial is a capsule having a main longitudinal axis, the capsule comprising a number n of compartments, the capsule configured to contain the predetermined volume $V_{sub}$ [ml or mg] of the at least one substance, the volume $V_{sub}$ [ml or mg] of the at least one substance containable in at least one of the n compartments; at least one of the following being true: the number n of the compartments is an integer greater than or equal to 1; at least one the compartment has cross-section with shape selected from a group consisting of: wedge shaped, circular, oval, elliptical, polygonal, annular, and any combination thereof; for the number n of compartments being an integer greater than 1, at least two the compartments have different volumes; for the number n of compartments being an integer greater than 1, at least two the compartments have the same volume; for the number n of compartments being an integer greater than 1, at least two the compartments have different cross-sectional areas; for the number n of compartments being an integer greater than 1, at least two the compartments have the same cross-sectional area; for the number n of compartments being an integer greater than 1, at least two the compartments contain different substances; for the number n of compartments being an integer greater than 1, at least two the compartments contain the same substance; for the number n of compartments being an integer greater than 1, at least two the compartments are disposed coaxially around the main longitudinal axis of the capsule; for the number n of compartments being an integer greater than 1, at least two the compartments are disposed sequentially along the main longitudinal axis of the capsule; for the number n of compartments greater than 1, the plurality of substances mix during the dispensing; and for the number n of compartments greater than 1, the plurality of substances react during the dispensing.

It is another of the present invention to disclose the device as disclosed in any of the above, wherein the vial comprises a port fluidly connectable to the exterior of the device, the port configured such that the at least one substance is insertable into the chamber via the port.

It is another object of the present invention to disclose the device as disclosed above, wherein the device comprises a port cover configured to provide an air-tight closure for the port, the port cover slidable along the device, rotatable around the device, rotatable around a hinge on the exterior of the device and any combination thereof.

It is another of the present invention to disclose the device as disclosed in any of the above, wherein the pressurized fluid entrains the substance in a pulsed manner, such that a plurality of potions $V_{PF}$ erupts via the fluid discharging outlet to within the body cavity It is another object of the present invention to disclose a method for delivering either one or more substances within at least one body cavity, characterized by steps of providing at least one pierceable vial with $V_{sub}$ [ml or mg] of the substances; the vial having at least one fluid inlet port of diameter $D_{in}$ [mm] and at least one fluid discharging outlet port of diameter $D_{out}$ [mm], configured for placement in proximity to the body cavity; configuring the fluid inlet by means of size and shape to interface a puncturing member, so that upon coupling to the fluid inlet port, piercing of the same, thereby providing the substances in a fluid communication, with at least one chamber configured to accept pressurized fluid at volume $V_{PF}$ [ml] and pressure $P_{PF}$ [barg]; and facilitating the flow of the pressurized fluid from the chamber, via the fluid inlet, entrains the substances, erupts via the fluid discharging outlet port into the body cavity, such that the release time of the $V_{sub}$ [ml or mg] of the substances and the $V_{PF}$ [ml] of the pressurized fluid, $dT_{release}$ is less than 500 milliseconds. The method further held the followings: $V_{PF}$ is in a range of 1 to 50 ml; $V_{sub}$ is in a range of about 0.01 to about 7 ml or 0.1 mg to 1 g; $P_{PF}$ is in a range of about 0 to about 10 barg/The following is further being held true: $D_{in}$ or $D_{out}$ are in a range of 0.2 to 6 mm; the pressure velocity is greater than 0.001 barg/ms; the pressure velocity is greater than 0.01 barg/ms; the volume rate or $dV_{sub}/dT_{release}$ is greater than 0.0001 ml/ms; the volume rate $dV_{sub}/dT_{release}$ is greater than 0.001 ml/ms; the volume rate $dV_{PF}/dT_{release}$ is greater than 0.001 ml/ms; the volume rate $dV_{PF}/dT_{release}$ is greater than 0.01 ml/ms; and any combination thereof. Additionally, the step of providing the vial additionally comprising step of selecting the vial from a group consisting of a pierceable container, a blow-fill-seal and a form-fill-seal and any combination thereof.

It is another of the present invention to disclose the method as disclosed above, wherein it additionally comprising at least one of the following steps: selecting the body cavity from a group consisting of a nasal cavity, the mouth, the throat, an ear, the eye, the vagina, the rectum, the urethra, and any combination thereof; selecting the gas from a group consisting of: air, nitrogen, oxygen, carbon dioxide, helium, neon, xenon, nitric oxide and any combination thereof; dispensing the at least one substance, and during the step of dispensing, forming a plume of aerosol with predetermined distribution from a mixture of the predetermined volume $V_{gas}$ [ml] of the pressurized gas and the predetermined volume $V_{sub}$ [ml] entrained within it; selecting the predetermined distribution from a group consisting of: a homogeneous distribution, a heterogeneous distribution; selecting the heterogeneous distribution from a group consisting of: an arbitrary distribution, a distribution in which the density of the at least one substance within the mixture follows a predetermined pattern, and any combination thereof; selecting characteristics of the aerosol from a group consisting of: particle size, particle shape, particle distribution, and any combination thereof, are determinable from characteristics of the device selected from a group consisting of: the predetermined volume of the pressurized gas, the predetermined volume of the substance, the predetermined pressure of the pressurized gas, the predetermined orifice size, and any combination thereof;

selecting the substance from a group consisting of: a gas, a liquid, a powder, a slurry, a gel, a suspension, and any combination thereof; storing at least one the substance under either an inert atmosphere or under vacuum, thereby preventing reactions during storage; and characterizing a dose-response curve for brain concentration of the substance to be of substantially linear form; and a dose-response curve for brain concentration having a fit selected from a group consisting of logarithmic, parabolic, exponential, sigmoid, power-low, and any combination thereof; of the substance when administered nasally via the device.

BRIEF DESCRIPTION OF THE DRAWINGS

The invention is herein described, by way of example only, with reference to the accompanying drawings, wherein:

FIG. 5G showing the device after activation;

FIG. 6B showing securing of the BFS to the device and breaking the cap; FIG. 6C presenting a cross-section view; FIG. 6D showing a button at the base of the device being pushed; FIG. 6E showing pressurized fluid flowing from the container to the BFS and carrying the drug outward;

FIGS. 10-19 show another embodiment of the present invention.

FIGS. 25-30*d* show another embodiment of the present invention.

FIGS. 33-34*d* show another embodiment of the present invention.

DETAILED DESCRIPTION OF THE PREFERRED EMBODIMENTS

Figure 1A:
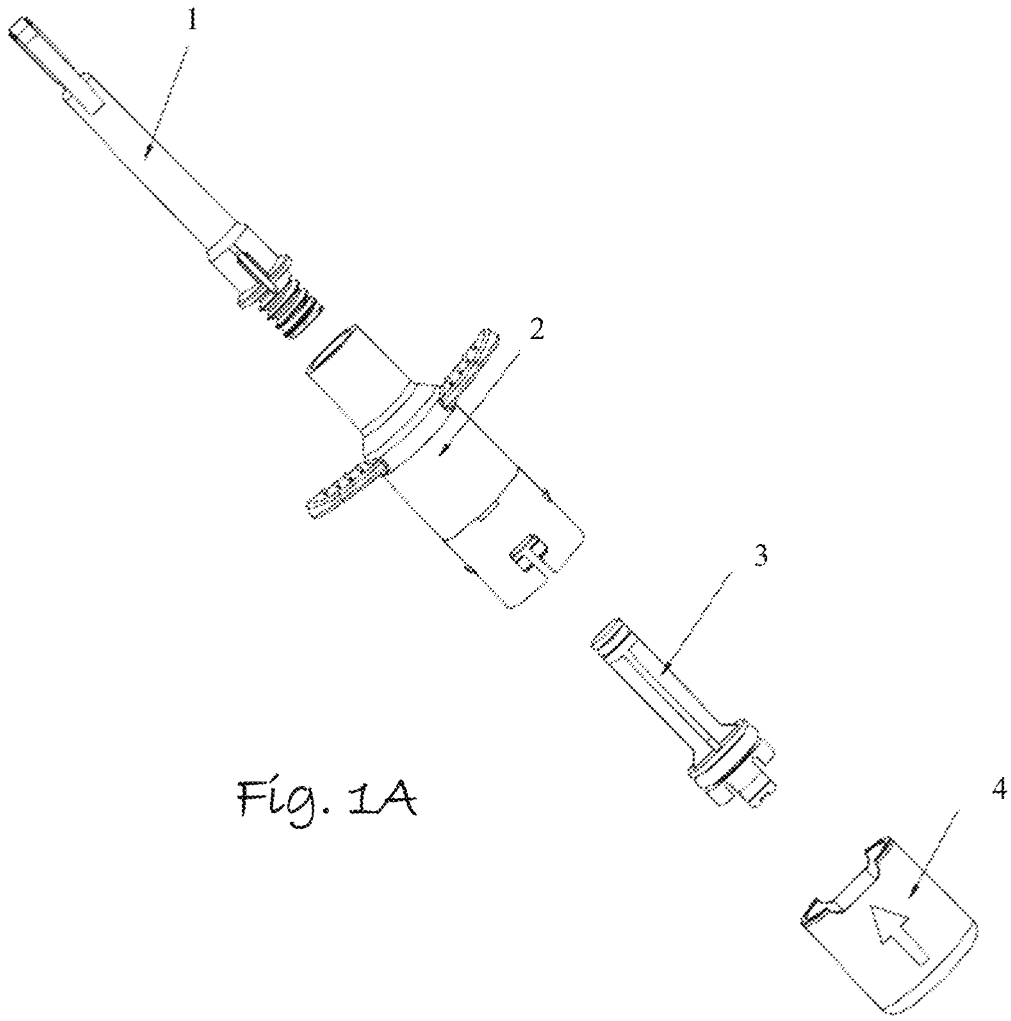
FIGS. 1A-B shows an embodiment of the present invention, with FIG. 1A showing an exploded view of the device and FIG. 1B showing the device fully assembled.

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a device capable of improving the transfer of medicament to a predetermined desired location and to provide a device capable of improving the delivery of medicament through the tissue.

In the present invention, a combination of parameters and forces such as pressure, gas/air volume orifice diameter enable the formation of optimized aerosol characteristics for both improved delivery of aerosol to the target area (such as the olfactory epithelium in the nasal cavity) and enhanced absorption at that area for better delivery to a desired tissue (such as the brain).

The term 'high barrier films' hereinafter refers to any materials in flexible packaging laminations that prevent the permeation of water, water vapor, oil, oxygen, aroma, flavor, gas, or light. Such provision is enabled by low permeability of the film. In some embodiments the film is made of high-density Aluminum films. Thus, according to one embodiment of the present invention, the pressurized gas enclosed within a high barrier film that can maintain the pressure of the compressed gas for prolong period of times without leakage therefrom.

The term 'ul' or 'μm' hereinafter refers to the unit micro liters or micro meters, respectively.

The term 'capsule' interchangeably 'container' interchangeably refer to a container configured to contain a flowable substance. The term flowable refers hereinafter to any liquid, gas, aerosol, powder and any combination thereof. It should be emphasized that the term capsule can also refer to a predefined volume within the same in which a flowable substance is placed. In other words, the predefined volume is sized and shaped to enclose a predefined volume of the sub stance.

The term 'plurality' hereinafter refers to an integer greater than or equal to one.

The term 'olfactory epithelium' hereinafter refers to a specialized epithelial tissue inside the nasal cavity. The olfactory epithelium lies in the upper top portion of the nasal cavity.

The term 'substance' hereinafter refers to any substance capable of flowing. Such a substance can be a granular material, including a powder; a liquid; a gel; a slurry; a suspension; and any combination thereof. The term further refers to one or more members of a group consisting of proteins; stem-cells; cells, organs, portions, extracts, and isolations thereof; macro-molecules; RNA or other genes and proteins-encoding materials; neurotransmitters; receptor antagonists; biologic response modifiers; hormones; Ketamine; commercially available by Lilly (US) Baqsimi product; Glucagon, biologic response modifiers; Glucagon; substrates to treat one of eth followings: anaphylaxis, Parkinson, seizures and opioid overdose; epinephrine; atropine; metoclopramide; commercially available Naloxone or Narcan products; Esketamine (Spravato); Radicava [edaravone]; Ingrezza [valbenazine]; Austedo [deutetrabenazine]; Ocrevus [ocrelizumab]; Xadago [safinamide]; Spinraza [nusinersen]; Zinbryta [daclizumab]; Nuplazid [pimavanserin]; Aristada [aripiprazole lauroxil]; Vraylar [cariprazine]; Rexulti [brexpiprazole]; Aptiom [eslicarbazepine acetate]; Vizamyl [flutemetamol F18 injection]; Brintellix [vortioxetine]; Tecfidera [dimethyl fumarate]; Dotarem [gadoterate meglumine]; Antibody mediated brain targeting drug delivery including aducanumab, gantenerumab, bapineuzumab, solanezumab, ofatumumab CD20, BIIB033, LCN2, HMGB1; insulin; oxytocin; orexin-A; leptin; benzodiazepine i.e. midazolam; naloxone; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, at a therapeutically effective concentration.

The term 'gas' refers to any fluid that can be readily compressed. Gases as used herein include, but are not limited to, air, nitrogen, oxygen, carbon dioxide, helium, neon, xenon, nitric oxide and any combination thereof. Devices charged by hand will typically use air as the carrier gas.

The term 'fluid' refers to any substance or mixtures of substances that continually deforms (flows) under an applied shear stress, or external force. This term refers to gas, liquids, particulate or granulated solids (powders), aerosols, and any mixtures and combinations thereof.

The term 'about' refers hereinafter to a range of 25% below or above the referred value.

The term "body orifice" and "body cavity" are interchangeably refer to one or more of the followings: nasal cavity, a mouth, a throat, an ear, the eye, a vagina, a rectum, a urethra, and any combination thereof.

The term 'biologic' or 'biologic response modifier' hereinafter refers to material manufactured in or extracted from biological sources such as a genetically engineered protein derived from human genes, or a biologically effective combination of such proteins.

All pressures herein are gauge pressures, relative to atmospheric pressure. Pressure units will be written herein using the standard abbreviation for "gauge", namely, "g". For example, atmospheric pressure is 0 barg and a pressure of 1 bar above atmospheric is 1 barg.

The term 'release time' refers hereinafter to the time for the drug and carrier gas to substantially completely exit the device. Typically, the release time is affected by the combination of the Volume of substance, volume of pressurized gas, pressure of pressurized gas, the orifice diameter, the activation time of the valve that reflects the time for the device to reconfigure from the ACTIVE configuration to the INACTIVE configuration or vice versa and any combination thereof.

The terms 'the device', 'the present device', 'the SipNose device' and 'SipNose' will be used interchangeably to refer to a device according to any embodiment of the present invention.

In all of the embodiments of the device shown hereinbelow, identical numbers refer to identical functions. All figures shown herein are illustrative and none is to scale.

The present invention teaches a device for delivering a predetermined amount of a substance, preferably comprising a medication or combination of medications, into a body orifice of a subject, the orifice comprising any of the body's natural orifices, including a nostril, the mouth, the ear, the throat, the urethra, the eye, the vagina, the rectum and any combination thereof.

In preferred embodiments of the device, the device comprises a delivery mechanism and a medicament capsule, as described hereinbelow. The device can apply a broad range of drugs and materials to the nasal cavity for local effect, deliver a broad range of drugs and materials through the nasal cavity to the systemic circulation, deliver a broad range of drugs and materials through the nasal cavity to the central nerve system (CNS) the brain, spinal cord and associated nerves, and any combination thereof.

The drugs to be applied could be, but are not limited to, pharmaceuticals, natural compounds, biologics, hormones, peptides, proteins, viruses, cells, stem cells and any combination thereof.

However, it should be emphasized that the device can be provided alone as well as in combination with a capsule.

In some cases, the capsule would be provided with a known medicament within the same and in other cases the capsule would be 'filled' with the medicament just before use.

In some embodiments of the present invention, the device operating characteristics and the substance characteristics can be jointly optimized to maximize uptake of the substance at the desired site. In preferred variants of such embodiments, uptake is further optimized by exploiting synergies between delivery characteristics generated by the device and by the formulation or composition of the delivered material In some embodiments, the substance comprises one or more agents to optimize delivery through the mucosal membrane by means of mucoadhesive agent and/or a permeability enhancer agent and/or a particulate formulation in the nano-particle or macro-particle range, and any combination thereof. In such embodiments, the combination of the device and substance enhance the delivery of the active agent to the target area (nasal epithelium and more specifically olfactory epithelium) and from there to the target tissue (for example the brain).

A non-limiting example is a composition comprising a drug to be delivered and at least one chemical permeation enhancer (CPE). In a preferred embodiment, the composition contains two or more CPEs which, by using a nasal delivery device, affect in an additive manner or behave synergistically to increase the permeability of the epithelium, while providing an acceptably low level of cytotoxicity to the cells. The concentration of the one or more CPEs is selected to provide the greatest amount of overall potential (OP). Additionally, the CPEs are selected based on the treatment. CPEs that behave primarily by transcellular transport are preferred for delivering drugs into epithelial cells. CPEs that behave primarily by paracellular transport are preferred for delivering drugs through epithelial cells. Also provided herein are mucoadhesive agents that enable the extension of the exposure period of the target tissue/mucus membrane to the active agent, for the enhancement of delivery of the active agent to and through the mucus membrane.

In contrast to prior-art nasal delivery devices and technologies, the devices of the present invention can produce a fine aerosol in the nasal cavity or other desired body orifice at the target area and at the location of the target tissue instead of producing the aerosol only within the device or immediately after exit from the device. Utilizing the pressure as a driving force and the air as a carrier allows the material to be released from the nozzle as a mixture of aerosol and a pre-aerosolized state. The properties of the resultant aerosol are typically dependent on the properties of the device and of the medium into which the device is discharged. The properties of the device which affect the aerosol characteristics are the delivery pressure, the volume of the delivery gas, the characteristics of its orifice and time of activate.

In some embodiments, the aerosol properties are fairly independent of the delivered substance, while, in other embodiments, the pressure, volume, orifice characteristics, and delivered substance properties can be co-optimized.

In prior-art devices the aerosol is produced in proximity exit of the device. Typically, the aerosol comprises a wide "fan" of aerosol and a low driving force. Therefore, large droplets typically deposit very close to the exit from the device, while smaller droplets tend to quickly contact the walls of the passage, so that deposition is typically predominantly close to the delivery end of the device, with little of the substance reaching desired sites deeper in the body orifice, such as the middle and superior turbinates of the nose. In the present invention the aerosol created, due to the pressurized air carrier, reaches the upper regions of the nasal cavity.

Figure 1B:
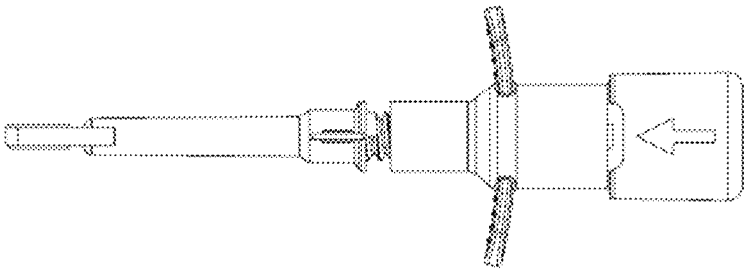

Reference is now made to FIG. 1A-B, disclosing a device according to one embodiment of the present invention. FIG. 1A shows an exploded view of the device, while FIG. 1B shows the device fully assembled. As shown in FIG. 1A, the device comprises, inter alia, a BFS nose piece (1), a pressurized-fluid container (2), an air chamber gate (3) and an activation mechanism base (4).

In the FIG. 1A, the base (4), an air chamber gate (3) has with a first gate O-ring at its proximal end and a second gate O-ring at its distal end (both shown in FIGS. 7A-7B and 8A-8E, as numerical reference 77 and 78).

The pressurized-fluid container (2) will fit over the air chamber gate (3), with the first gate O-ring and the second gate O-ring providing airtight seals before activation so that compressed gas is storable between the air chamber gate (3) and the pressurized-fluid container (2).

As will be disclosed hereinafter, the pierceable drug container (1) (e.g., BFS) in the nosepiece, where there is a puncturing element that punctures the drug container and once the compressed gas is released from the pressurized-fluid container (2), the same entrains the drug and deliver the same to the nasal cavity (see FIGS. 7A-7B and 8A-8E).

Figure 2A:
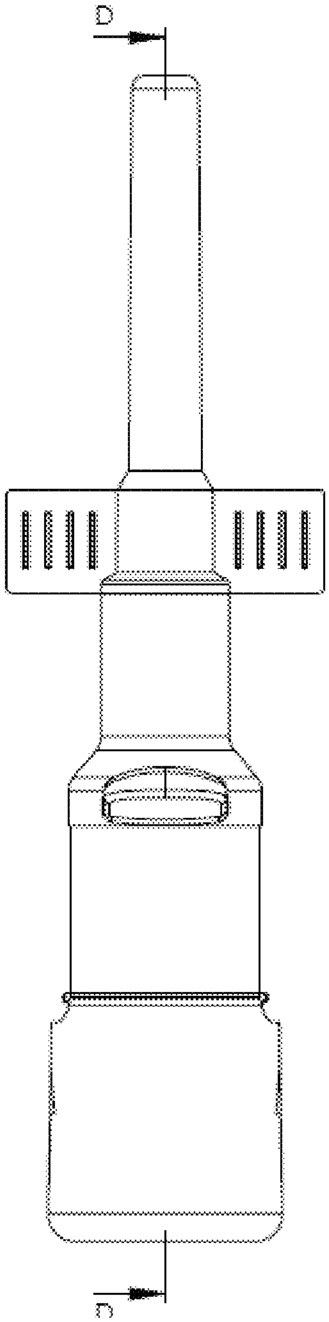
FIGS. 2A-C shows another embodiment of the present invention, with FIG. 2A showing the device, FIG. 2B showing a cross section of the device and FIG. 2C showing an enlarged view of a portion of the device.
Figure 2B:
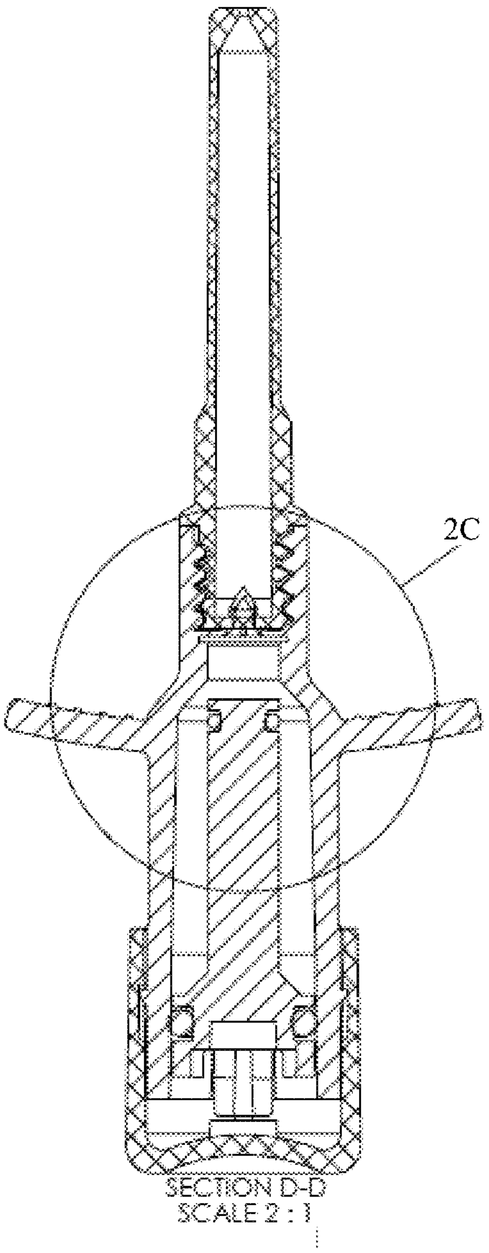
Figure 2C:
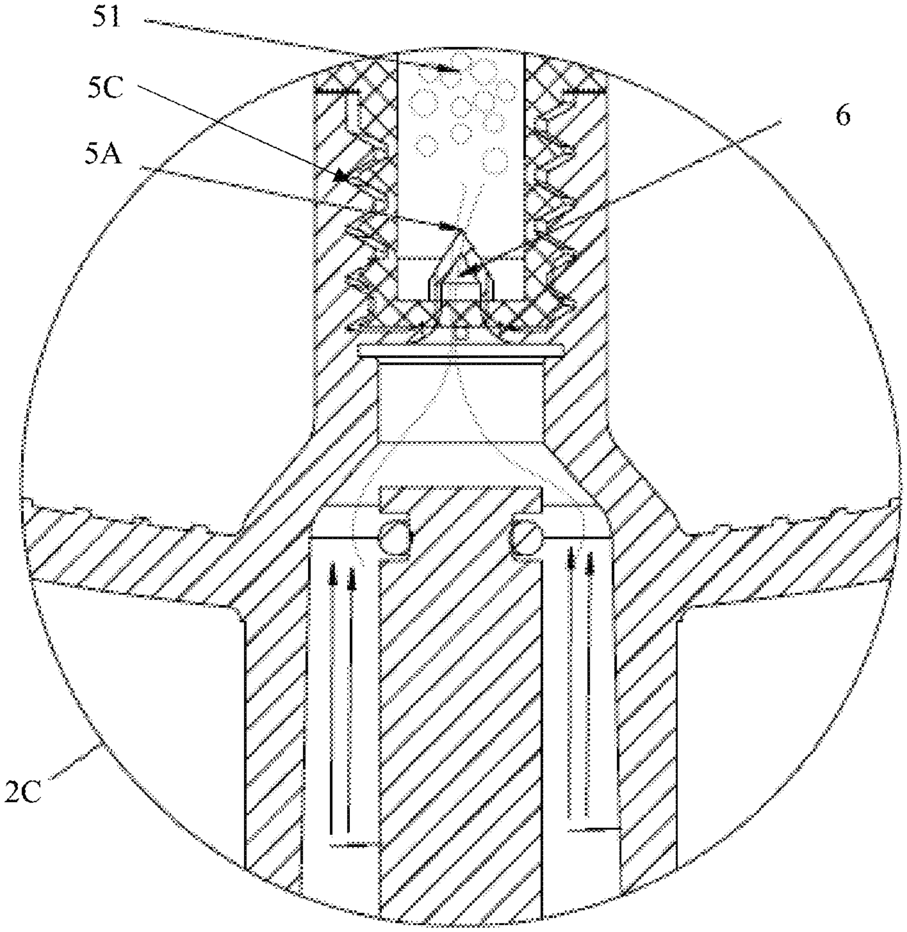
Figures 7A, 7B:
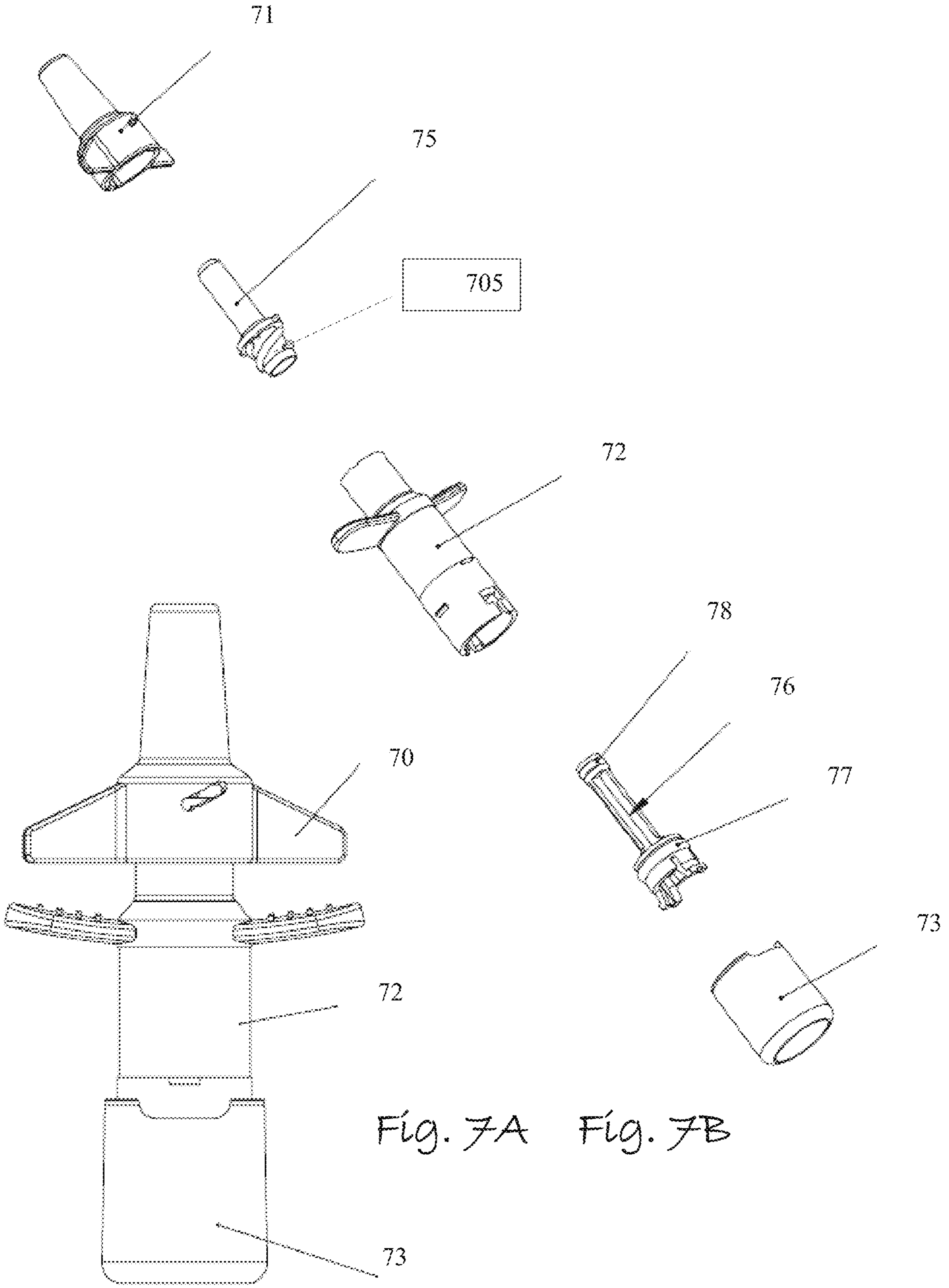
FIGS. 7A-7B illustrating a device being another embodiment of the present invention, a front and exploded view, respectively.

As shown in the FIGS. the base of the device forms the activation button (4); to activate, the activation button (4) is pressed upward, then the air chamber gate (3) is drawn downwardly, which removes the sealing of the upper O-ring (78 in FIGS. 7A-7B). The movement of the air chamber gate (3) opens a gap between the pressurized-fluid container (2) and the BFF nose piece (1), allowing the pressurized-fluid to escape from container 2, enter BFF nose piece (1) (after the same has been pierced by the piercing needle 79, shown in FIGS. 7A-7B), and entrain the substance to the nasal cavity. Reference is now made to FIGS. 2A-C, disclosing a device according to another embodiment of the present invention. FIG. 2B depicts a cross section along the line D:D of the device as shown in FIG. 2A. The area within the circle 2C in FIG. 2B is shown enlarged in FIG. 2C, where the device's spike is disclosed (6). Also seen in FIG. 2C is a BSF lower BFS point at which the needle punctures the BFS (5A), BSF nosepiece which contain the drug (51) and an activation screw mechanism (5C).

Figure 3A:
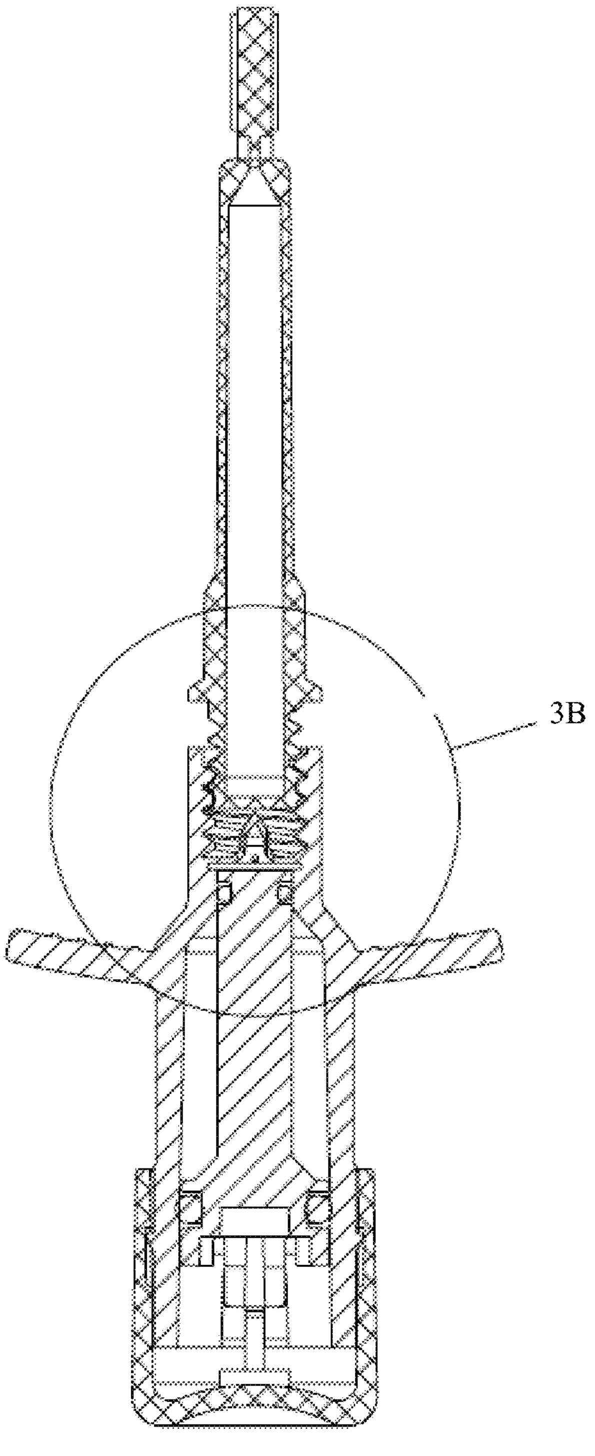
FIGS. 3A-D shows another embodiment of the present invention, with FIG. 3A showing a cross-section of the device, FIG. 3B showing an enlarged view a portion of the device, FIG. 3C showing the exterior of the nosepiece and FIG. 3D showing the device from the top.
Figure 3B:
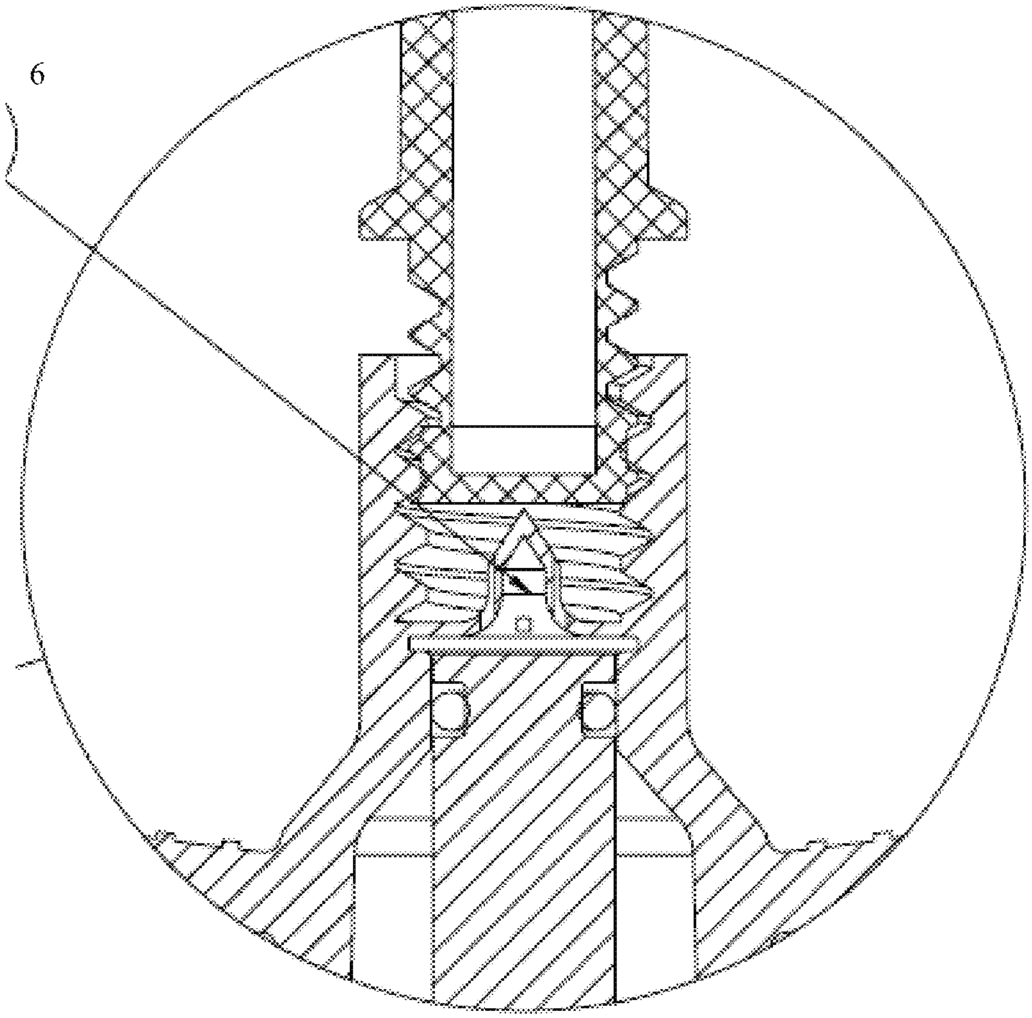
Figure 3C:
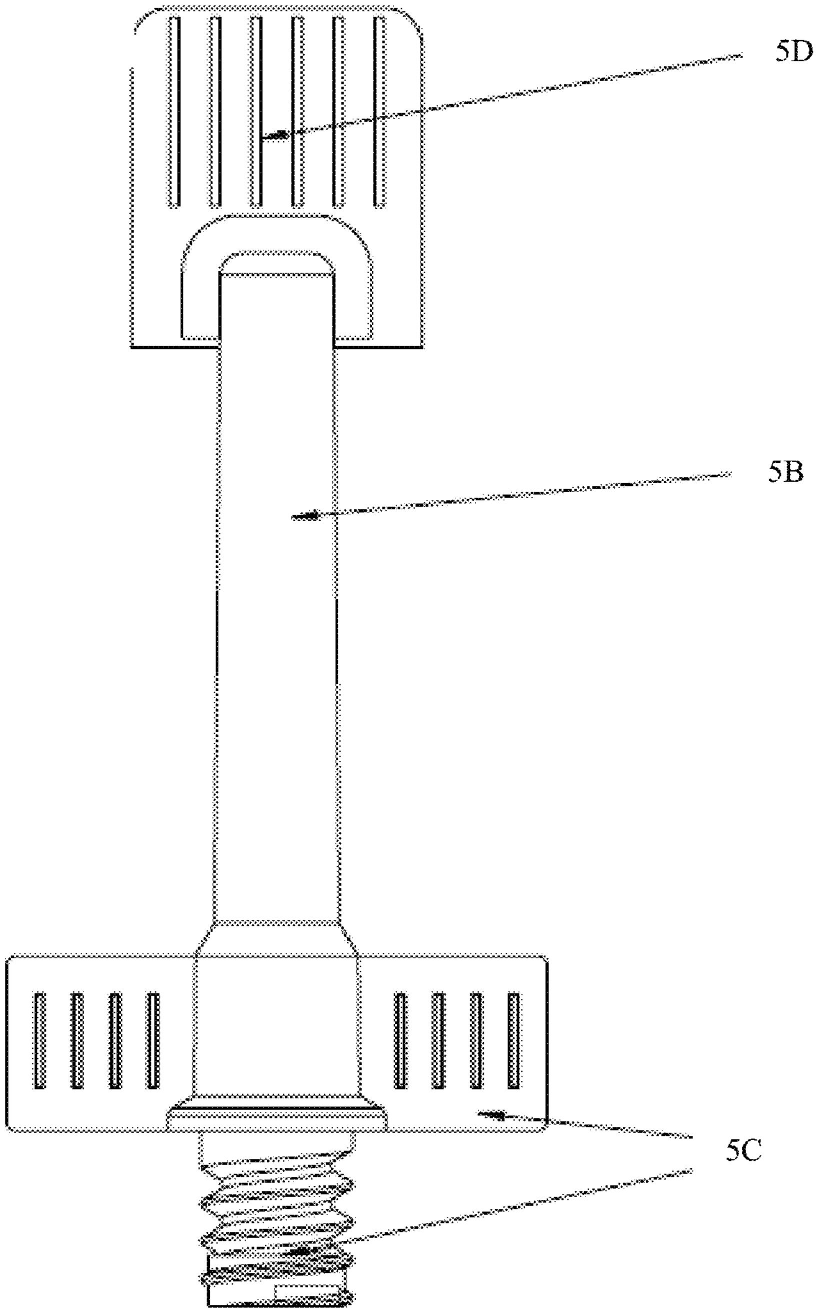
Figure 3D:
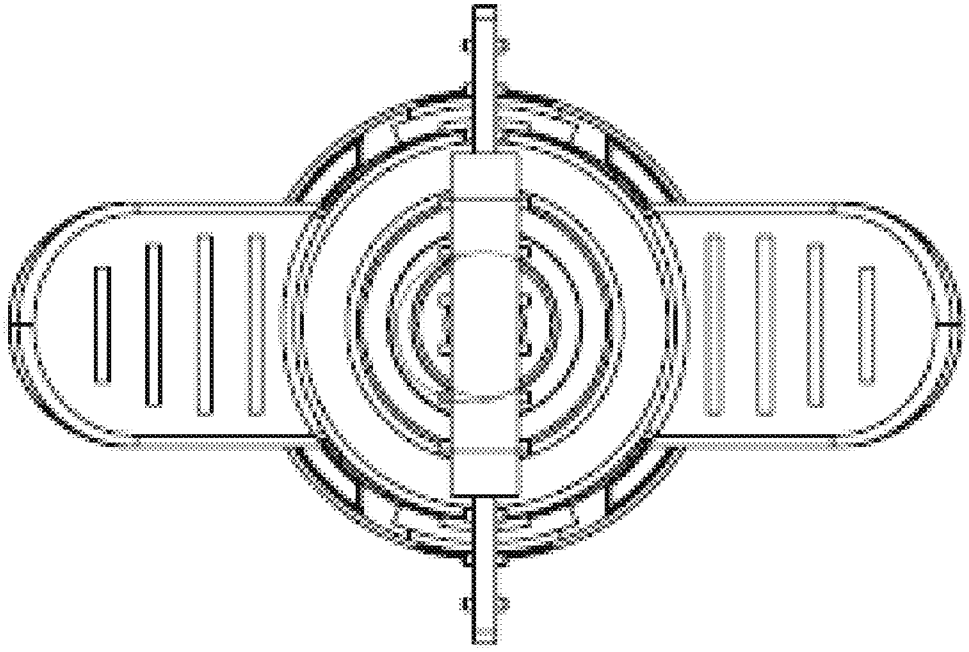

Reference is now made to FIGS. 3A-D, disclosing a device according to another embodiment of the present invention. FIG. 3A shows a cross-section of the device. FIG. 3B shows an enlarged view of the area inside the circle 3B of FIG. 3A. The piercing member (6) can be clearly seen. FIG. 3C shows the exterior of the nosepiece, showing the activation screw mechanism (5C) that is tightened in order to drive the bottom of the drug container against the spike and thereby pierce the drug container; the nosepiece cover (5D) and the main body of the nosepiece (5B). FIG. 3D shows the device from the top.

Figure 4A:
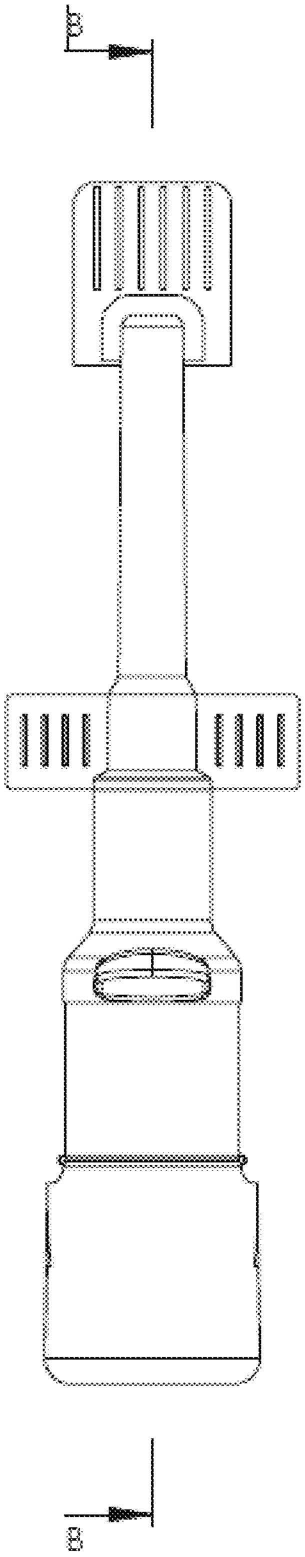
FIGS. 4A-C shows another embodiment of the present invention, after activation, with the device shown in FIG. 4A, a cross section of the device in FIG. 4B and an enlarged view a portion of the device in FIG. 4C.
Figure 4B:
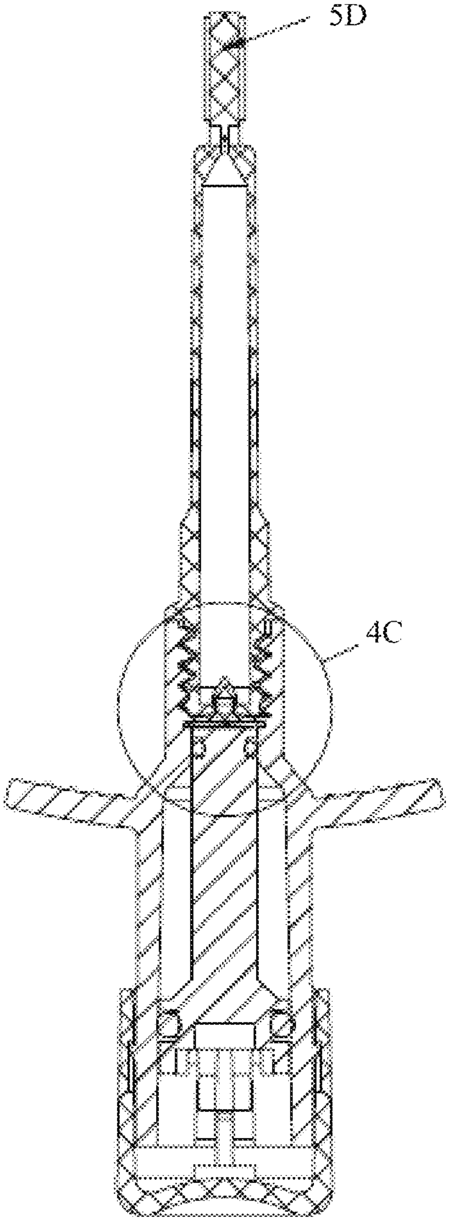
Figure 4C:
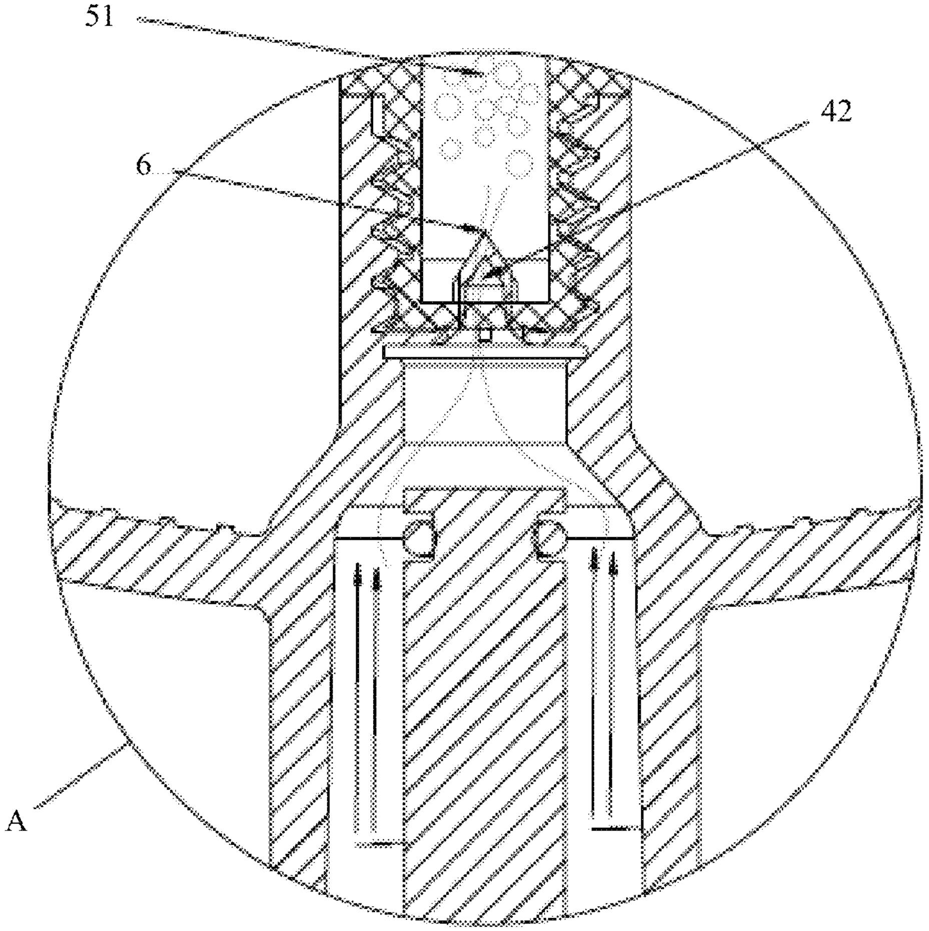

Reference is now made to FIGS. 4A-C, disclosing a device according to another embodiment of the present invention. Here a device is after the activation (FIG. 4A). FIG. 4B shows a cross section of the same along the line B:B. The area within circle 4C is shown enlarged in FIG. 4C, namely a cross section of the piercing member. Drug powder and/or liquid schematically illustrated (51). Air flow through the spike holes (42) entrains the drug.

Figure 5B:
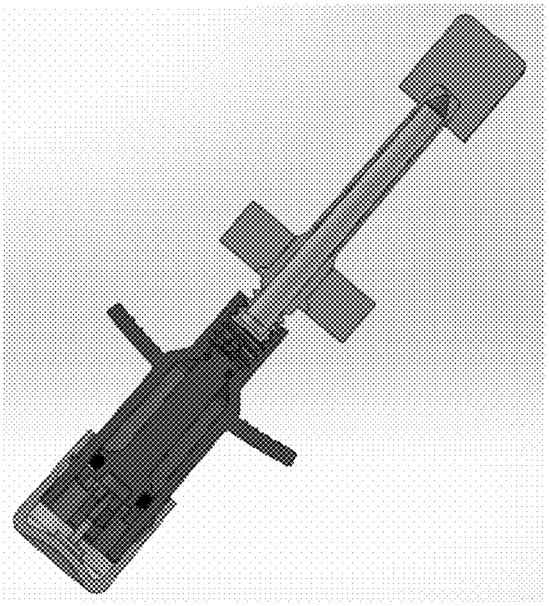
FIGS. 5A-G show another embodiment of the device, with FIG. 5A showing a side view of a pre-used device carrying a BFS, FIG. 5B showing a cross section of the same, FIGS. 5C and 5D depicting the device when connected to a BFS, FIG. 5E showing the same when the device is ready to use, FIG. 5F showing connection of the BFS to the device.
Figure 5A:
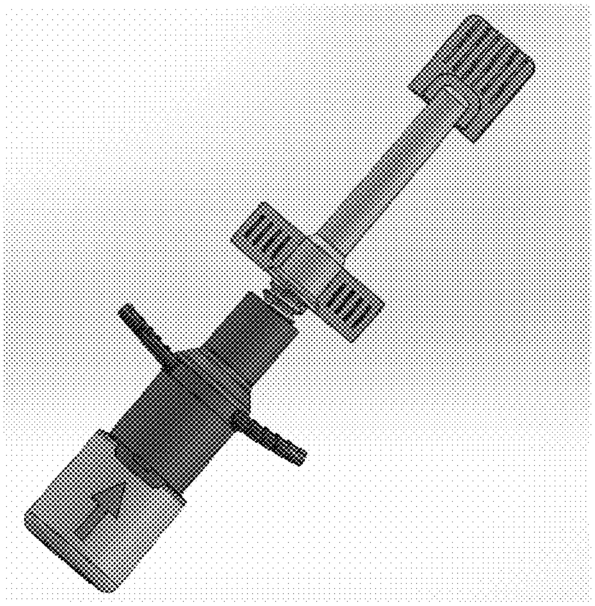
Figure 5D:
Figure 5C:
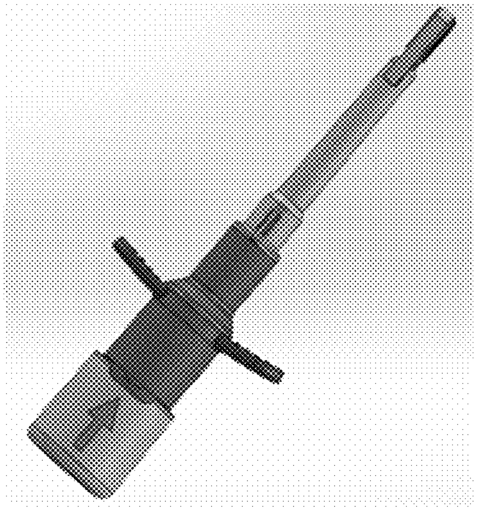
Figure 5E:
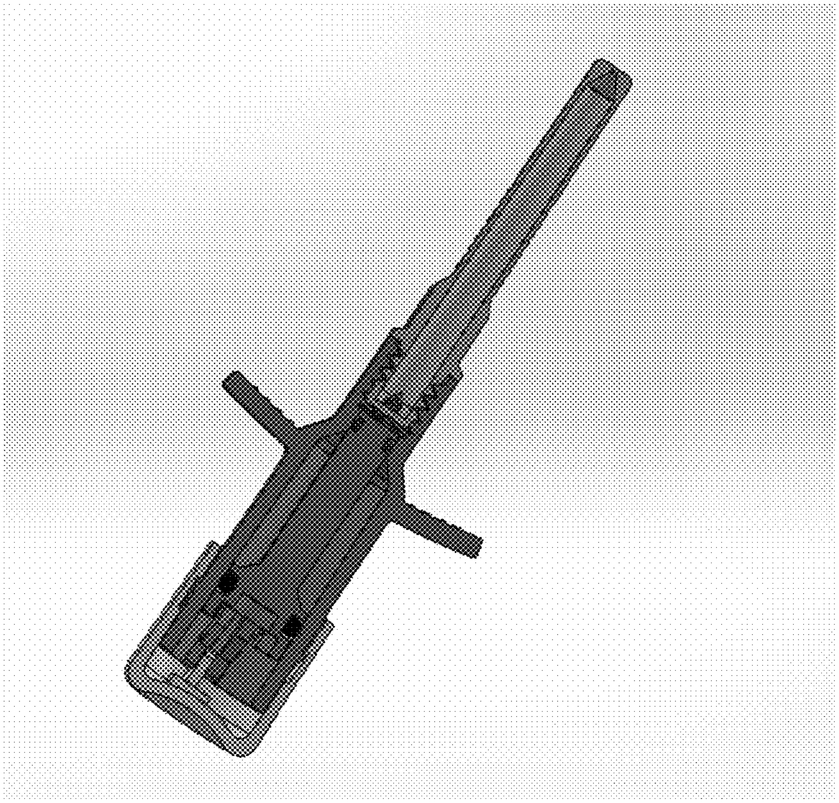
Figure 5F:
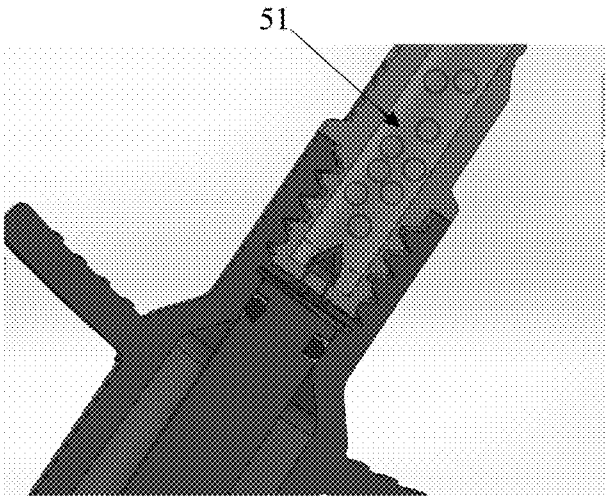
Figure 5G:
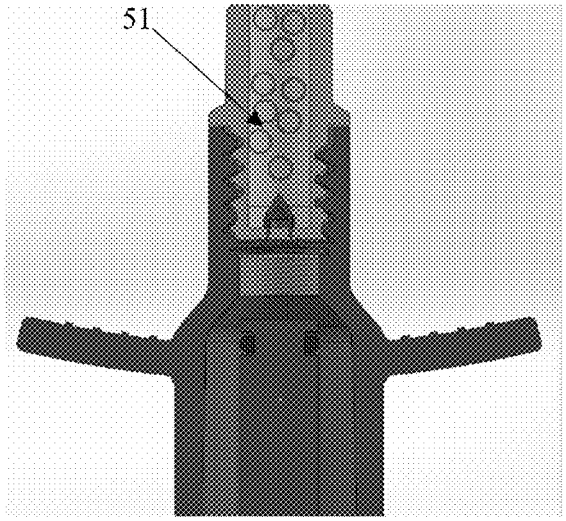

Reference is now made to FIGS. 5A-G, disclosing a device according to another embodiment of the present invention. FIG. 5A is a side view of a pre-used device carrying a BFS, and FIG. 5B is a cross section of the same. FIGS. 5C and 5D similarly depict the device when connected to a BFS. FIG. 5E shows the same when the device is ready to use, FIG. 5F illustrates the connection between the BFS to the device; drug (51) is shown. The device after activation presents the flowing drug (51) in FIG. 5G.

Figure 6A:
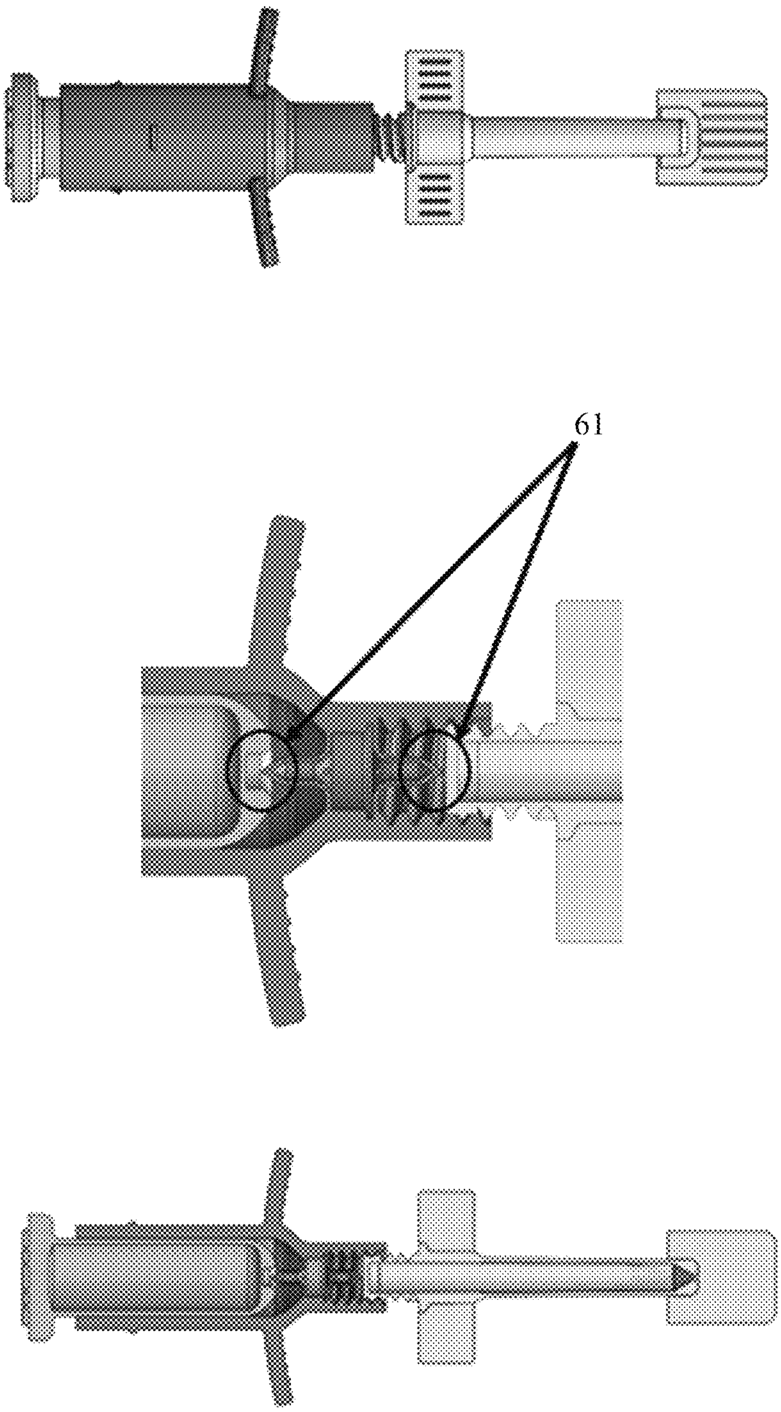
FIGS. 6A-E show another embodiment of the present invention, with FIG. 6A illustrating a front view of a pre-used device carrying a BFS and cross sections of the same.
Figure 6B:
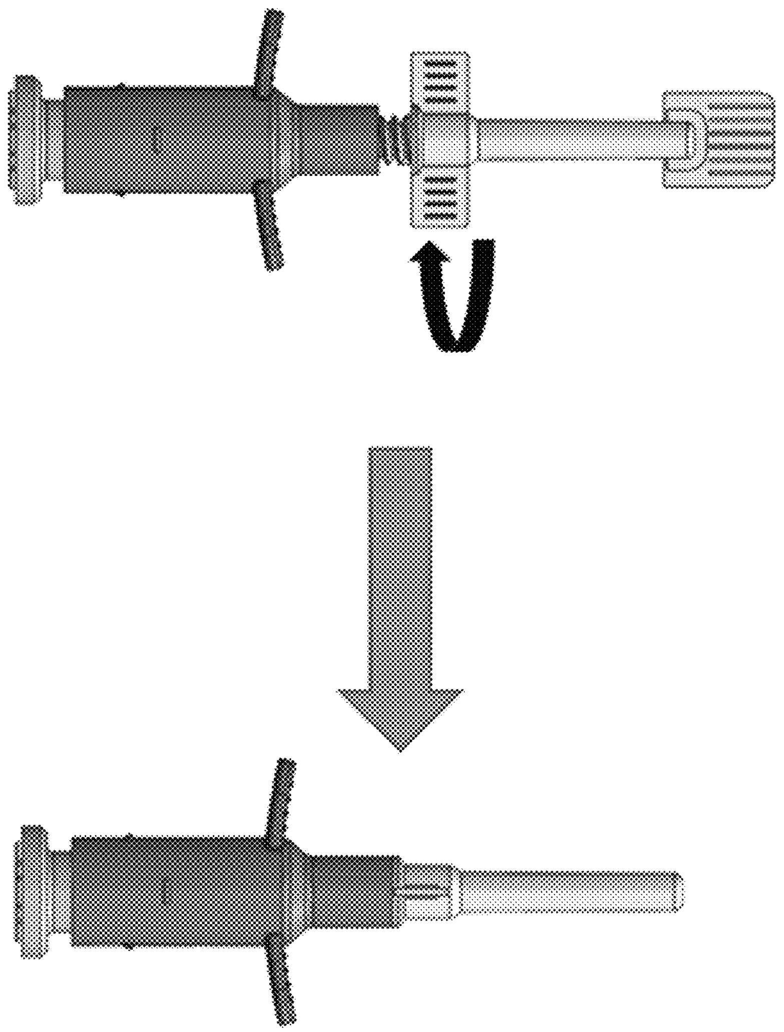
Figure 6C:
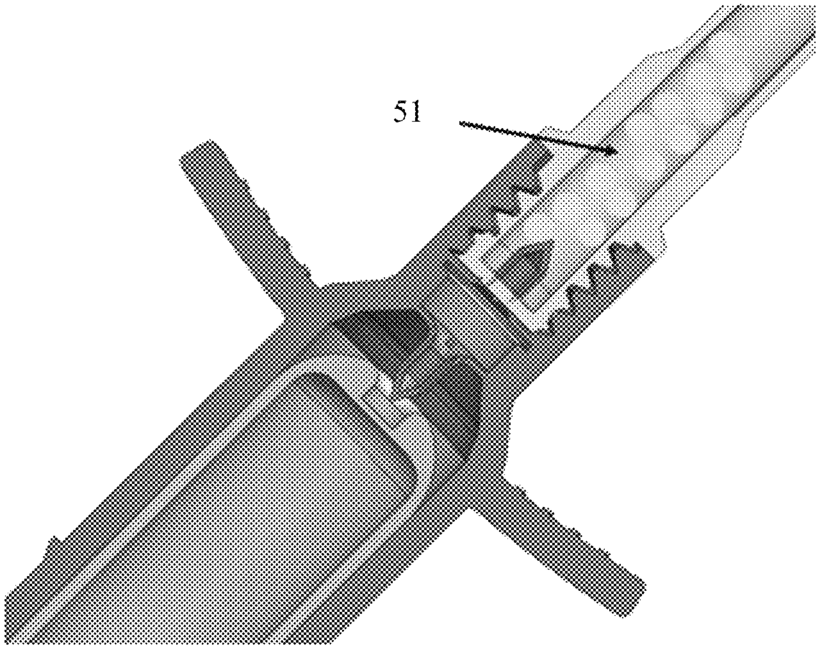
Figure 6D:
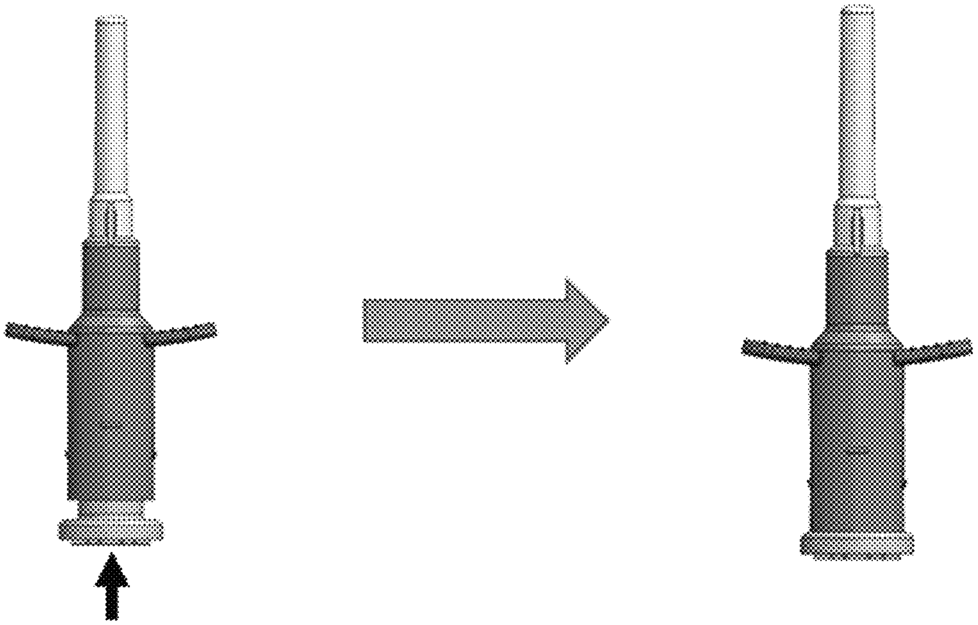
Figure 6E:
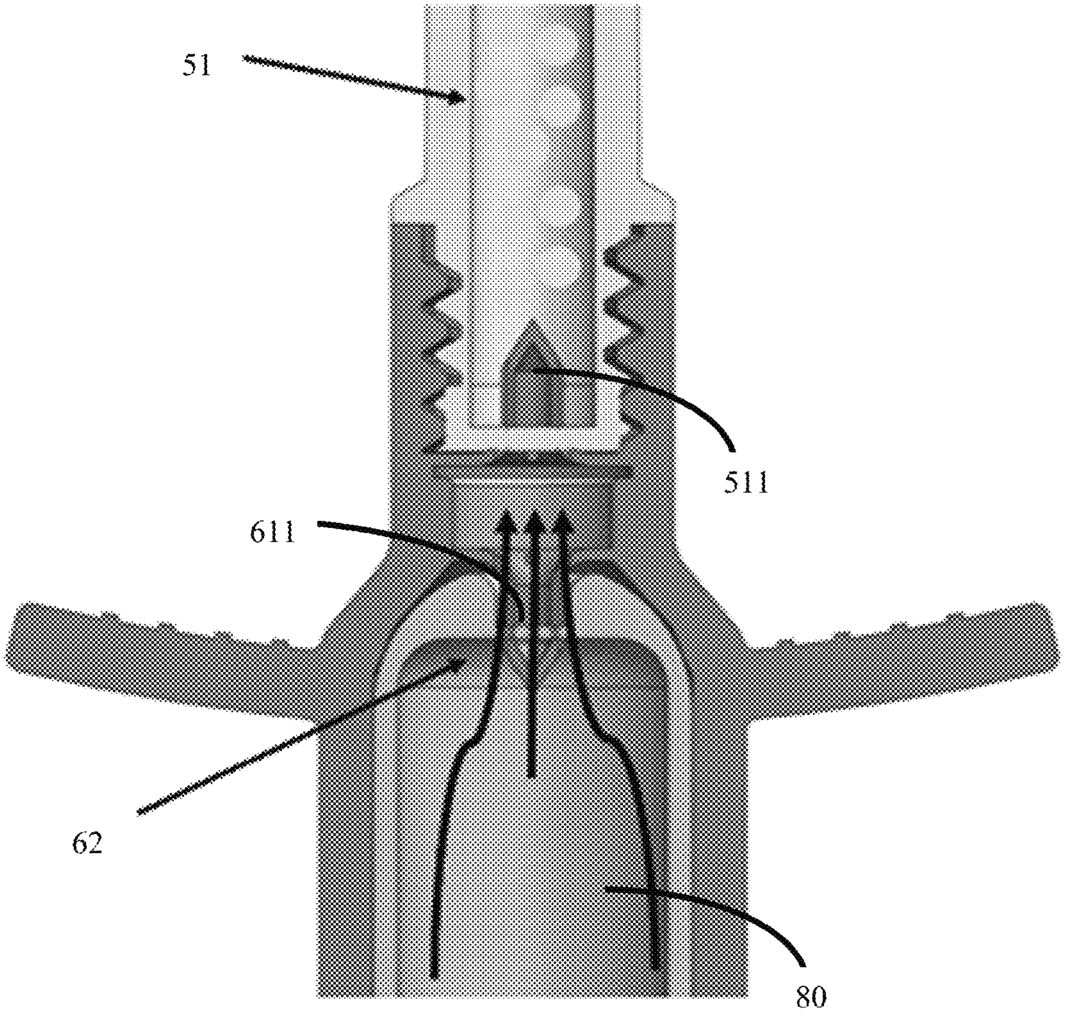

Reference is now made to FIGS. 6A-E disclosing a device according to another embodiment of the present invention. FIG. 6A illustrates a side view (image on the top) of a pre-used device carrying a BFS. Images on the middle and in the bottom are cross sections of the same, showing BFS nosepiece and BFS air container before contact in the regions 61. FIG. 6B shows the second step after introducing the BFS, namely securing the BFS to the device, here by turning the nosepiece of the BFS clockwise. Upon rotation of the nosepiece, the piercing member 511 (shown in FIG. 6C), pierces the drug compartment. A further step is removing (e.g., breaking) the cap, the image at the bottom presents the device after breaking the said cap. The drug (51) is presented in cross section view of FIG. 6C. In FIG. 6D, a button at the base of the device is pushed. Such push actuates the base and a second piercing member 611 pierces the container 80. Subsequently, as depicted in FIG. 6E, pressurized fluid (air, nitrogen etc.) flows from its container (62) to the drug-containing BFS and carries the drug (liquid phase, solid powder particles etc.) (51) outwardly.

One should also note that this example is shown for the same invention but with another kind of pressurized gas container and a different way of compressed gas discharge (by puncturing the container rather than the gate that is shown in the previous figures.

Reference is now made to FIG. 7A, FIG. 7B and FIGS. 8A-8E disclosing a device according to another embodiment of the present invention in a side view and exploded view, respectfully; wherein 70 is a cover holding area; 72 is a pressurized fluid container; 73 is an activation mechanism base; 74 is a cover's body; 75 is a nosepiece; 76 is an air chamber gate; 78 and 77 are O-rings; 79 is a needle; 75 is a nosepiece one way screwing mechanism; 710 is a drug's space; 712 is an air chamber gate's legs; 713 is an air chamber gate's snaps; 714 is a drug storage container locking notch; 715 is a drug storage container locking pin; 716 is an orifice-creating piercing needle; 717 is an orifice; 718 is an aerosol; 720 is a safety latch; 721 and 722 locks; 723 is a pressurized fluid container's internal screwing mechanism. The device comprises modules 70-79 and 710-720, where 71, 74, and 713, and nozzle (orifice) 717 are related with the nosepiece; 72, 76-79, 710-712, 716, to the body and module 73 and 713 is in device's operating button.

Figure 8A:
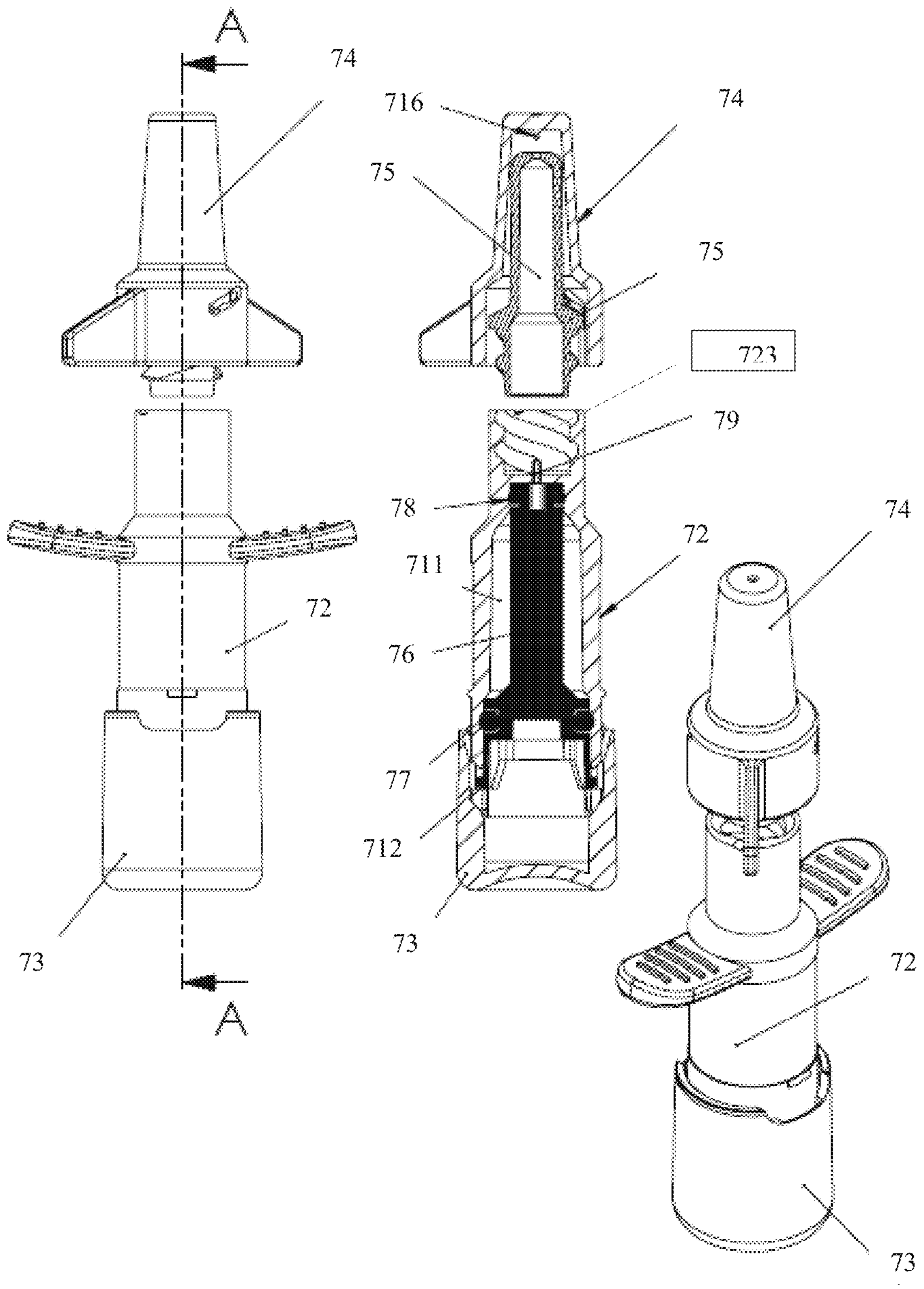
FIGS. 8A-8E show same device in various modes of operation.
Figure 8B:
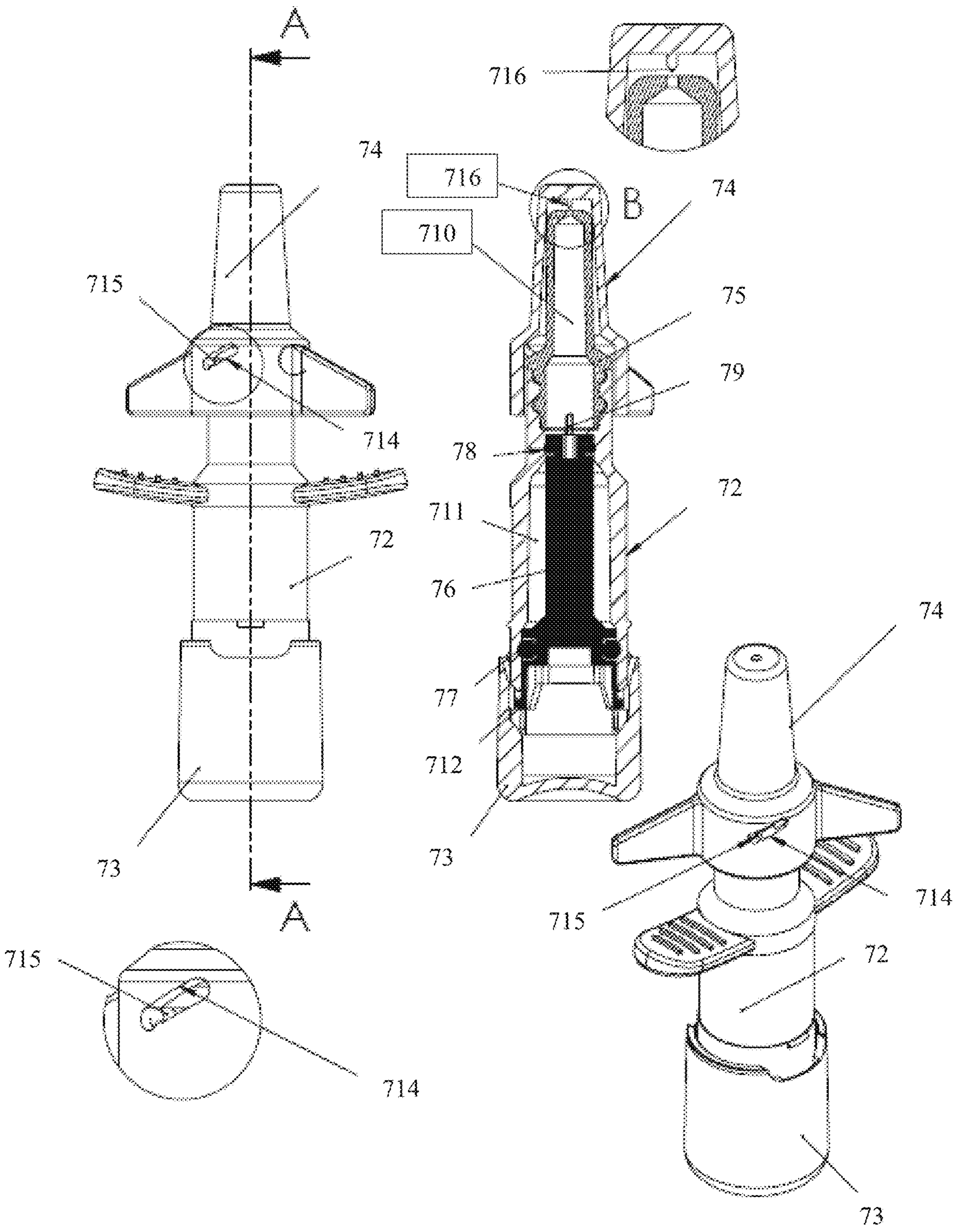
Figure 8C:
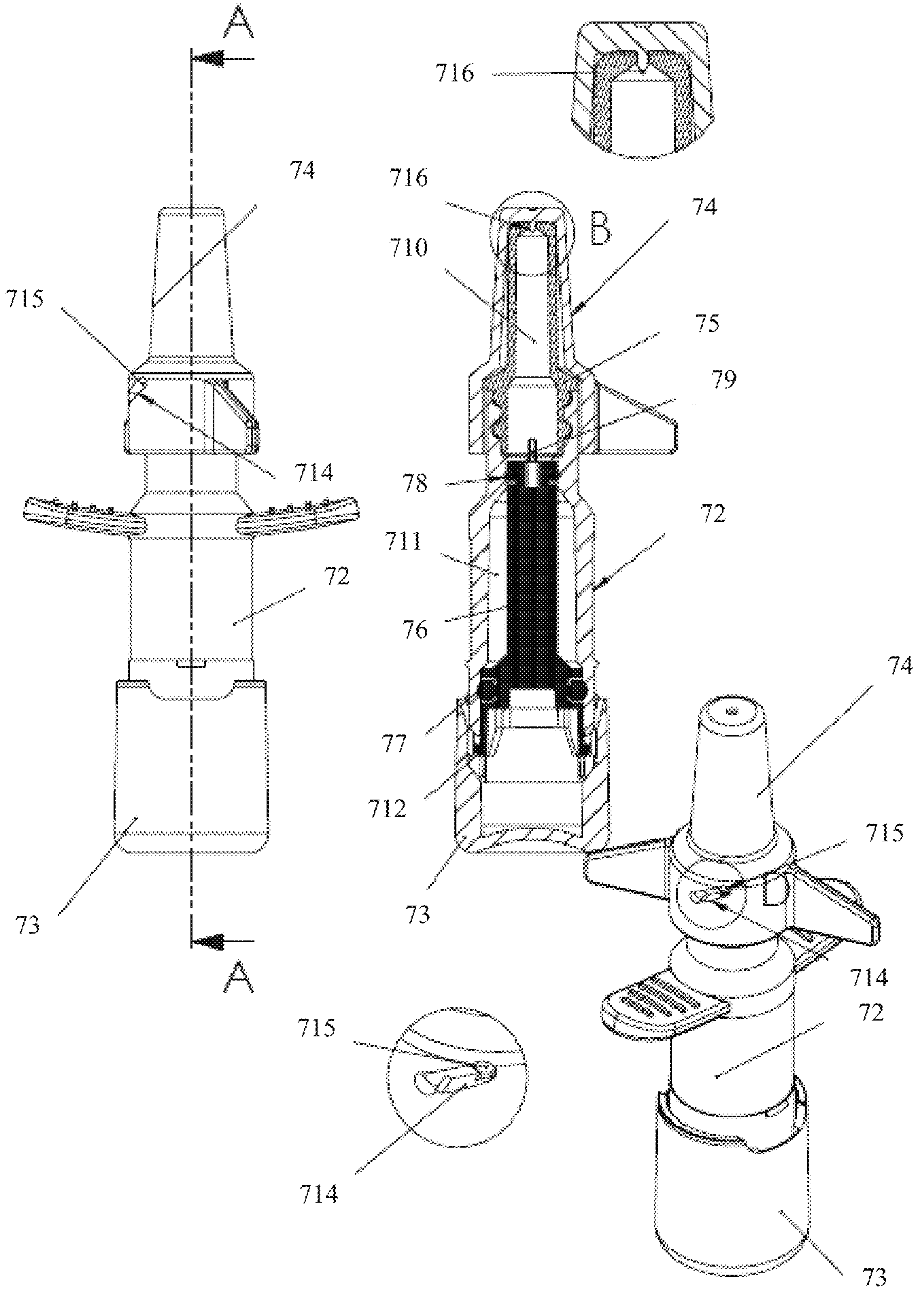
Figure 8D:
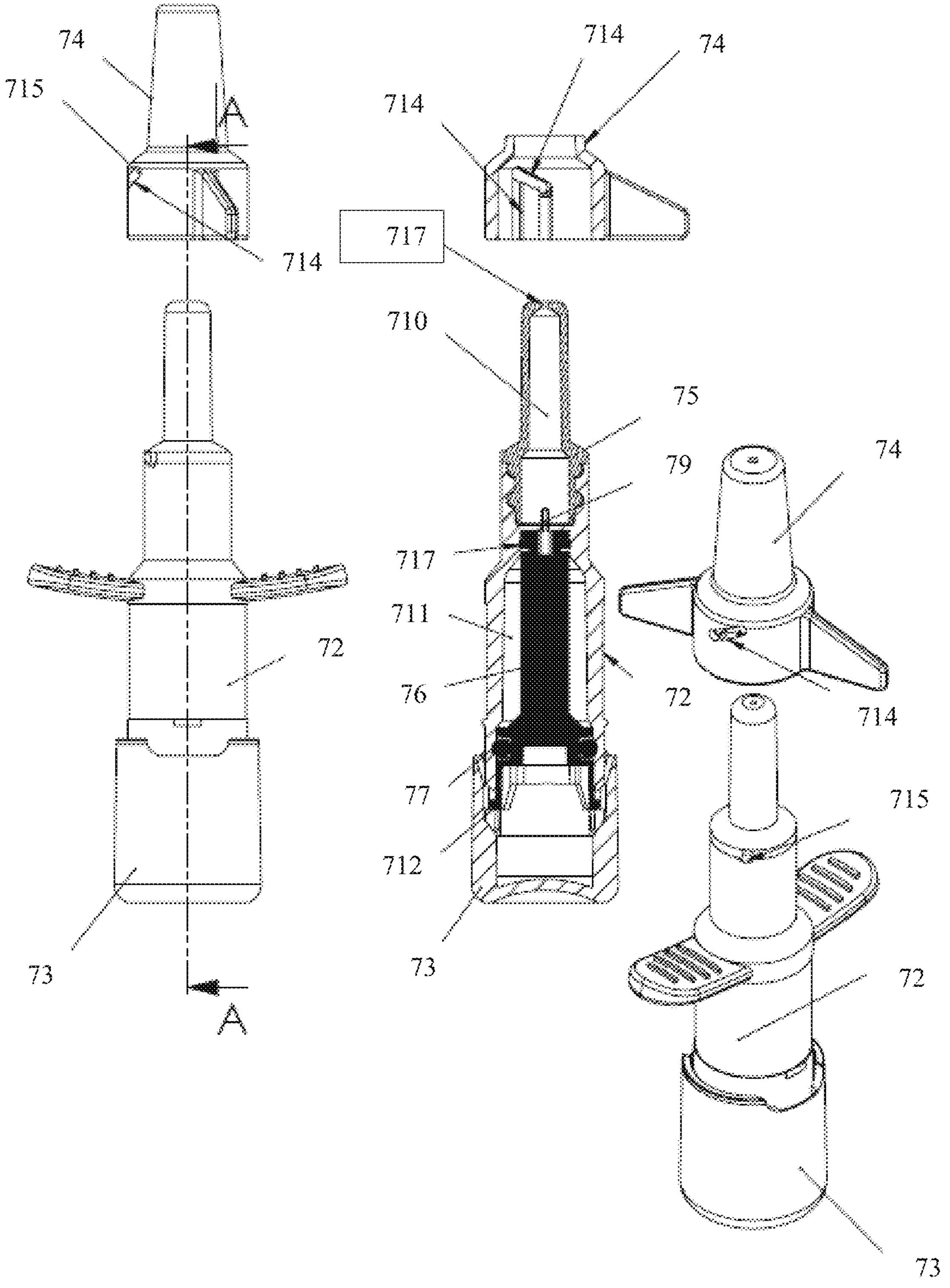
Figure 8E:
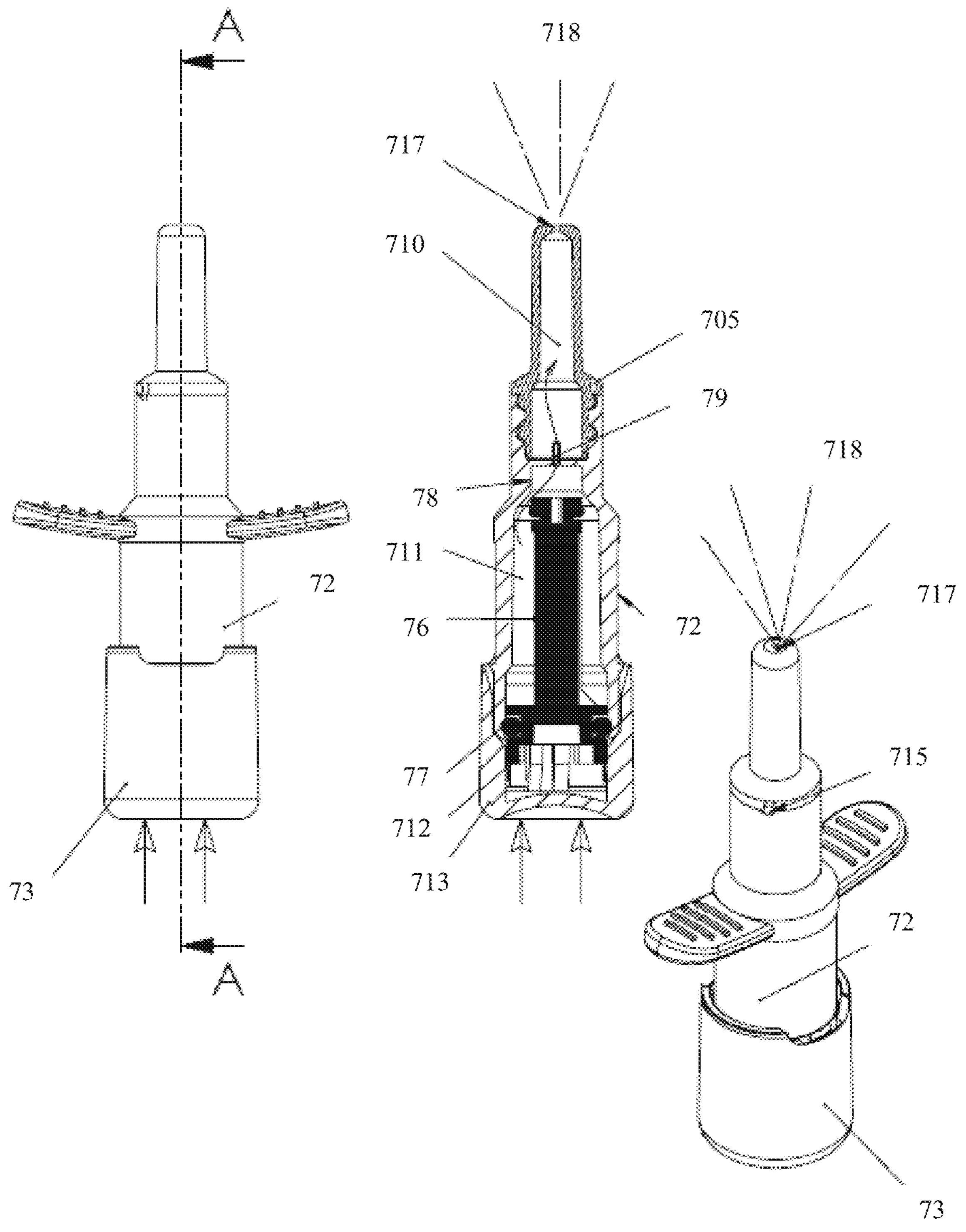

In the following sets of figures, namely FIG. 8A-8E, operation modes are illustrated, illustrating a method for delivering either one or more substances within at least one body cavity, characterized by steps of providing a vial with $V_{sub}$ [ml] of said substances; said vial selected from a pierceable container, a blow-fill-seal and a form-fill-seal, further providing said vial with a fluid inlet and a fluid discharging outlet of diameter D [mm], configured for placement in proximity to said body cavity; configuring said fluid inlet by means of size and shape to interface a puncturing member, so that upon coupling to the fluid inlet, piercing of the same, thereby providing the substances in a fluid communication, via a valve, with a chamber configured to accept pressurized fluid at volume $V_{PF}$ [ml] (or mg) and pressure $P_{PF}$ [barg]; the valve is commutable from an CLOSE to an OPEN CONFIGURATION within a short period of time, <500 milliseconds (dT); at the OPEN CONFIGURATION, facilitating the flow of the pressurized fluid to from the chamber, via the fluid inlet, entraining the substances; and then erupting via the fluid discharging outlet to within the body cavity, such that the release time of the $V_{sub}$ [ml or mg] of the substances and the $V_{PF}$ [ml] of the pressurized fluid, $dT_{release}$ is less than 500 milliseconds. Each pf the figures comprises a front view (left side), cross-section (A:A, middle) and isometric view (right side). FIGS. 8B and 8C further depict a rotation mechanism 714-715, which allows a rotation (here, ¼ rotation) thereby enabled the piercing of the nosepiece substance container.

According to another embodiment, the rotation results in a double piercing of the nosepiece substance container and the pressurized air container.

According to another embodiment the pressurized air container is sealed by means of at least one O-ring, such that movement of the o-ring removes the sealing and enables the release of the pressurized air. In some embodiment at least 2 o-rings are used. One o-ring at the bottom of the pressurized air container and the second at the upper portion of the pressurized air container to seal and separate between the pressurized air container and the nosepiece substance container.

At final step (FIG. 8E), upon pressing the activation mechanism base 73, results in movement of the air chamber gate 76 and the upper o-ring to thereby enable the release of the pressurized air from the pressurized air container and into the nosepiece substance container to entrain the same. Once the pressurized air entrains the substance, aerosol 718 is provided throughout the orifice 717, having a narrow plume angle (θ). It is in the scope of the invention wherein the cover comprises means to protect the drug from UV, e.g., photoprotective agents, such as oxybenzone, titanium oxide and octyl methoxycinnamate.

Figure 9:
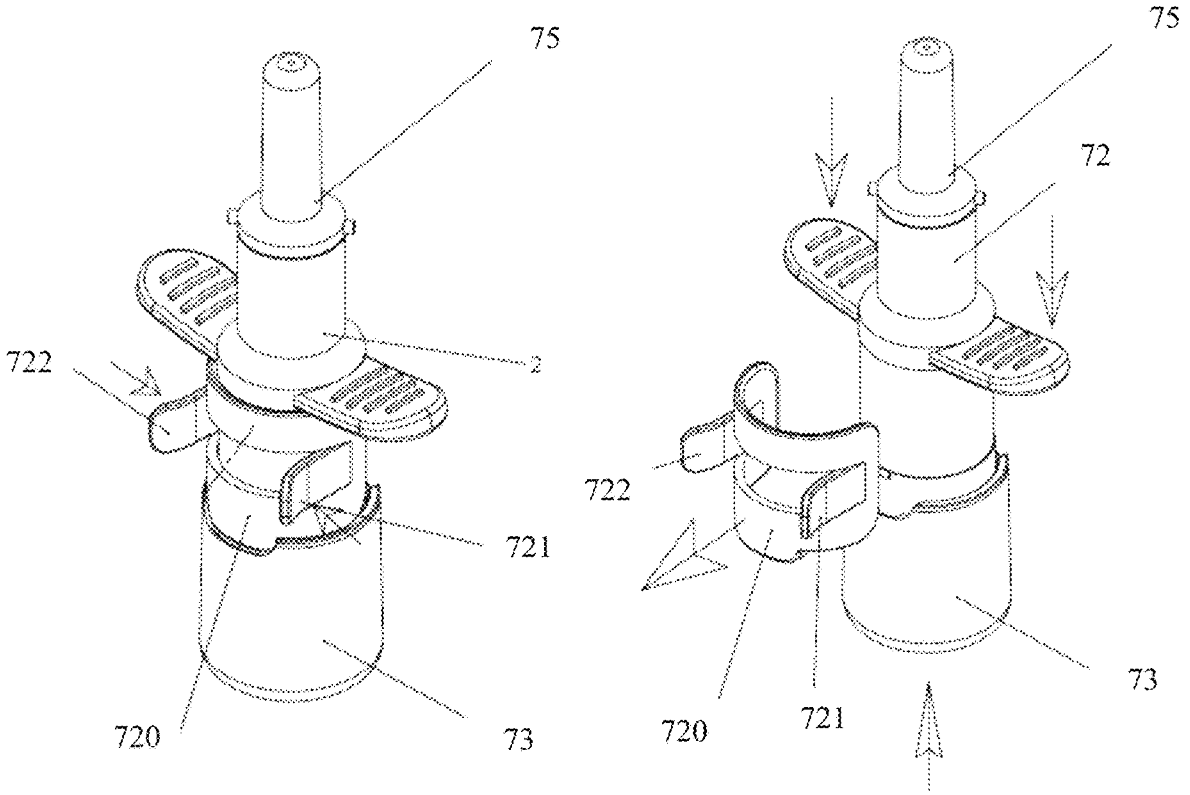
FIG. 9 depict two views of the device interconnected to a safety latch according to an embodiment of the present invention.

Reference is now made to FIG. 9 disclosing a device according to another embodiment of the present invention, where the device comprises a safety latch 720 with its two locks 721-722, configured to avoid undesired or accidental operation of the device, i.e., by pressing activation mechanism base 73 and pressurized fluid container (body) 72.

It is well in the scope of the invention wherein the pressurized fluid is accommodated within container for a respectively long time, e.g., by having a pre-pressurized container (step 1A) in a fluid connection (step 2A) with the BFS and releasing the same (step 3A), or alternatively a container suitable to pressuring the fluid in situ within the container, e.g., by introducing a pump or piston mechanism that pressuring ambient air to the container in a first step (step 1B) and accommodating the pressurized fluid along a relatively short time of step 2B, then free the fluid to flow in step 3B.

By the device disclosed herein, the pre-aerosolized mixture of gas and substance exits the device with a significant driving force as a mixture of aerosol and pre-aerosolized material (fluid or powder). When the pre-aerosolized material hits the walls of the nasal passages, it "explodes" into a fine aerosol that is capable of being driven by the pressure deep into the nasal passages to deposit in the desired region.

Figure 10:
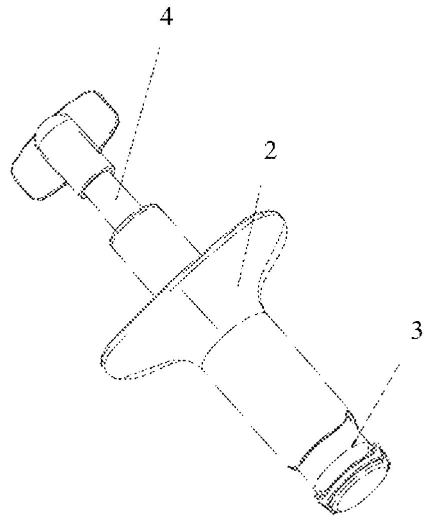
Figure 11:
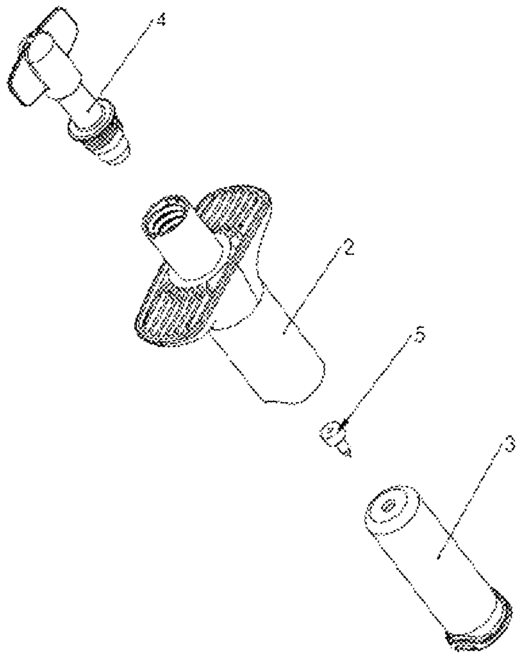

Reference is now made to FIGS. 10-11 which illustrates another embodiment of the present invention, in which the pierced container is the pressurized gas container.

FIG. 10 illustrates the nosepiece 4 (containing the medicament container), the handle, the device body 2 and the pressurized air container 3.

Reference is now made to FIG. 11, illustrating an embodiment in which the pressurized gas container 3 is pierced by means of a dedicated hollow needle 5.

According to this embodiment, once the device is activated (the pressurized gas container 3 is pressed against the handle), needle 5 pierces the pressurized gas container 3 and the pressurized gas exits therefrom and enters the medicament container to entrain the medicament into the nasal cavity.

Needle 5 is a hollow needle such that when the same pierces the gas container, the pressurized gas exit the pressurized gas container 3 throughout needle 5.

Needle 5 comprises two ends, one of which is a flat, non-sharp end, in fluid communication with the medicament container (will be disclosed hereinafter) and the second one has a sharp end, adapted to pierce the gas container. The two ends interconnected by means of a hollow tube. Once the gas container is pierced the pressurized gas exits therefrom through the hollow tube.

Reference is now made to FIG. 12 illustrating one embodiment of the nosepiece 4 enclosing a powder medicament. According to this embodiment the nosepiece has a cap 11 adapted to cover the distal most part of the nosepiece body 12. Within the nosepiece body 12, a dedicated medicament capsule 14 is disposed. The medicament capsule 14 is adapted to enclose e.g., powder medicament. However, one skilled in the art would acknowledge that also liquid, gas or gel medicament are also within the scope of the present invention. Furthermore, capsule 14 can enclose a combination of both liquid and powder medicaments.

According to this embodiment, at least one spherical element, preferably ball 13, is disposed within the medicament capsule 14. According to another embodiment, at least two spherical elements, preferably ball 13, are disposed within the medicament capsule 14, such that the medicament are disposed between the two balls 13.

The spherical elements are adapted to both (a) seal the medicament capsule 14 and prevent leakage of medicament therefrom; and, (b) once the pressurized air exits the pressurized gas container, the bottom most spherical element 13 is removed from its position (thereby removing the sealing thereof and enabling the pressurized gas to enter therein) and mixes/compress the medicament enclosed between the two spherical elements 13. Once, the first (bottom most) spherical element is removed, the same compress the medicament disposed between the first and second spherical elements 13 and causes the removal of the second (upper most) spherical element 13. Thereafter, the medicament along with the pressurized gas are delivered to the nasal cavity.

Figures 13C, 13D:
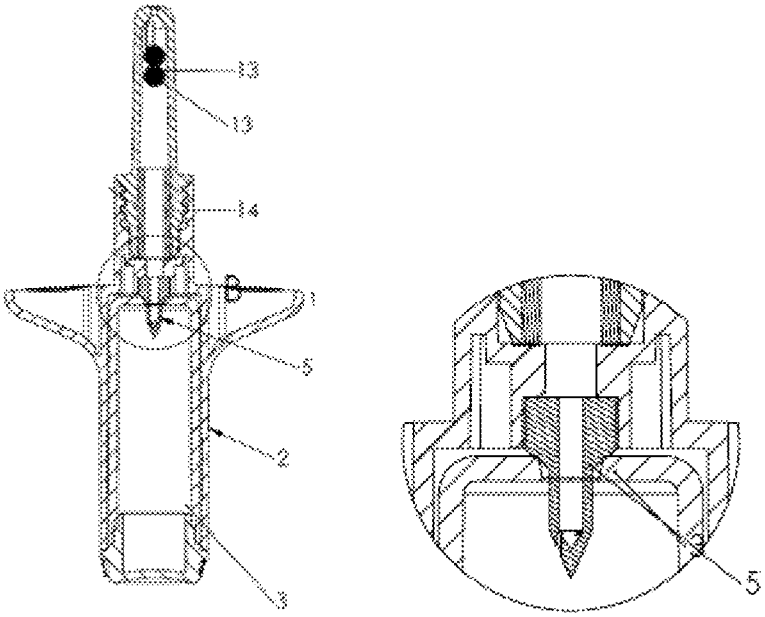

Reference is now made to FIGS. 13*a*-13*d* illustrating the step-by-step activation of the device. FIG. 13*a* illustrates the device before activation, in which the medicament is enclosed within the medicament container 14 and the gas container is not pierced yet. FIG. 13*b* provides a closer view of the needle 5 before activation thereof.

FIG. 13*c* illustrates the device after activation, in which the gas container is pierced, the pressurized gas had entered the medicament container, removed the two spherical elements 13 (the two spherical elements 13 are shown outside capsule 14) to enable delivery of the medicament 15. FIG.

13*d* provides a closer view of the needle 5 after activation thereof (i.e., pierced the gas container).

Figures 14A, 14B:
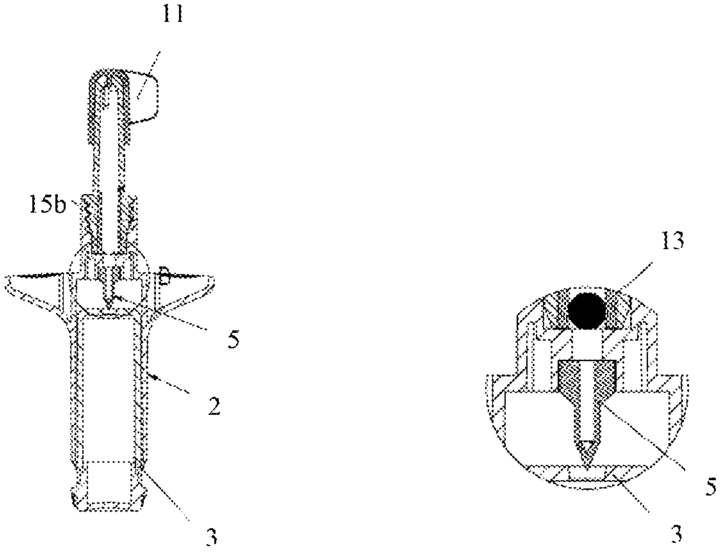

Reference is now made to FIGS. 14*a*-14*b* illustrating other embodiment of the present invention in which liquid medicament are utilized. According to this embodiment, only one spherical element 13 is utilized. Said spherical element 13 is disposed in the bottom most part of the medicament capsule to seal the same. Once, the needle 5 pierces the gas container, the pressurized gas exits the gas container through the hollow needle to remove the spherical element, entrain the medicament and deliver the same to the nasal cavity. FIG. 14*a* illustrates the device before activation, in which the medicament is enclosed within the medicament container 14 and the gas container is not pierced yet. FIG. 14*b* provides a closer view of the needle 5 before activation thereof.

Figure 15A:
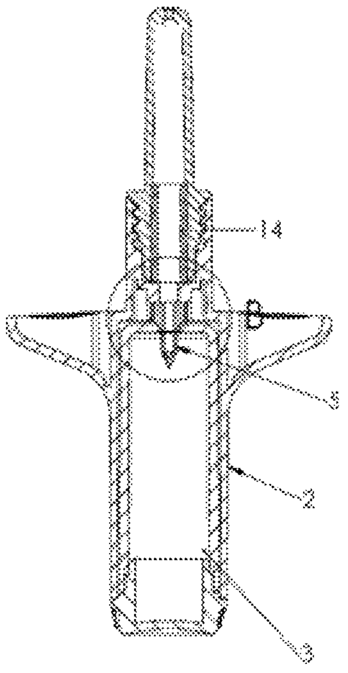
Figure 15B:
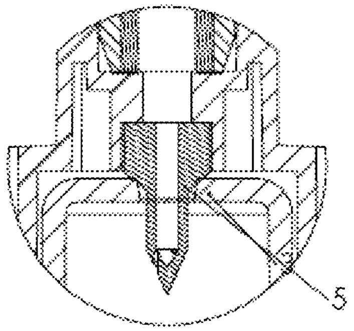

FIG. 15*a* illustrates the device after activation, in which the gas container is pierced, the pressurized gas had entered the medicament container, removed two spherical element 13 (the two spherical elements 13 are shown outside capsule 14) to enable delivery of the medicament 15. FIG. 15*b* provides a closer view of the needle 5 after activation thereof (i.e., pierced the gas container).

Figure 16:
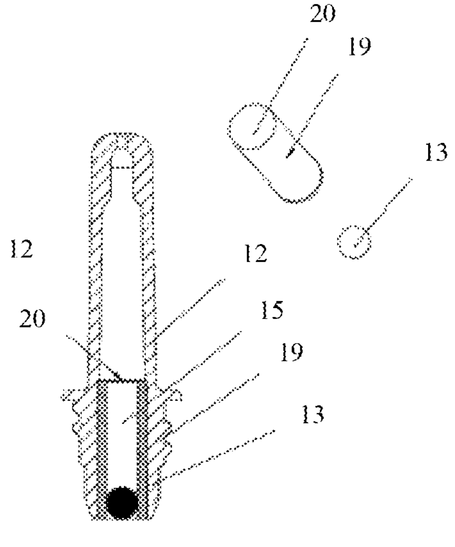

Reference is now made to FIG. 16, which illustrates a closer view of one embodiment of a capsule enclosing either liquid medicament or powder 15 and the spherical element 13. According to one embodiment a combination of liquid medicament and powder can be enabled by displacing e.g., the powder medicament on the bottom part of the capsule and the liquid medicament in the upper part thereof and vice versa.

According to this embodiment, the capsule comprises the spherical element 13 being displaced in the bottom most part of the capsule (providing sealing in the bottom part) and a breakable membrane 20 in the upper part thereof (providing sealing in the upper part).

It should be noted that different embodiments of the capsule are available. Reference is now made to FIGS. 17*a*-17*g*.

Figure 17A:
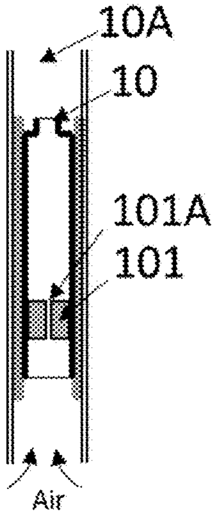

FIG. 17A shows a plunger-type barrier (101) between compartments. In this exemplary embodiment, there is one plunger (101). In other embodiments, more or fewer plungers (101) can be present. The plunger (101) comprises a hole or slot small enough to prevent passage of substance therethrough, but wide enough to allow passage of compressed air therethrough. When the device is activated, compressed gas (curved arrows at bottom) enters the capsule (10). The pressure forces the plunger (101) upward, forcing substance above the plunger (101) out of the top of the capsule. Substance below the plunger (101) will be forced upward by the compressed air, to mix with the substance above the plunger in a nose piece (not shown). The plunger (101) passes through the top of the capsule into an intermediate space (10A) below the nosepiece (not shown; a shoulder or other barrier (not shown) prevents the plunger (101) from exiting the nosepiece.

The hole or slot (101A) in the plunger (101) is narrow enough to prevent substance leakage during storage, and wide enough to allow compressed gas passage during activation, wiping the substance from the container during activation. The hole or slot (101A) in the plunger (101) can be designed in many ways to allow delivery that is very efficient, having a residual volume of less than 15% of the original volume. The plunger (101) can be made either from a flexible materials such as, but not limited to, silicone, rubber, flexible plastic or from a hard material such as, but not limited to, a polymer such as Delrin®, a plastic, nylon, metal and any combination thereof.

Figure 17B:
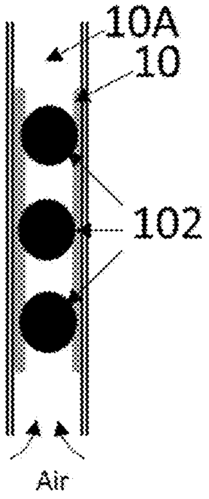

FIG. 17B shows ball-type barriers (102) between compartments. The balls (102) provide both a separation function, before activation, and a mixing function during activation. In this exemplary embodiment, there are 3 balls (103). In other embodiments, more or fewer balls (103) can be present. When the device is activated, compressed gas (curved arrows at bottom) enters the capsule (10). The pressure forces the balls (102) upward, forcing substance above the topmost ball (102) out of the top of the capsule. The topmost ball (102) passes through the top of the capsule into an intermediate space (10A) below the nosepiece (not shown; a shoulder or other barrier (not shown) prevents the balls (102) from exiting the nosepiece. The substance between the first and second balls can then pass through the top of the capsule (10) into the nosepiece (not shown, and mix with the first substance. The second ball (102) can then enter the intermediate space (10A), and similarly with all balls (102) in the capsule (10) until the capsule (10) is empty.

Ball-type barriers (102) are useful when mixing of several components should occur only upon delivery, when one or more substance should be maintained at low humidity, when the viscosity of the substance varies significantly, and any combination thereof. In addition, contact between the ball (102) and the walls of the capsule (10) can also ensure effective release of the substance from the capsule (10). Examples of substances which tend to cling to walls include, but are not limited to, oils and some powders. The barriers can be balls, as in the embodiment shown, angular dividers or any other shape which can be easily moved by the released compressed gas (low-friction contacts), and still provide effective sealing between the elements to avoid mixing during, for example, shipment and storage.

Figure 17C:
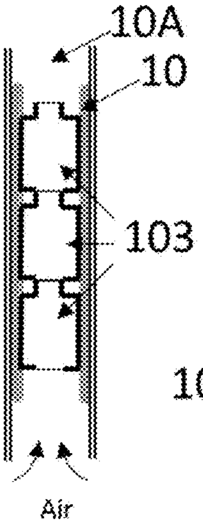

FIG. 17C shows an embodiment with linked drug containers (103) within the capsule (10). In this exemplary embodiment, there are 3 linked drug containers (103). In other embodiments, more or fewer linked drug containers (103) can be present. The linked drug containers (103) are sealed by frangible membranes. A single frangible membrane can seal the top of one drug container (103) and the bottom of the adjacent drug container (103), separate frangible membranes (103) can be used for adjacent ends of drug containers, and any combination thereof. When the device is activated, compressed gas (curved arrows at bottom) enters the capsule (10). The pressure bursts the membranes, allowing mixing and exit into the nosepiece of the substance s within the linked drug containers (103).

In a preferred embodiment, each drug containers (103) is made of a soft thin sheet. The sheet can be a polymeric membrane, a continuous sheet or any other form which is thin enough to be easily torn when desired by the released of the compressed air. All drug containers (103) are connected to each other during manufacturing. Mixing occurs only during activation, with the compressed gas tearing the membranes/sheets dividing the compartments. Once the membranes are torn, the substance s are exposed to the compressed gas, mixed and delivered.

Figure 17D:
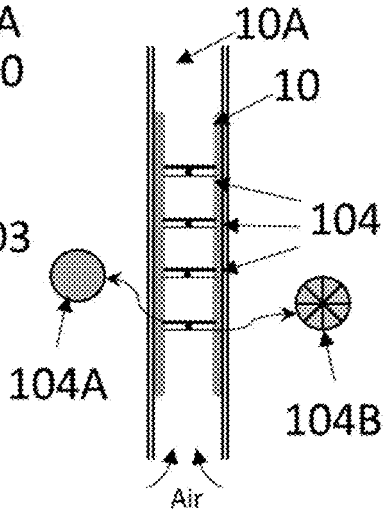

FIG. 17D shows an embodiment with sets of two-layer membranes (104A, 104B) within the capsule (10). In this exemplary embodiment, there are 4 sets of two-layer membranes (104A, 104B). In other embodiments, more or fewer sets of two-layer membranes (104A, 104B) can be present. The lower membrane (104B) is reticulated, with portions separable from each other, and the upper membrane (104A), frangible. When the device is activated, compressed gas (curved arrows at bottom) enters the capsule (10). The pressure causes the separable portions of the lower membrane (104B) to rotate upward, tearing the upper membrane (104A) and allowing mixing and exit into the nosepiece of the substance s within the capsule (10).

This embodiment differs from the previous one in that: (a) the drug containers do not form one unit; (b) the separate zones are separated from each other by membrane which is composed of two layers: one provides the rigidity of the membrane and is made of a rigid material, and the other one is a continuous flexible sheet which seals against the lower rigid part during until activation and which opens when air is pressed against its lower side The membranes (104A, 104B) open only one way, when air presses against their lower side during activation, allowing mixing of the substances during delivery.

Figure 17E:
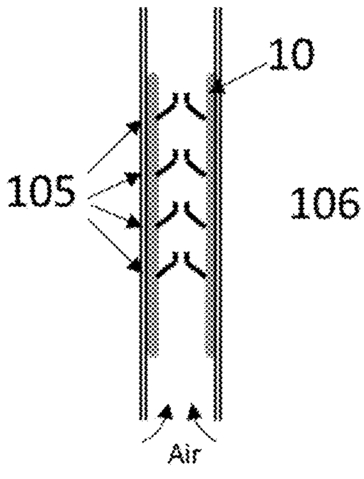

FIG. 17E shows an embodiment with duckbill valves (105) within the capsule (10). In this exemplary embodiment, there are 4 duckbill valves (105). In other embodiments, more or fewer duckbill valves (105) can be present. When the device is activated, compressed gas (curved arrows at bottom) enters the capsule (10). The pressure causes the duckbill valves (105) to rotate upward, allowing exit and mixing of the substance s within the capsule (10).

Figure 17F:
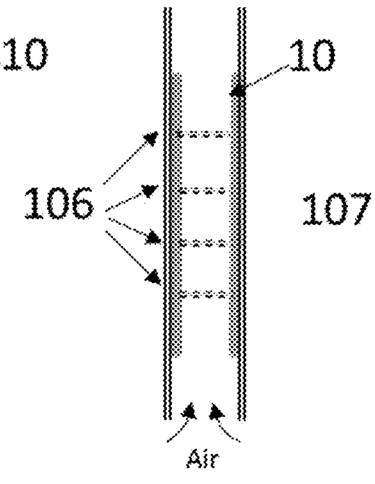

FIG. 17F shows an embodiment with frangible membranes (105) within the capsule (10). In this exemplary embodiment, there are 4 frangible membranes (105). In other embodiments, more or fewer frangible membranes (105) can be present. When the device is activated, compressed gas (curved arrows at bottom) enters the capsule (10). The pressure causes the frangible membranes (105) to tear, allowing mixing and exit into the nosepiece (not shown) of the substance s within the capsule (10).

Figure 17G:
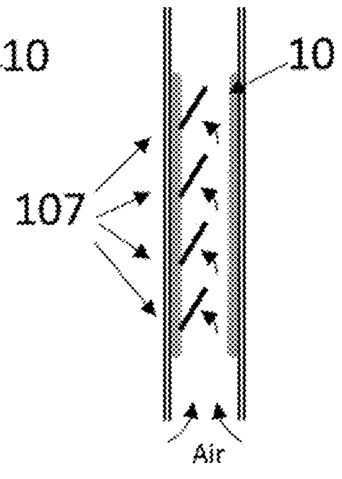

FIG. 17G shows an embodiment with bendable membranes (106) within the capsule (10). In this exemplary embodiment, there are 4 bendable membranes (106). In other embodiments, more or fewer bendable membranes (106) can be present. When the device is activated, compressed gas (curved arrows at bottom) enters the capsule (10). The pressure causes the bendable membranes (106) to rotate upward (curved arrows in middle) about connection points between the bendable membranes (106) and the capsule (10) wall, allowing mixing and exit into the nosepiece (not shown) of the substances within the capsule (10).

These exemplary embodiments allow holding the substances separate during storage and mixing the substances only upon activation and delivery. In some embodiments, the device or the substances therein can be configured to generate a temperature change, either heating or cooling, during mixing and delivery. The device can further be configured so that components for creating a temperature change in the device are not released with the delivered substances.

Heating and cooling can be triggered by mechanical force, by pressure, by chemical reaction and any combination thereof. This can be done inside the drug capsule, around the drug capsule, or outside the device itself in its packaging, to be triggered right before activation of the device.

Such temperature change can be generated during activation (short time temperature change) or prior to activation (long time temperature change). Long time temperature changes require a temperature activation separated from the delivery activation.

Either option, or at least the long time temperature change, further requires proper device sealing to allow temperature to be maintained inside the device and to allow equilibration prior delivery. Such options can further include a temperature indicator, such as by a color change in a dedicated control window, to allow the user to know that the device is ready for activation.

A temperature change can be an increase in temperature, a decrease of temperature, or both.

A temperature change can be useful for example for:

Substance mixing

Dissolution of one substance in another

Absorption of a substance or mixture of substances in tissue, for example, a delivery temperature regulated with respect to the temperature of the nasal passages.

Effective scattering of a substance or mixture of substances on tissue, for example, to create a flat, thin, uniform layer in the nasal passages and hence improve absorption Affect the viscosity of a substance or mixture of substances (both increase and decrease of viscosity can occur).

Affect nature of a substance or mixture of substances. For example: polymerization can be initiated only during delivery, or during or after contact with tissue.

One embodiment comprises two heating agents. These heating agents are in compartments of a capsule. Upon activation of the device, or upon activation of heating (for example, buy pressing a button), a membrane separating the two compartments is torn, allowing the heating agents to mix and to generate heat within the device. Other membranes are not torn by this activity, which keeps the heating agents in a sealed compartment—sealed so as to prevent delivery of heating agent delivery but allow gas passage to other compartments. Passage of the compressed gas then delivers the heated substances or other desired substances. Mixing, as disclosed above, can occur during delivery.

Reference is now made to FIGS. 18*a*-18*f* illustrating another embodiment of the capsule.

Figures 18A, 18B, 18C, 18D, 18E, 18F:
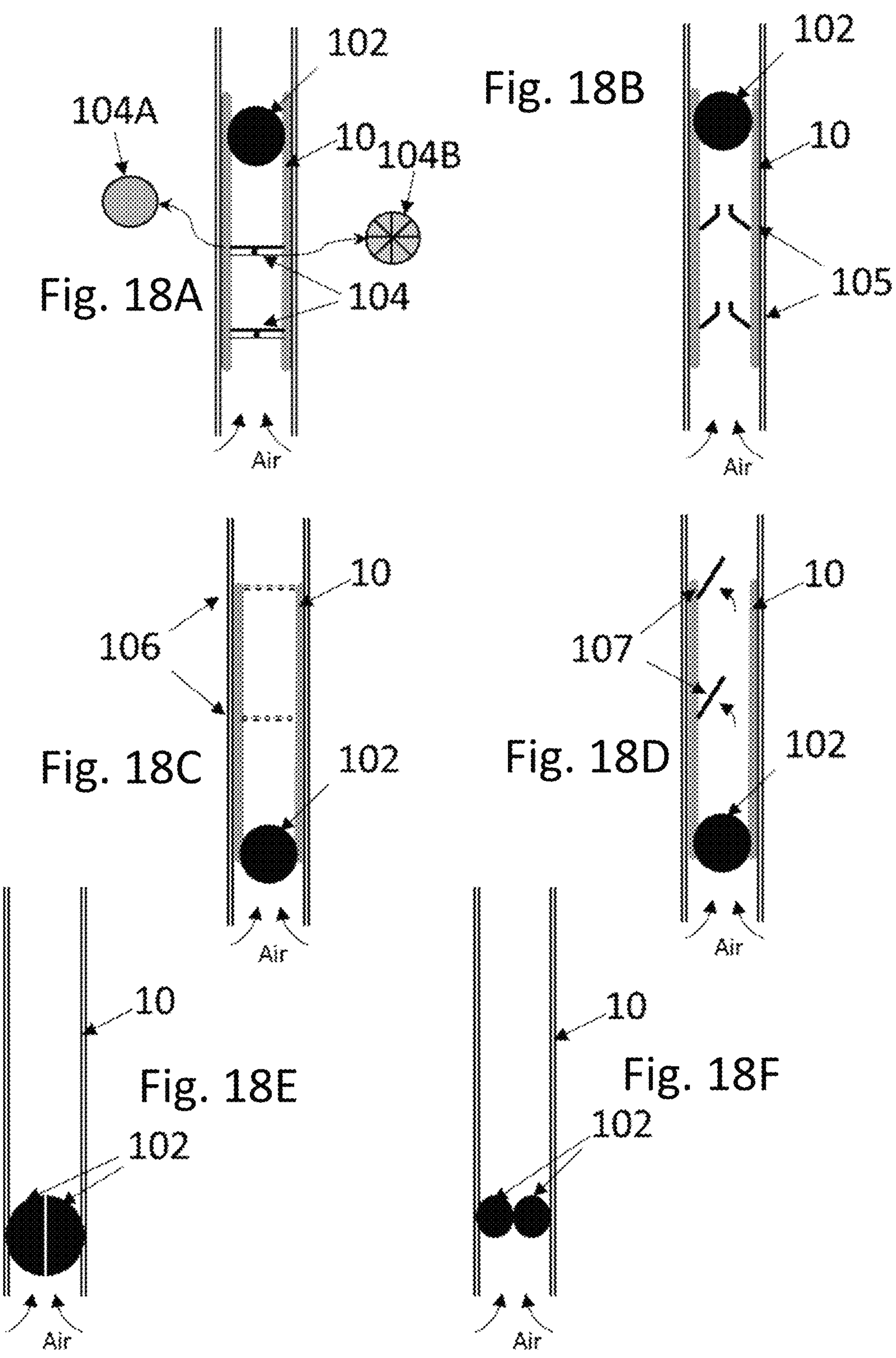

FIG. 18A shows an embodiment with sets of two-layer membranes (104A, 104B) and a mixing ball (102) within the capsule (10). In this exemplary embodiment, there are 2 sets of two-layer membranes (104A, 104B) and a single mixing ball (102) at the top of the capsule (10). In other embodiments, more or fewer sets of two-layer membranes (104A, 104B) and more or fewer mixing balls (102) can be present; the mixing balls (102) can be at any desired location within the capsule (10). The lower membrane (104B) is reticulated, with portions separable from each other, and the upper membrane (104A), frangible. When the device is activated, compressed gas (curved arrows at bottom) enters the capsule (10). The pressure causes the separable portions of the lower membrane (104B) to rotate upward, tearing the upper membrane (104A) and allowing mixing and exit into the nosepiece of the substances within the capsule (10). Further mixing is provided by the mixing ball (102). As disclosed above, a shoulder or other stopper in the nosepiece (not shown) prevents the mixing ball (102) from exiting the nosepiece (not shown).

FIG. 18B shows an embodiment with duckbill valves (105) and a mixing ball (102) within the capsule (10). In this exemplary embodiment, there are 2 duckbill valves (105) and a single mixing ball (102) at the top of the capsule (10). In other embodiments, more or fewer duckbill valves (105) can be present and more or fewer mixing balls (102) can be present; the mixing balls (102) can be at any desired location within the capsule (10). When the device is activated, compressed gas (curved arrows at bottom) enters the capsule (10). The pressure causes the duckbill valves (105) to rotate upward, allowing exit and mixing of the substances within the capsule (10). Further mixing is provided by the mixing ball (102). As disclosed above, a shoulder or other stopper in the nosepiece (not shown) prevents the mixing ball (102) from exiting the nosepiece (not shown).

FIG. 18C shows an embodiment with frangible membranes (105) and a mixing ball (102) within the capsule (10). In this exemplary embodiment, there are 4 frangible membranes (105) and a single mixing ball (102) at the top of the capsule (10). In other embodiments, more or fewer frangible membranes (105) can be present and more or fewer mixing balls (102) can be present; the mixing balls (102) can be at any desired location within the capsule (10). When the device is activated, compressed gas (curved arrows at bottom) enters the capsule (10). The pressure causes the frangible membranes (105) to tear, allowing mixing and exit into the nosepiece (not shown) of the substances within the capsule (10). Further mixing is provided by the mixing ball (102). As disclosed above, a shoulder or other stopper in the nosepiece (not shown) prevents the mixing ball (102) from exiting the nosepiece (not shown).

FIG. 18D shows an embodiment with bendable membranes (106) and a mixing ball (102) within the capsule (10). In this exemplary embodiment, there are 4 bendable membranes (106) and a single mixing ball (102) at the top of the capsule (10). In other embodiments, more or fewer bendable membranes (106) can be present and more or fewer mixing balls (102) can be present; the mixing balls (102) can be at any desired location within the capsule (10). When the device is activated, compressed gas (curved arrows at bottom) enters the capsule (10). The pressure causes the bendable membranes (106) to rotate upward (curved arrows in middle) about connection points between the bendable membranes (106) and the capsule (10) wall, allowing mixing and exit into the nosepiece (not shown) of the substances within the capsule (10). Further mixing is provided by the mixing ball (102). As disclosed above, a shoulder or other stopper in the nosepiece (not shown) prevents the mixing ball (102) from exiting the nosepiece (not shown).

FIG. 18E shows an embodiment with two half balls (102). In this exemplary embodiment, there is one pair of half-balls (102). In other embodiments, more pairs of half-balls (102) can be present. When the device is activated, compressed gas (curved arrows at bottom) enters the capsule (10). The pressure causes the half-balls (102) to move upward. They will separate and tumble as they move, allowing gas to pass between and around them thus mixing and delivering the substance. As disclosed above, a shoulder or other stopper in the nosepiece (not shown) prevents the mixing ball (102) from exiting the nosepiece (not shown).

FIG. 18F shows an embodiment with two attached mixing balls (102). In other embodiments, more mixing balls (102) can be present. When the device is activated, compressed gas (curved arrows at bottom) enters the capsule (10). The pressure causes the mixing balls (102) to move upward, thus causing efficient mixing of the substances. As disclosed above, a shoulder or other stopper in the nosepiece (not shown) prevents the mixing ball (102) from exiting the nosepiece (not shown).

The mixing balls need not be spherical; any shape that will provide good sealing during storage and low-friction movement during activation can be used.

Figure 19:
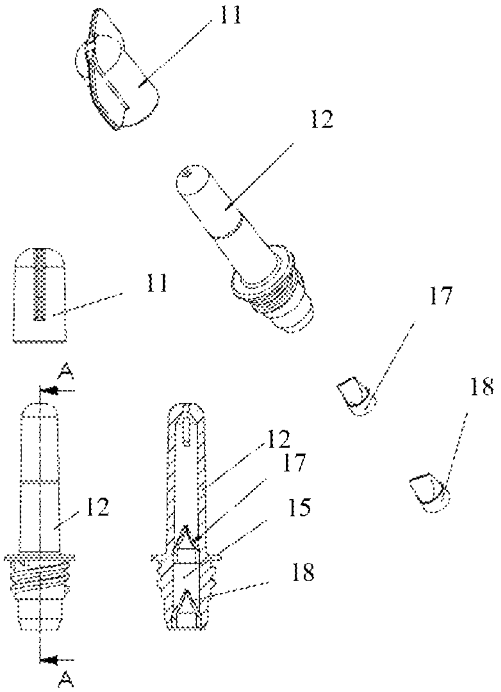

Reference is now made to FIG. 19, which illustrates a closer view of another embodiment of the capsule. According to this embodiment, the capsule comprises at least one uni-directional valve such as duckbill valve. In the embodiment illustrated in FIG. 19 two uni-directional valve (e.g., duckbill valves), 17 and 18 are provided, where the medicament 15 is disposed therebetween.

As noted above, the medicament delivered can either powder, liquids, gas, gel and any mixing thereof.

Figure 20:
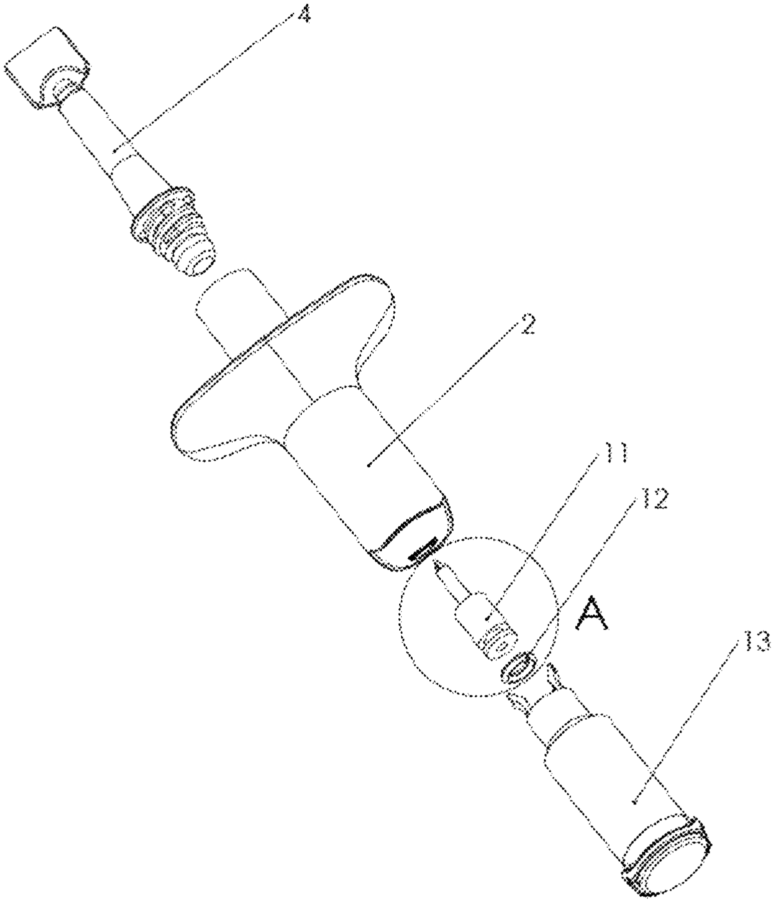
FIGS. 20-24*d* show another embodiment of the present invention.
Figure 21:
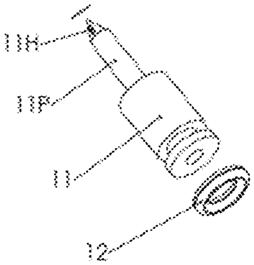

Reference is now made to FIGS. 20-21 which illustrates another embodiment of the present invention in which piercing of the medicament container is disclosed. FIG. 20 illustrates the device according to this embodiment, where 4 is the nosepiece, 2 is the device's body, 11 is a hollow piercing element, 13 is the pressurized gas container and 12 is a sealing element (preferably an o-ring) sealing the pressurized gas container 13.

FIG. 21 illustrates a closer view of the hollow piercing element 11. According to this embodiment the hollow piercing element 11 comprising (a) a hollow sharp end 11P having at least one orifice 11H (throughout which the pressurized gas will exit the hollow piercing element 11 and enter the medicament container, as will be disclosed hereinafter); and, (b) a proximal end (close to the pressurized gas container). According to one embedment, the proximal end of the hollow piercing element 11 has at least groove along the circumference thereof upon which at least one o-ring rests to provide sealing of the pressurized gas container 13. The two ends of the hollow piercing element 11 are interconnected by a hollow tube.

Figure 22:
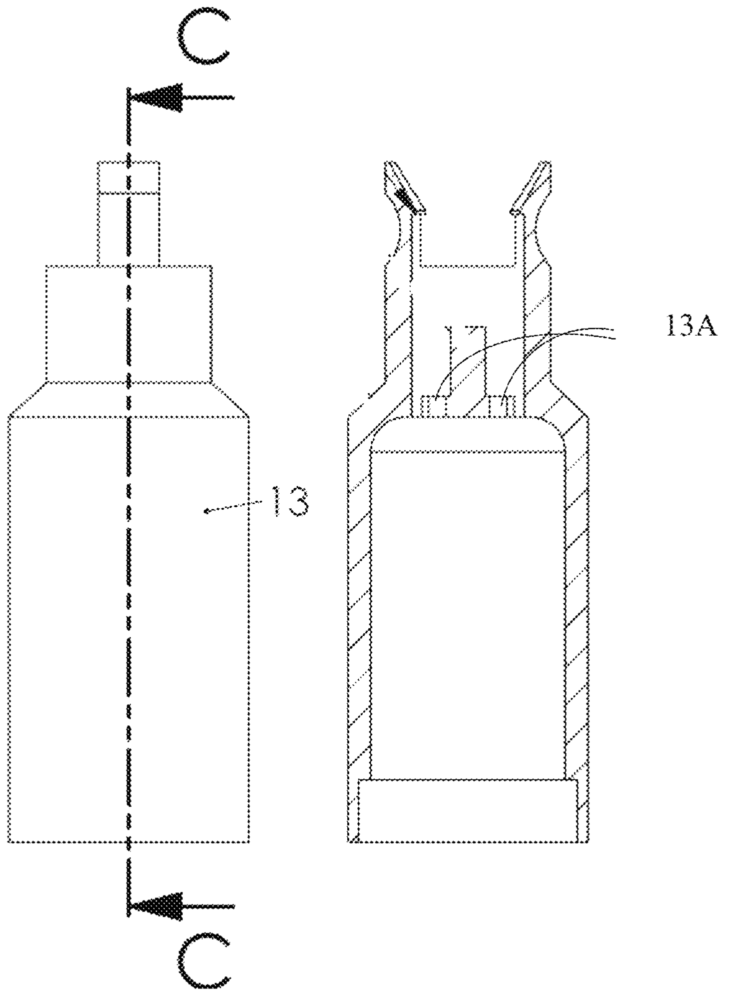

Reference is now made to FIG. 22 which illustrates the pressurized gas container 13. According to this embodiment, the pressurized gas container 13 comprises at least one orifices 13A (throughout which the pressurized gas exits). In the FIG. 22, two orifices 13A are illustrated.

Reference is now made to FIGS. 23*a*-23*d*, which illustrate the mechanism of action of the device according to the present embodiment.

Figure 23A:
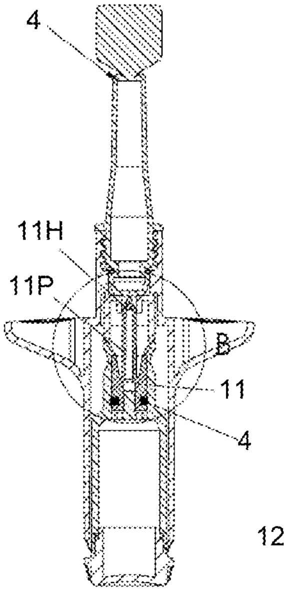
Figure 23B:
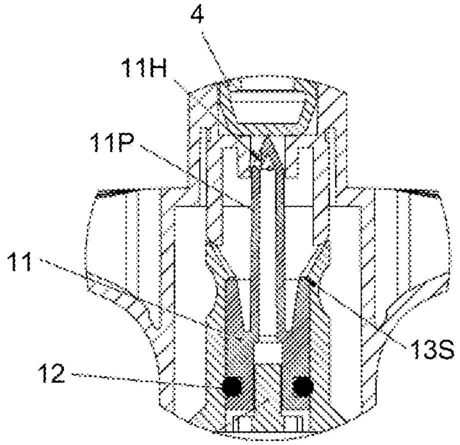

FIGS. 23*a*-23*b* illustrate the device before activation (i.e. before the hollow piercing element 11 pierced the medicament container in the nosepiece 4). In the FIGS. the hollow piercing element 11 with the hollow sharp end 11P having at least one orifice 11H are shown. Also shown is the o-ring 12 disposed in the proximal end thereof. FIG. 23*b* is a closer view of the hollow piercing element 11 before piercing the nosepiece 4 and the medicament capsule therewithin. Before activation of the device (i.e., pressing on the pressurized gas container 13), the bottom end of the hollow piercing element 11 seals the orifices 13A of the pressurized gas container 13 and prevent release of said pressurized gas.

Numerical reference 13S illustrates a stoper element that ensures the hollow piercing element 11 is not piercing the medicament container before activation.

Figure 23C:
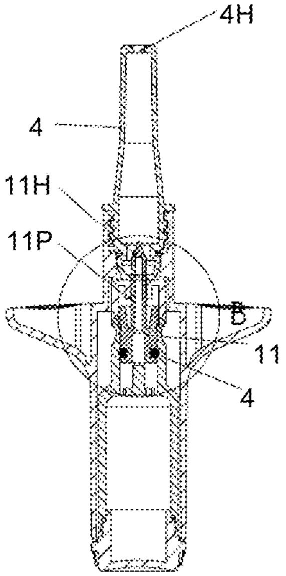
Figure 23D:
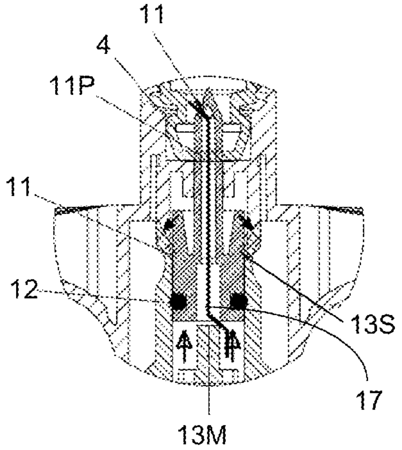

FIGS. 23*c*-23*d* illustrate the device after activation (i.e. after the hollow piercing element 11 pierced the medicament container in the nosepiece 4). In the FIGS., after the pressurized gas container has been pressed, the hollow piercing element 11 has pierced the nosepiece 4, and the bottom end of the hollow piercing element 11 is moved from it position, such that the sealing of the orifices 13M of the pressurized gas container 13 is removed and the release of said pressurized gas from the pressurized gas container 13 is enabled through orifices 13A.

Once the pressurized gas exits from the orifices 13A, it enters the hollow tube of the hollow piercing element 11 and exits thereof from orifice 11H in the sharp end 11P into the medicament container in the nosepiece 4. The pathway of the pressurized air is illustrated by numerical reference 17.

FIG. 23*d* is a closer view of the hollow piercing element 11 after piercing the nosepiece 4 and the medicament capsule therewithin and pathway of the pressurized air exiting the orifices 13A pressurized gas container 13 and entering the medicament container.

According to this embodiment, illustrated in FIGS. 23*a*-23*d*, the capsule encloses a liquid medicament. However, as described above, also powder medicament are enabled and the mixing thereof.

Figure 24A:
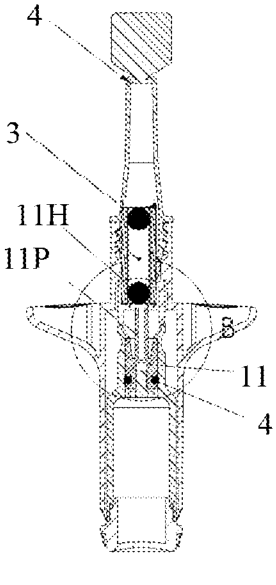

FIGS. 24*a*-24*d* illustrates the piercing mechanism utilized with a powder medicament. According to this embodiment, the nosepiece encloses a capsule with at least one spherical element 13. In FIG. 24*a*, two spherical elements 13 are illustrated, one at the bottom most part of the capsule and the other at the upper most part. The medicament is disposed therebetween.

As described above, after the pressurized gas container has been pressed, the hollow piercing element 11 has pierced the nosepiece 4, and the bottom end of the hollow piercing element 11 is moved from it position, such that the sealing of the orifices 13M of the pressurized gas container 13 is removed and the release of said pressurized gas from the pressurized gas container 13 is enabled through orifices 13A.

Figure 24B:
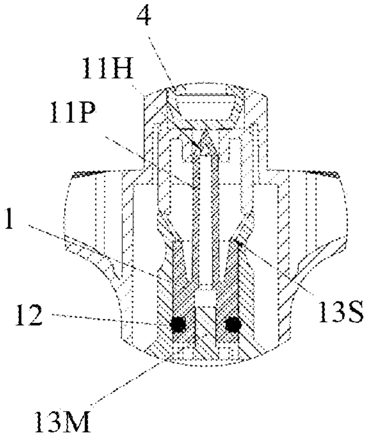

Once the pressurized gas exits from the orifices 13A, it enters the hollow tube of the hollow piercing element 11 and exits thereof from orifice 11H in the sharp end 11P into the medicament container in the nosepiece 4. Such pressurized gas removes the bottom most spherical element 13 from its position to compress the medicament until the pressure reaches the upper most spherical element to remove it from its position. Once the two spherical elements are removed, the medicament and the pressurized gas are mixed and delivered to the nasal cavity. FIG. 24*b* is a closer view of the hollow piercing element 11 before piercing the nosepiece 4.

Figure 24C:
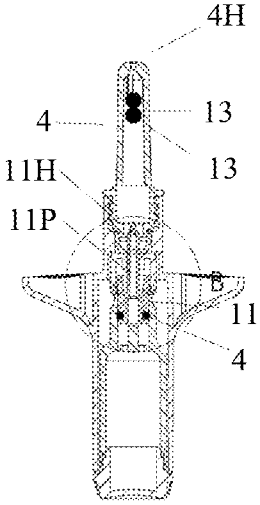
Figure 24D:
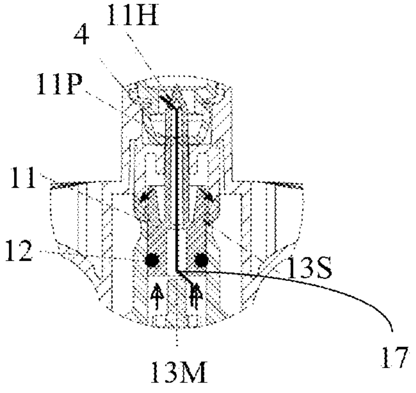
Figure 25:
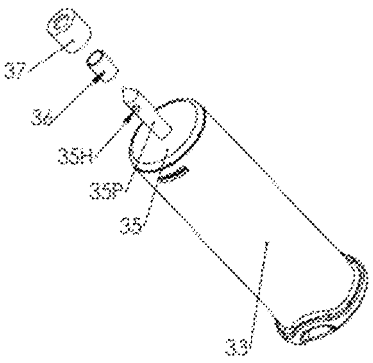

Reference is now made to FIGS. 24*c*-24*d* which illustrate the device after activation (i.e. after the hollow piercing element 11 pierced the medicament container in the nosepiece 4). As detailed above, once the pressurized gas container has been pressed, the hollow piercing element 11 has pierced the nosepiece 4, and the bottom end of the hollow piercing element 11 is moved from it position, such that the sealing of the orifices 13A of the pressurized gas container 13 is removed and the release of said pressurized gas from the pressurized gas container 13 is enabled through orifices 13A.

Once the pressurized gas exits from the orifices 13A, it enters the hollow tube of the hollow piercing element 11 and exits thereof from orifice 11H in the sharp end 11P into the medicament container in the nosepiece 4 to remove the spherical element/s. The pathway of the pressurized air is illustrated by numerical reference 17. FIG. 24*d* is a closer view of the hollow piercing element 11 after piercing the nosepiece 4 and the pressurized gas pathway.

It should be noted that a variety of capsule and sealing means (other than the spherical element) can be utilized. Several examples are provided in FIGS. 17*a*-17*g* and FIGS. 18*a*-18*f*.

Reference is now made to FIGS. 25-30*d* which illustrates another embodiment of the piercing mechanism.

According to this embodiment, the pressurized gas container 33 having an upper surface 35 integrated with a hollow extension body 35P and a sharp end with at least one orifice 35H along the body 35P or at the upper most end of the hollow extension 35. A septum 36 is provided to seal said at least one orifice 35H. An optional septum cover 37 is placed on the septum in a tight manner in order to insure sealing before activation.

Figure 26A:
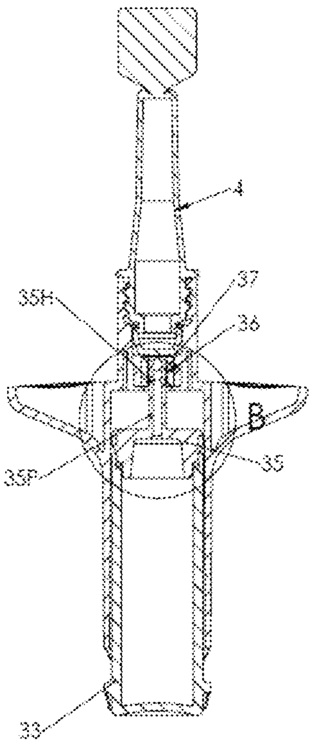
Figure 26B:
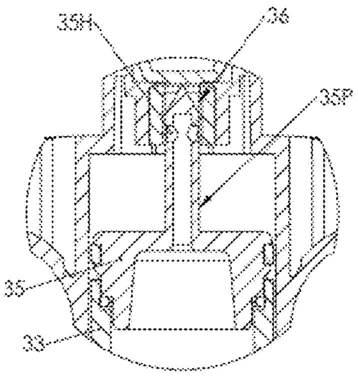

Reference is now made to FIGS. 26*a*-26*b* which illustrates the above disclosed embodiment, prior to activation. As can be seen from FIG. 26*a*, prior to pressing on the pressurized gas container 33, the hollow extension 35 has not yet pierced the nosepiece 4 and the medicament container. FIG. 26*b* provides a closer view of the hollow extension 35. As can be seen from the FIG. the orifice 35H of the hollow extension 35 is sealed with septum 36 and its optional cover 37, such that the pressurized gas from the pressurized gas container 33 is prevented from escaping therefrom.

Figure 26C:
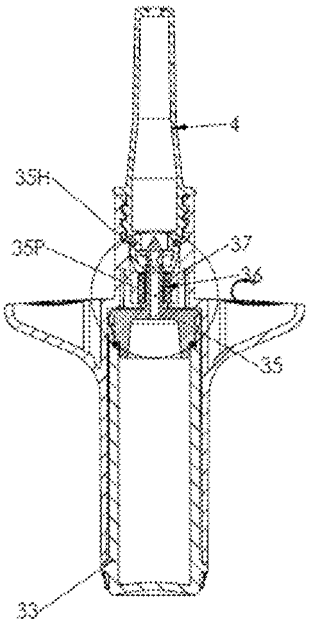
Figure 26D:
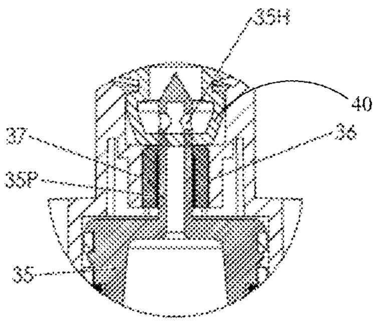

Reference is now made to FIGS. 26*c*-26*d* which the above disclosed embodiment, post to activation (i.e., after piercing of the nosepiece). As can be seen from the FIGS., once the pressurized gas container has been activated (i.e., pressed), the hollow extension 35 is pushed towards the nosepiece. Such movement results in: (a) piercing of the capsule within the nosepiece 4 by means of the sharp end of the hollow extension 35; and, (b) the hollow extension 35 moves through the septum 36 and its cover 37 (those are static in the device and cannot move), and thus the orifice 35H is being exposed (uncovered) to enable a fluid communication between the pressurized gas container 33 and the capsule.

Figure 27A:
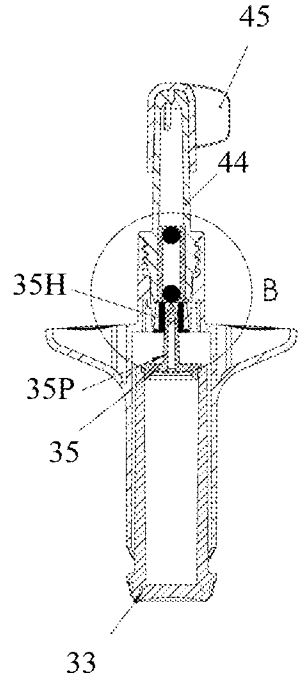
Figure 27B:
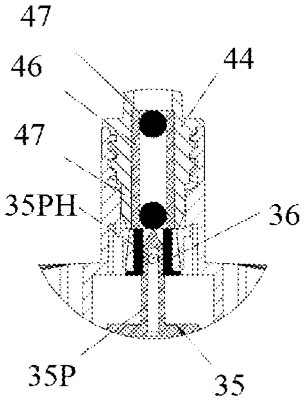

Reference is now made to FIGS. 27*a*-27*d* illustrating the above embodiment utilizing a capsule 46 dedicated to either powder or liquid medicaments. In such capsule at least one spherical element 47 is utilized. The capsule 46 illustrated in FIG. 27 employs 2 spherical elements 47. One positioned at the bottom most part of the capsule and the other at the uppermost part. The medicament is positioned therebetween. FIGS. 27*a*-27*b* illustrated this embodiment prior to activation of the device.

It should be noted that should the capsule enclose several spherical elements 47 the same can be used as divider to enclose several liquid medicaments, several powder medicaments or any combination of both liquid and powder medicaments. It is further noted that the spherical elements 47 can be replaced with a membrane adapted to divide the capsule to several 'compartments'.

It should further be noted that the hollow extension 35 can be used to remove the sealing of the capsule (in this case, the spherical element) or to pierce the capsule.

Figure 27C:
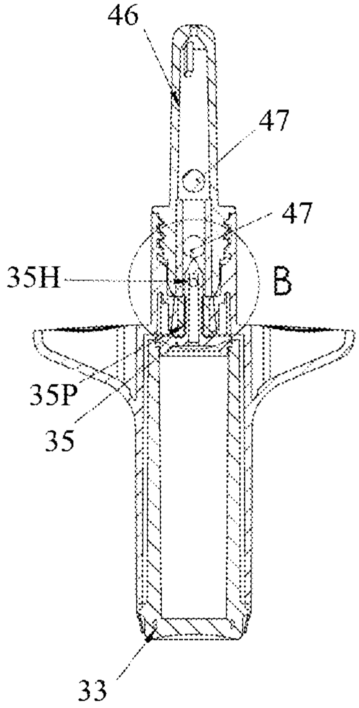
Figure 27D:
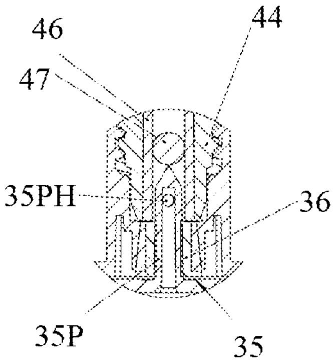

Reference is now made to FIGS. 27*c*-27*d* illustrating said embodiment post activation (i.e., after the hollow extension 35 either pierced the nosepiece mechanically or released the compressed air in a manner that results in the opening of the barrier element in the capsule or nosepiece, such as the spherical element and/or membrane), to deliver a powder or liquid or any combination thereof medicament. Thus, it should be emphasized that it could very well be that the hollow extension 35 does not pierce the nosepiece but merely removes the sealing thereof (in this case the spherical element).

Once the pressurized gas container 33 is actuated (i.e., pressed), the hollow extension 35 is pushed towards the nosepiece. Such movement results in: (a) piercing of the capsule within the nosepiece 4 by means of the sharp end of the hollow extension 35; or removing the sealing element, which is, in this case, the spherical element; and, (b) the hollow extension 35 moves through the septum 36 and its cover 37 (those are static in the device and cannot move), and thus the orifice 35H is being exposed (uncovered) to enable a fluid communication between the pressurized gas container 33 and the capsule. In such a case, where powder or liquid medicament is utilized, the pressurized gas first remove bottom most spherical element 47, which in turn compress the medicament (positioned between the two spherical elements 47) until max. Compression is reached and then the uppermost spherical element 47 is removed, where only then, the medicament and the pressurized gas come in contact, mix and being delivered . . . FIG. 27*d* provides a closer view of the piercing by means of hollow extension 35.

Reference is now made to FIGS. 28*a*-28*d* illustrating another embodiment as described in FIGS. 27*a*-27*d* but with one spherical element 47, positioned in the bottom most part of the capsule.

Figure 28A:
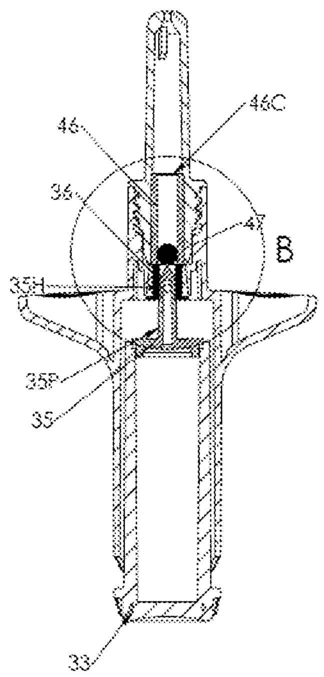
Figure 28B:
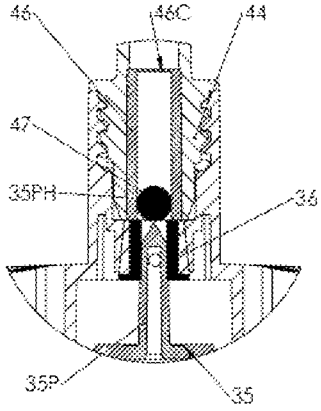
Figure 28C:
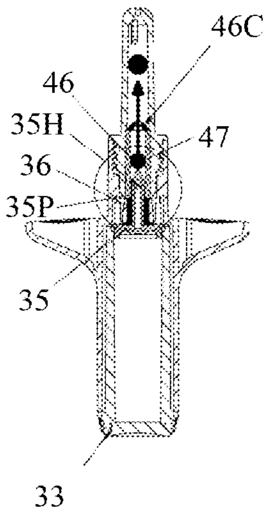
Figure 28D:
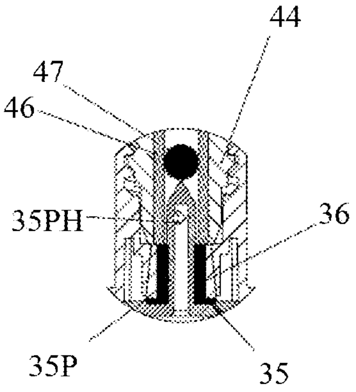

FIGS. 28*a*-28*b* illustrates the device before activation and piercing of the capsule and FIGS. 28*c*-28*d* illustrates the device after activation and piercing of the capsule 46 in the nosepiece 44. In the embodiment illustrated in FIG. 28*b* the capsule is also illustrated with a membrane 46C that enables the disposition of either liquids or powder medicaments (or any mix/combination thereof).

Reference is now made to FIG. 29 illustrating one way valve embodied as a duckbill (similarly to FIG. 19).

FIGS. 30*a*-30*d* illustrating the device utilizing a unidirectional valve (such as a Duckbill) as the area to hold and store the drug (liquid/powder) prior to activation. Before the activation (FIGS. 30*a*-30*b*) the drug is stored in a closed area between the valves (in some cases only one valve can be used). After activation (FIGS. 30*c*-30*d*), the air flow from the pressurized air container is discharged trough the valve/s to release the drug via the nosepiece in the same manner as described for FIGS. 27-28.

It should be noted that the capsule could utilize several embodiments, e.g., the embodiments described in FIGS. 17*a*-17*g* and FIGS. 18*a*-18*f*.

Figure 31:
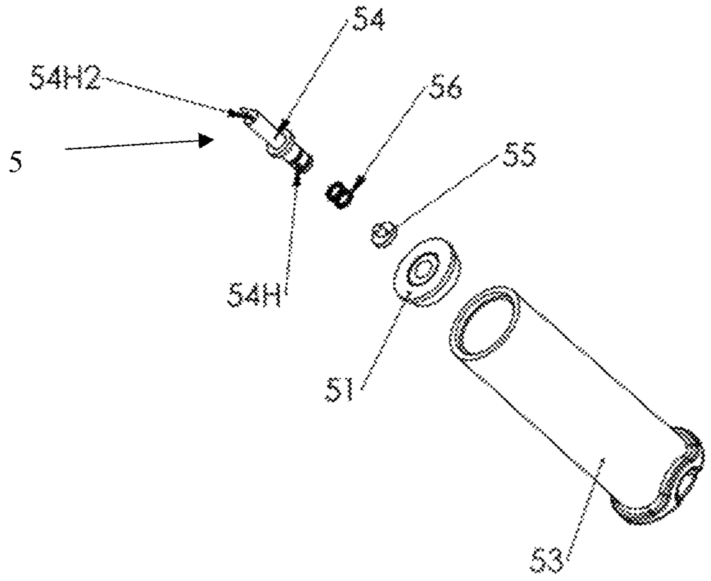
FIGS. 31-32*c* show another embodiment of the present invention.

Reference is now made to FIG. 31 which illustrates another embodiment of the present invention in which the hollow piercing element 5 which comprises (a) a hollow sharp end having at least one orifice 54H2 (throughout which the pressurized gas will exit the hollow piercing element 5 and enter the medicament container, as will be disclosed hereinafter); and, (b) a proximal end (close to the pressurized gas container). According to one embedment, the proximal end of the hollow piercing element 5 has at least one groove along the circumference thereof upon which at least one o-ring 56 rests to provide sealing of the pressurized gas container 13 to prevent any pressurized gas from exiting the pressurized gas container 53 before activation thereof. The two ends of the hollow piercing element 5 are interconnected by a hollow tube 54.

According to one embedment, the proximal end of the hollow piercing element 5 has at least one orifice 54H (throughout which the pressurized gas will exit the pressurized gas container 53 and enter the hollow piercing element 5, as will be disclosed hereinafter).

Numerical reference no. 51 refers to the pressurized gas container 53's cover so as to prevent leakage therefrom.

Numerical reference no. 55 is adapted to seal the bottom side of the hollow tube 54.

Figure 32A:
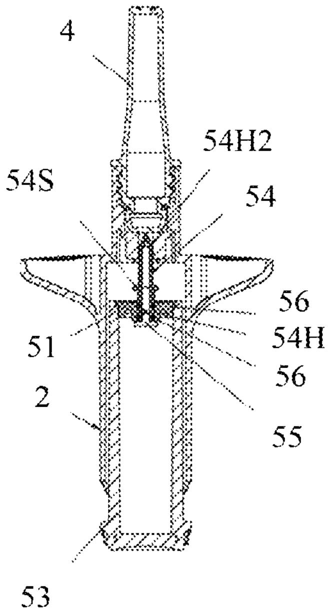

Reference is now made to FIG. 32*a* which illustrates the device before activation (i.e. before the hollow piercing element 5 pierced the medicament container in the nosepiece 4). As seen from the figure, before the bottom end of the pressurized gas container has been pressed the hollow piercing element 5 has not yet pierced the nosepiece 4. In this position, the at least one orifice 54H in the proximal end of the hollow piercing element 5 is placed above (i.e., outside) the pressurized gas container thus, maintain the pressurized gas container sealed. Furthermore, the at least one orifice 54H2 in the hollow sharp end of the hollow piercing element 5 is below (i.e., outside) the nosepiece.

Figure 32B:
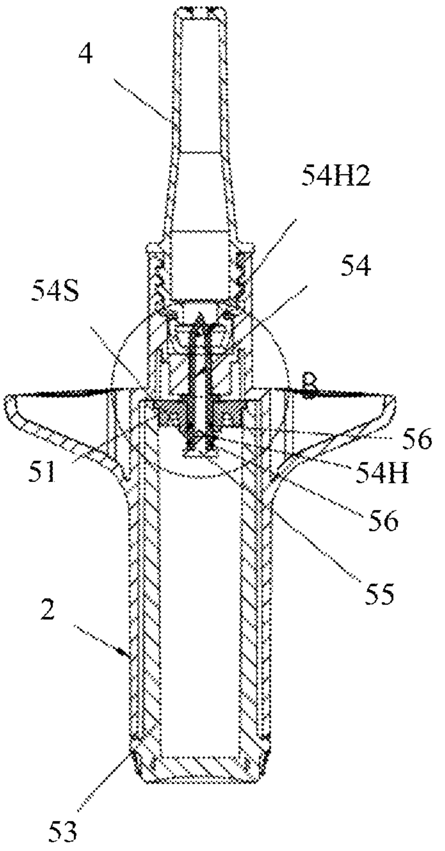
Figure 32C:
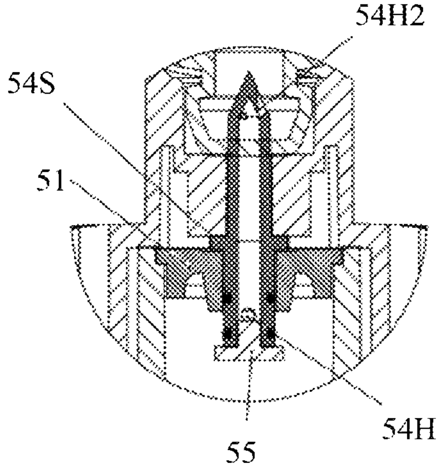

Reference is now made to FIGS. 32*b*-32*c* which illustrate the device after activation thereof. As detailed above, once the pressurized gas container has been pressed, the bottom most part 55 of hollow piercing element 5 is now positioned within the pressurized gas container. In this position, the orifice 54H (in the proximal end thereof) is disposed within the pressurized gas container thus, pressurized fluid (gas) can exit the pressurized gas container and enter the hollow piercing element 5 through orifice 54H. Substantially at the same, the sharp end of the hollow piercing element 5 pierced the nosepiece 4, and at least one orifice 54H2 is now disposed within the nosepiece (and the medicament capsule). Thus, the pressurized fluid (gas) can exit the hollow tube 54 of the hollow piercing element 5 from at least one orifice 54H2 and enter the nosepiece (and the medicament capsule) to entrain the medicament and deliver the same to the nasal cavity.

Figure 34C:
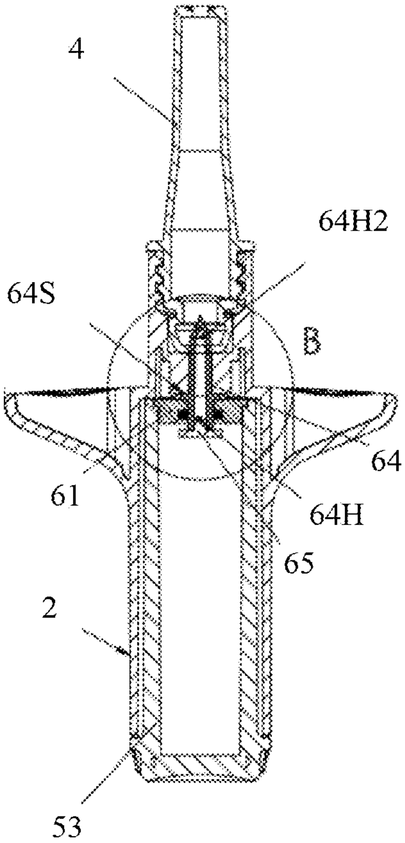
Figure 34D:
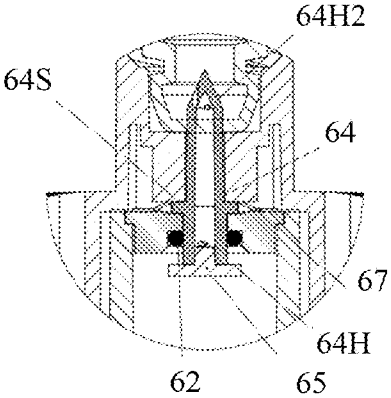
Figure 35A:
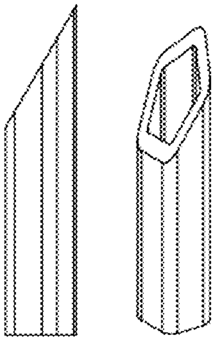
FIGS. 35*a*-35*d* illustrating different embodiments of the hollow needle.
Figure 35B:
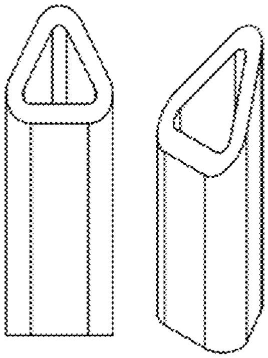
Figure 35C:
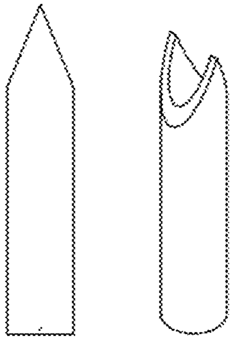
Figure 35D:
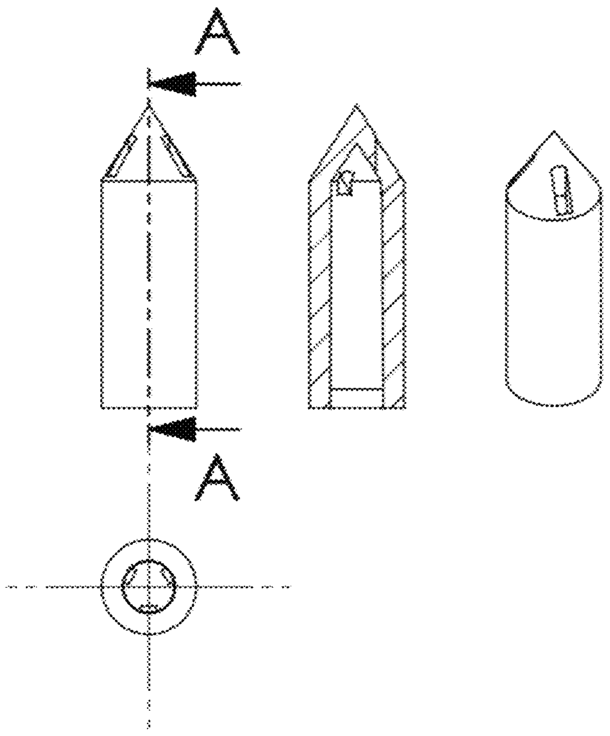

Reference is now made to FIGS. 33-34*d* illustrating another embodiment of the present invention in which a spring 67 is utilized. In this embodiment, the hollow needle 64 has at least one orifice 64H2 in the upper end thereof, adapted to enable the release of the medicament to the nose. Needle 64 has at least one orifice 64H at the bottom most part thereof. Throughout which the pressurized gas exits the pressurized gas container and enter the hollow needle to eventually enter the capsule and entrain the medicament to be delivered to the nasal cavity.

FIGS. 34*a*-34*b* illustrates the device before activation (where FIG. 34*b* provides a closer view of the needle 64) and 34*c*-34*d* illustrates the device after activation (where FIG. 34*d* provides a closer view of the needle 64).

As seen in the FIGS. 34*a*-34*b*, before activation of the device, orifice 64H is outside the pressurized gas container 53 and prevents the pressurized gas from exiting therefrom; and orifice 64H2 is outside the capsule in the nosepiece.

Once the bottom most part of the pressurized gas has been pressed, shoulders 64*s* presses spring 67 and the orifice 64H on the bottom of the needle being exposed. Furthermore, orifice 64H2 penetrates the capsule to enable the exit of the pressurized air from the hollow needle 64 to the capsule.

Reference is now made to FIGS. 35*a*-35*d* illustrating different shapes of hollow needle. As can be seen from the FIGS. the sharp end of the needle can have a cross section of any shape (e.g., rectangular, triangular, pentagon etc.). Each wig of the needle can accommodate at least one orifice, throughout which the pressurized gas can exit and enter the capsule and entrain the medicament to be delivered to the nasal cavity.

According to any of the embodiment as described above, the pressurized gas container can be mad of at least one material selected from a group consisting of high- or low-density polyethylene, high- or low-density polypropylene, any plastic resin, glass, plastics, Aluminum and any combination thereof.

Figure 36A:
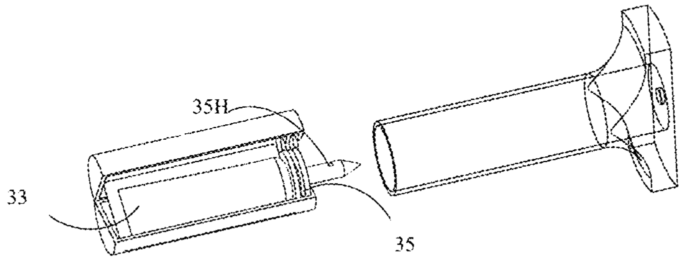
FIG. 36*a*-36*b* illustrating another embodiment of the present invention.
Figure 36B:
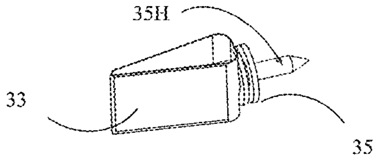

Reference is now made to FIGS. 36*a*-36*b*, illustrating another embodiment of the present invention, in which the pressurized-fluid container (enclosing the pressurized and compressed fluid) is made of material being a high barrier film. According to one embodiment the high barrier film is a high barrier Aluminum film.

According to this embodiment, the high barrier film (e.g., Aluminum film) is ultrasonic soldered to create the pressurized-fluid container. Such ultrasonic soldering of the Aluminum high barrier film results in an airtight container that prevents any air leakage of the compressed and pressurized gas therewithin.

Reference is now made to FIG. 36*a* which illustrates the container 33 (ultrasonic soldering) along with the upper surface 35 integrated with a hollow extension body 35P (not shown) and a sharp end with at least one orifice 35H along the body 35P or at the upper most end of the hollow extension 35. FIG. 36*b* illustrates a closer view thereof.

It should be emphasized that surface 35 is sealable welded to the upper surface of the container.

The invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for delivering either one or more substances within at least one body cavity, comprising:

(i) at least one nosepiece comprising at least one capsule comprising $V_{sub}$ [ml or mg] of said one or more substances; said at least one capsule having at least one fluid inlet port of diameter Din [mm] and at least one fluid discharging outlet of diameter $D_{out}$ [mm], configured for placement in proximity to said at least one body cavity;

(ii) at least one base in communication with said at least one nosepiece, said at least one base comprises at least one chamber configured to confine compressed and pressurized fluid at volume $V_{PF}$ [ml] and pressure $P_{PF}$ [barg];

(iii) at least one hollow puncturing member; said at least one hollow puncturing member is characterized by a first end comprising at least one sharp end and a second end in fluid communication with said at least one base; said first end and second end being fluidly interconnected by at least one hollow tube; said at least one fluid inlet port of said at least one capsule is configured by means of size and shape to interface in a sealable manner with said at least one sharp end of said at least one puncturing member;

wherein actuation of said at least one base is configured to enable piercing of said at least one capsule to provide said at least one fluid inlet port, by means of said at least one sharp end of said at least one hollow puncturing member to enable the pressurized fluid to exit said at least one chamber and entrain through said at least one hollow tube of said at least one hollow puncturing member to said at least one capsule, entrain said one or more substances and deliver said one or more substances to said at least one body cavity;

wherein said at least one sharp end comprises at least one orifice through which said pressurized fluid enters said at least one capsule; and (iv) at least one sealing septum, said at least one sealing septum configured to, prior to actuation of said at least one base, surround and seal said at least one orifice.

2. The device of claim 1, wherein actuation of said at least one base comprises pressing on said at least one base.

3. The device of claim 1, wherein said second end of said at least one hollow puncturing member and said at least one chamber are formed as a single unit, such that an upper surface of said at least one chamber is integrated with said second end of said at least one hollow puncturing member.

4. The device of claim 1, wherein upon actuation of said device, said at least one sealing septum is removed to enable exit of said pressurized fluid through said at least one orifice in said at least one hollow puncturing member.

5. The device of claim 4, wherein upon actuation of said device, said at least one base is pressed and said at least one hollow puncturing member is pushed towards said at least one nosepiece such that a bottom most part of said at least one nosepiece removes said at least one sealing septum from enclosing said at least one orifice in said at least one sharp end of said at least one hollow puncturing member.

6. The device of claim 1, wherein said at least one chamber comprising at least one orifice through which said pressurized fluid exits said at least one chamber.

7. The device of claim 6, wherein upon actuation of said device said sealing of said at least one orifice of said at least one chamber is removed, such that said pressurized fluid exits through said at least one orifice of said at least one chamber into said at least one hollow tube of said at least one hollow puncturing member.

8. The device of claim 1, wherein said second end of said at least one hollow puncturing member seals said at least one orifice of said at least one chamber, prior to actuation of said device.

9. The device of claim 1, wherein said at least one nosepiece comprising at least one nosepiece cover configured by means of size and shape to cover, in a sealable manner, at least partially said at least one nosepiece.

10. The device of claim 9, wherein said at least one nosepiece cover and said at least one nosepiece are coupled to each other.

11. The device of claim 10, wherein said coupling between said at least one nosepiece cover and said at least one nosepiece is reversible.

12. The device of claim 9, wherein said at least one nosepiece comprises at least one port through which said one or more substances exits said device, such that said at least one nosepiece cover seals said at least one port and removal thereof removes said seal.

13. The device of claim 12, wherein said at least one nosepiece cover is configured to provide an air-tight closure for said at least one port, said at least one nosepiece cover slidable along said device, rotatable around said device, rotatable around a hinge on the exterior of said device and any combination thereof.

14. The device of claim 1, wherein said at least one capsule is selected from a group consisting of pierceable container, a blow-fill-seal and a form-fill-seal and any combination thereof.

15. The device of claim 1, wherein said at least one chamber is a container adapted to hold said pressurized fluid at said pressure $P_{PF}$ for a period of time.

16. The device of claim 1, wherein said at least one capsule is made of at least one material selected from a group consisting of high- or low-density polyethylene, high- or low-density polypropylene, any plastic resin, glass and any combination thereof.

17. The device of claim 1, wherein said volume $V_{PF}$ [ml] of said pressurized fluid at pressure $P_{PF}$ [barg] is configured to be released from said at least one chamber within a period of time less than 500 milliseconds (dT), via said at least one fluid inlet port, such that said pressurized fluid entrains said one or more substances and erupts via said at least one fluid discharging outlet into said at least one body cavity, wherein the release time of said $V_{sub}$ [ml or mg] of said one or more substances and said $V_{PF}$ [ml] of said pressurized fluid, $dT_{release}$ is less than 500 milliseconds.

18. The device of claim 1, wherein said device is configured to deliver said $V_{sub}$ substance and $V_{PF}$ pressurized fluid through said at least one fluid discharging outlet of diameter D [mm] wherein at least one of the following is held true:

a) $V_{PF}$ is in a range of 1 to 50 ml;

b) $V_{sub}$ is in a range of about 0.01 to about 7 ml;

c) $D_{in}$ and/or $D_{out}$ is in a range of 0.2 to 6 mm;

d) $P_{PF}$ is in a range of about 0 to about 10 barg;

e) a pressure velocity is greater than 0.001 barg/ms;

f) said pressure velocity is greater than 0.01 barg/ms;

g) a volume rate $dV_{sub}/dT$ or $dV_{sub}/dT_{release}$ is greater than 0.0001 ml/ms;

h) said volume rate $dV_{sub}/dT$ or $dV_{sub}/dT_{release}$ is greater than 0.001 ml/ms;

i) a volume rate $dV_{PF}/dT$ or $dV_{PF}/dT_{release}$ is greater than 0.001 ml/ms;

j) said volume rate $dV_{PF}/dT$ or $dV_{PF}/dT_{release}$ is greater than 0.01 ml/ms;

k) any combination thereof.

19. The device of claim 1, wherein at least one of the following is true:

a) said at least one body cavity is selected from a group consisting of a nasal cavity, a mouth, a throat, an ear, an eye, a vagina, a rectum, a urethra, and any combination thereof, b) said pressurized fluid comprises pressurized gas, wherein said pressurized gas is selected from a group consisting of air, nitrogen, oxygen, carbon dioxide, helium, neon, xenon, nitric oxide and any combination thereof;

c) during dispensing of said one or more substances, a mixture of a predetermined volume $V_{gas}$ [ml] of said pressurized gas with said predetermined volume $V_{sub}$ [ml or mg] of said one or more substances entrained within it forms a plume of aerosol; said aerosol having a predetermined distribution, said distribution being either homogeneous or heterogeneous, said heterogeneous distribution is selected from a group consisting of: an arbitrary distribution, a distribution in which the density of said one or more substances within said mixture follows a predetermined pattern, and any combination thereof; characteristics of said aerosol selected from a group consisting of:

particle size, particle shape, particle distribution, and any combination thereof, are determinable from characteristics of said device selected from a group consisting of: said predetermined volume of said pressurized gas, said predetermined volume of said one or more substances, a predetermined pressure of said pressurized gas, a predetermined orifice size, and any combination thereof;

d) at least one of said one or more substances is selected from a group consisting of a gas, a liquid, a powder, an aerosol, a slurry, a gel, a suspension and any combination thereof;

e) at least one of said one or more substances is stored under either an inert atmosphere or under vacuum to prevent reactions during storage;

f) a dose-response curve is substantially linear for brain concentration of said one or more substances when administered nasally via said device; and g) a dose-response curve for brain concentration having a fit selected from a group consisting of logarithmic, parabolic, exponential, sigmoid, power-low, and any combination thereof; of said one or more substances when administered nasally via said device.

20. The device of claim 1, wherein said pressurized fluid is configured to entrain said one or more substances in a pulsed manner, such that a plurality of portions $V_{PF}$ erupts via said at least one fluid discharging outlet to within said at least one body cavity.

21. The device of claim 1, further comprising a safety latch, adapted to prevent accidental operation of said device.

22. The device of claim 1, wherein said one or more substances is selected from a group consisting of proteins; stem-cells; cells, organs, portions, extracts, and isolations thereof; macro-molecules; RNA or other genes and proteins-encoding materials; neurotransmitters; receptor antagonists; hormones; Ketamine; Glucagon; substrates to treat one of the following: anaphylaxis, Parkinson, seizures and opioid overdose; epinephrine; atropine; metoclopramide; naloxone; Esketamine; edaravone; valbenazine; deutetrabenazine; ocrelizumab; safinamide; nusinersen; daclizumab; pimavanserin; aripiprazole lauroxil; cariprazine; brexpiprazole; eslicarbazepine acetate; flutemetamol F18 injection; vortioxetine; dimethyl fumarate; gadoterate meglumine; antibody mediated brain targeting drug delivery including aducanumab, gantenerumab, bapineuzumab, solanezumab, ofatumumab CD20, BIIB033, LCN2, HMGB1; insulin; oxytocin; orexin-A; leptin; benzodiazepine, midazolam; naloxone; perillyl alcohol; camptothecin; phytochemicals including curcumin and chrysin; nucleotides; olanzapine; risperidone; Venlafaxine; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter, midazolam; naloxone; perillyl alcohol; camptothecin; phytochemicals including curcumin and chrysin; nucleotides; olanzapine; risperidone; Venlafaxin; GDF-5; zonisamide; ropinirole; and any esters, salts, derivatives, mixtures, combinations thereof, with or without a carrier, liposomes, lyophilic or water-miscible solvents, surfactants, cells, cells fractions, at a therapeutically effective concentration.

23. The device of claim 1, wherein said at least one capsule is a hollow tube characterized by at least two ends interconnect to each other, at least one of which is positioned proximal to said at least one chamber.

24. The device of claim 23, wherein said at least one capsule comprises at least one spherical element positioned at at least one of said at least two ends, adapted to seal said at least one capsule and prevent leakage of said one or more substances therefrom.

25. The device of claim 23, wherein said at least one capsule comprises two spherical elements, each of which is disposed at each of said at least two ends, such that said one or more substances are positioned therebetween.

26. The device of claim 25, wherein said two spherical elements, once said pressurized fluid exits said at least one chamber, are adapted to mix said one or more substances.

27. The device of claim 23, wherein said at least one capsule comprises at least one membrane positioned at at least one of said at least two ends, adapted to seal said at least one capsule and prevent leakage of said one or more substances therefrom.

28. The device of claim 27, wherein said at least one capsule comprises two membranes, each of which is disposed at each of said at least two ends, such that said one or more substances are positioned therebetween.

29. The device of claim 23, wherein said at least one capsule comprises at least one duckbill valve positioned by at least one of said at least two ends, adapted to seal said at least one capsule and prevent leakage of said one or more substances therefrom.

30. The device of claim 29, wherein said at least one capsule comprises two duckbill valves, each of which is disposed at each of said at least two ends, such that said one or more substances are positioned therebetween.

31. The device of claim 23, wherein said at least one capsule comprises at least one spherical element, membrane, uni-directional valve, duckbill valve and any combination thereof.

32. The device of claim 1, wherein said at least one hollow puncturing member comprises at least one orifice through which said pressurized fluid enters said at least one hollow puncturing member.

33. The device of claim 1, wherein said at least one chamber comprises at least one material selected from a group consisting of high- or low-density polyethylene, high- or low-density polypropylene, any plastic resin, glass, plastics, Aluminum and any combination thereof.

34. A method for delivering either one or more substances within at least one body cavity, comprising:

a) providing:

i) at least one nosepiece comprising at least one capsule comprising $V_{sub}$ [ml or mg] of said one or more substances; said at least one capsule having at least one fluid inlet port of diameter $D_{in}$ [mm] and at least one fluid discharging outlet of diameter $D_{out}$ [mm], configured for placement in proximity to said at least one body cavity;

ii) at least one base in communication with said at least one nosepiece, said at least one base comprises at least one chamber configured to confine compressed and pressurized fluid at volume $V_{PF}$ [ml] and pressure $P_{PF}$ [barg];

iii) at least one hollow puncturing member; said at least one hollow puncturing member is characterized by a first end comprising at least one sharp end and a second end in fluid communication with said at least one base; said first end and second end being fluidly interconnected by at least one hollow tube; said at least one fluid inlet port of said at least one capsule is configured by means of size and shape to interface in a sealable manner with said first end of said at least one puncturing member;

b) actuating said at least one base thereby piercing of said at least one capsule in said at least one nosepiece, by means of said at least one puncturing member;

wherein said at least one sharp end comprises at least one orifice through which said pressurized fluid enters said at least one capsule; and c) enclosing and sealing, by at least one sealing septum, the at least one orifice prior to actuating said at least one base.

35. The method of claim 34, wherein step (b) of actuating said at least one base additionally comprising pressing said at least one base.

36. The method of claim 34, wherein step (b) of actuating said at least one base enables the pressurized fluid to exit said at least one chamber and entrain through said at least one hollow tube of said at least one hollow puncturing member to said at least one capsule, entrain said one or more substances and deliver said one or more substances the same to said at least one body cavity.

37. The method of claim 34, wherein step (b) of actuating said at least one base results in releasing said volume $V_{PF}$ [ml] of said pressurized fluid at pressure $P_{PF}$ [barg] within a period of time that is less than 500 milliseconds (dT); out of said at least one chamber, via said at least one fluid inlet port thereby entraining said one or more substances and erupting via said at least one fluid discharging outlet into said at least one body cavity, such that the release time of said $V_{sub}$ [ml or mg] of said one or more substances and said $V_{PF}$ [ml] of said pressurized fluid, $dT_{release}$ is less than 500 milliseconds.

38. The method of claim 34, wherein said second end of said at least one hollow puncturing member and said at least one chamber are formed as a single unit, such that an upper surface of said at least one chamber is integrated with said second end of said at least one hollow puncturing member.

39. The method of claim 34, wherein actuating said at least one base comprises removing said at least one sealing septum to enable exit of said pressurized fluid through said at least one orifice in said at least one hollow puncturing member.

40. The method of claim 39, wherein actuating said at least one base comprises pressing said at least one base, and wherein during said pressing, said at least one hollow puncturing member is pushed towards said at least one nosepiece such that a bottom most part of said at least one nosepiece removes said at least one sealing septum from enclosing said at least one orifice in said at least one sharp end of said at least one hollow puncturing member.

41. The method of claim 40, wherein said at least one sharp end of said at least one hollow puncturing member comprises said at least one orifice, and wherein following actuating of said at least one base, said pressurized fluid enters said at least one capsule through said at least one orifice of said at least one hollow puncturing member.

42. The method of claim 34, wherein said at least one chamber comprising at least one orifice through which said pressurized fluid exits said at least one chamber.

43. The method of claim 42, wherein said second end of said at least one hollow puncturing member seals said at least one orifice of said at least one chamber, prior to actuating said at least one base.

44. The method of claim 43, wherein actuating said at least one base comprises unsealing said at least one orifice of said at least one chamber such that said pressurized fluid exits through said at least one orifice of said at least one chamber into said at least one hollow tube of said at least one hollow puncturing member.

45. The method of claim 44, wherein said at least one sharp end of said at least one hollow puncturing member comprises said at least one orifice, and wherein following actuating of said at least one base, said pressurized fluid enters said at least one capsule through said at least one orifice of said at least one hollow puncturing member.

46. The method of claim 34, wherein said at least one nosepiece comprises at least one nosepiece cover configured by means of size and shape to cover, in a sealable manner, at least partially said at least one nosepiece.

47. The method of claim 46, wherein removal of said at least one nosepiece cover is obtained by at least one action selected from a group consisting of sliding said at least one nosepiece cover along said at least one nosepiece, rotating said at least one nosepiece cover around said at least one nosepiece, rotating said at least one nosepiece cover around a hinge on an exterior of said at least one nosepiece and any combination thereof.

48. The method of claim 34, wherein said at least one nosepiece comprising at least one nosepiece cover and said at least one nosepiece are coupled to each other.

49. The method of claim 48, wherein said said at least one nosepiece cover and said at least one nosepiece are reversibly coupled to each other.

50. The method of claim 49, wherein removal of said at least one nosepiece cover results in piercing said at least one capsule to provide said at least one fluid discharging outlet.

51. The method of claim 50, said at least one nosepiece cover is adapted to pierce said at least one capsule to enable said at least one fluid discharging outlet.

52. The method of claim 50, wherein said at least one nosepiece comprises at least one port through which said one or more substances exits said at least one nosepiece, such that said at least one nosepiece cover seals said at least one port and removal thereof removes said seal.

53. The method of claim 34, wherein said at least one capsule is selected from a group consisting of pierceable container, a blow-fill-seal and a form-fill-seal and any combination thereof.

54. The method of claim 34, wherein said at least one chamber is a container adapted to hold said pressurized fluid at said pressure $P_{PF}$ for a period of time.

55. The method of claim 34, wherein said at least one capsule is made of at least one material selected from a group consisting of high- or low-density polyethylene, high- or low-density polypropylene, any plastic resin, glass and any combination thereof.

56. The method of claim 34, further comprising delivering said $V_{sub}$ of said one or more substances and $V_{PF}$ of said pressurized fluid through said at least one fluid discharging outlet of diameter D [mm] wherein at least one of the following is held true:

a) $V_{PF}$ is in a range of 1 to 50 ml;
b) $V_{sub}$ is in a range of about 0.01 to about 7 ml;
c) $D_{in}$ and/or $D_{out}$ is in a range of 0.2 to 6 mm;
d) $P_{PF}$ is in a range of about 0 to about 10 barg;
e) a pressure velocity is greater than 0.001 barg/ms;
f) said pressure velocity is greater than 0.01 barg/ms;
g) volume rate $dV_{sub}/dT$ or $dV_{sub}/dT_{release}$ is greater than 0.0001 ml/ms;
h) said volume rate $dV_{sub}/dT$ or $dV_{sub}/dT_{release}$ is greater than 0.001 ml/ms;
i) a volume rate $dV_{PF}/dT$ or $dV_{PF}/dT_{release}$ is greater than 0.001 ml/ms;
j) said volume rate $dV_{PF}/dT$ or $dV_{PF}/dT_{release}$ is greater than 0.01 ml/ms; and
k) any combination thereof.

57. The method of claim 56, additionally comprising at least one of the following steps:

a) selecting said at least one body cavity from a group consisting of a nasal cavity, a mouth, a throat, an ear, an eye, a vagina, a rectum, a urethra, and any combination thereof;
b) selecting said pressurized fluid comprises a pressurized gas from a group consisting of: air, nitrogen, oxygen, carbon dioxide, helium, neon, xenon, nitric oxide and any combination thereof;
c) dispensing said one or more substances, and during said step of dispensing, forming a plume of aerosol with predetermined distribution from a mixture of [said] a predetermined volume $V_{gas}$ [ml] of said pressurized gas and said predetermined volume $V_{sub}$ [ml or mg] entrained within it; selecting said predetermined distribution from a group consisting of: a homogeneous distribution, a heterogeneous distribution; selecting said heterogeneous distribution from a group consisting of: an arbitrary distribution, a distribution in which the density of said one or more substances within said mixture follows a predetermined pattern, and any combination thereof; selecting characteristics of said aerosol from a group consisting of: particle size, particle shape, particle distribution, and any combination thereof, are determinable from a group consisting of: said predetermined volume of said pressurized gas, said predetermined volume of said one or more substances, a predetermined pressure of said pressurized gas, a predetermined orifice size, and any combination thereof;
d) selecting said one or more substances from a group consisting of: a gas, a liquid, a powder, a slurry, a gel, a suspension, and any combination thereof;
e) storing at least one said one or more substances under either an inert atmosphere or under vacuum, thereby preventing reactions during storage; and
f) characterizing a dose-response curve for brain concentration of said one or more substances to be of substantially linear form; and
g) a dose-response curve for brain concentration having a fit selected from a group consisting of logarithmic, parabolic, exponential, sigmoid, power-low, and any combination thereof; of said one or more substances when administered nasally via said device.

58. The method of claim 34, wherein said one or more substances is selected from a group consisting of proteins; stem-cells; cells, organs, portions, extracts, and isolations thereof; macro-molecules; RNA or other genes and proteins-encoding materials; neurotransmitters; receptor antagonists; hormones; Ketamine; Glucagon; substrates to treat one of eth followings: anaphylaxis, Parkinson, seizures and opioid overdose; epinephrine; atropine; metoclopramide; commercially available naloxone; Esketamine; edaravone; valbenazine; deutetrabenazine; ocrelizumab; safinamide; nusinersen; daclizumab; pimavanserin; aripiprazole lauroxil; cariprazine; brexpiprazole; eslicarbazepine acetate; flutemetamol F18 injection; vortioxetine; dimethyl fumarate; gadoterate meglumine; antibody mediated brain targeting drug delivery including aducanumab, gantenerumab, bapineuzumab, solanezumab, ofatumumab CD20, BIIB033, LCN2, HMGB1; insulin; oxytocin; orexin-A; leptin; benzodiazepine i.e. midazolam; naloxone; perillyl alcohol; camptothecin; phytochemicals including curcumin and chrysin; nucleotides; olanzapine; risperidone; Venlafaxine; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, at a therapeutically effective concentration.

59. The method of claim 34, wherein said at least one hollow puncturing member comprises a plurality of holes through which said pressurized fluid exits said at least one chamber and entrains said one or more substances, after activation of an activation mechanism.

60. The method of claim 34, wherein said at least one capsule is a hollow tube characterized by at least two ends interconnect to each other, at least one of which is positioned proximal to said at least one chamber.

61. The method of claim 60, wherein said at least one capsule comprises at least one spherical element positioned at at least one of said at least two ends, adapted to seal said at least one capsule and prevent leakage of said one or more substances therefrom.

62. The method of claim 60, wherein said at least one capsule comprises two spherical elements, each of which is disposed at each of said at least two ends, such that said one or more substances are positioned therebetween.

63. The method of claim 62, wherein said two spherical elements, once said pressurized fluid exits said at least one chamber, are adapted to mix said one or more substances.

64. The method of claim 60, wherein said at least one capsule comprises at least one membrane positioned at at least one of said at least two ends, adapted to seal said at least one capsule and prevent leakage of said one or more substances therefrom.

65. The method of claim 64, wherein said at least one capsule comprises two membranes, each of which is disposed ends, such that said one or more substances are positioned therebetween.

66. The method of claim 60, wherein said at least one capsule comprises at least one duckbill valve positioned by at least one of said at least two ends, adapted to seal said at least one capsule and prevent leakage of said one or more substances therefrom.

67. The method of claim 66, wherein said at least one capsule comprises two duckbill valves, each of which is disposed at each of said at least two ends, such that said one or more substances are positioned therebetween.

68. The method of claim 60, wherein said at least one capsule comprises at least one spherical element, membrane, uni-directional valve, duckbill valve and any combination thereof.

69. The method of claim 34, wherein said at least one chamber comprises at least one orifice through which said pressurized fluid enters said at least one hollow puncturing member.

70. The method of claim 69, wherein, after actuating said at least one base, said pressurized fluid exits said at least one chamber and enters said at least one hollow puncturing member through said at least one orifice of said at least one chamber.

71. The method of claim 34, wherein said at least one chamber comprises at least one material selected from a group consisting of high- or low-density polyethylene, high- or low-density polypropylene, any plastic resin, glass, plastics, Aluminum and any combination thereof.

72. A device for delivering either one or more substances within at least one body cavity, comprising:

(i) at least one nosepiece comprising at least one capsule comprising $V_{sub}$ [ml or mg] of said one or more substances; said at least one capsule having at least one fluid inlet port of diameter Din [mm] and at least one fluid discharging outlet of diameter $D_{out}$ [mm], configured for placement in proximity to said at least one body cavity;

(ii) at least one base in communication with said at least one nosepiece, said at least one base comprises at least one chamber configured to confine compressed and pressurized fluid at volume $V_{PF}$ [ml] and pressure $P_{PF}$ [barg];

(iii) at least one hollow puncturing member; said at least one hollow puncturing member is characterized by a first end comprising at least one sharp end and a second end in fluid communication with said at least one base; said first end and second end being fluidly interconnected by at least one hollow tube; said at least one fluid inlet port of said at least one capsule is configured to interface in a sealable manner with said at least one sharp end of said at least one puncturing member;

wherein actuation of said at least one base is configured to enable piercing of said at least one capsule to provide said at least one fluid inlet port, by means of said at least one sharp end of said at least one hollow puncturing member to enable the pressurized fluid to exit said at least one chamber and entrain through said at least one hollow tube of said at least one hollow puncturing member to said at least one capsule, entrain said one or more substances and deliver said one or more substances to said at least one body cavity;

wherein said at least one sharp end comprises at least one orifice through which said pressurized fluid enters said at least one capsule; and wherein said second end of said at least one hollow puncturing member seals at least one orifice of said at least one chamber, prior to actuation of said device.

* * * * *